(12) United States Patent
Henkin

(10) Patent No.: US 8,968,706 B2
(45) Date of Patent: Mar. 3, 2015

(54) METHODS FOR DIAGNOSING AND TREATING LOSS OR DISTORTION OF TASTE

(71) Applicant: Robert I. Henkin, Bethesda, MD (US)

(72) Inventor: Robert I. Henkin, Bethesda, MD (US)

(*) Notice: Subject to any disclaimer, the term of this patent is extended or adjusted under 35 U.S.C. 154(b) by 0 days.

(21) Appl. No.: 13/932,613

(22) Filed: Jul. 1, 2013

(65) Prior Publication Data

US 2014/0073654 A1    Mar. 13, 2014

Related U.S. Application Data

(60) Continuation of application No. 12/649,320, filed on Dec. 29, 2009, now Pat. No. 8,506,934, which is a division of application No. 11/415,942, filed on May 1, 2006, now Pat. No. 7,670,849.

(60) Provisional application No. 60/743,495, filed on Mar. 15, 2006, provisional application No. 60/676,252, filed on Apr. 29, 2005.

(51) Int. Cl.
| | |
|---|---|
| *A61K 49/00* | (2006.01) |
| *A61K 35/24* | (2006.01) |
| *C12P 19/30* | (2006.01) |
| *G01N 33/567* | (2006.01) |
| *G01N 33/566* | (2006.01) |
| *G01N 33/68* | (2006.01) |
| *A61K 31/522* | (2006.01) |
| *G01N 33/574* | (2006.01) |
| *G01N 33/576* | (2006.01) |
| *C12Q 1/68* | (2006.01) |

(52) U.S. Cl.
CPC .......... *G01N 33/566* (2013.01); *G01N 33/6893* (2013.01); *A61K 31/522* (2013.01); *G01N 33/57449* (2013.01); *G01N 33/576* (2013.01); *C12Q 1/6883* (2013.01); *C12Q 1/6886* (2013.01); *G01N 2800/52* (2013.01); *G01N 2800/042* (2013.01); *G01N 2800/14* (2013.01); *C12Q 2600/118* (2013.01)
USPC .......... 424/10.1; 424/10.4; 424/571; 435/92; 435/333; 436/503

(58) Field of Classification Search
CPC combination set(s) only.
See application file for complete search history.

(56) References Cited

U.S. PATENT DOCUMENTS

| | | | |
|---|---|---|---|
| 174,915 A | 3/1876 | Lorenz | |
| 4,066,405 A | 1/1978 | Henkin | |
| 4,146,501 A | 3/1979 | Henkin | |
| 4,652,521 A | 3/1987 | Confer et al. | |
| 4,683,195 A | 7/1987 | Mullis et al. | |
| 4,683,202 A | 7/1987 | Mullis et al. | |
| 4,800,159 A | 1/1989 | Mullis et al. | |
| 4,992,445 A | 2/1991 | Lawter et al. | |
| 5,001,139 A | 3/1991 | Lawter et al. | |
| 5,023,252 A | 6/1991 | Hseih | |
| 5,079,142 A | 1/1992 | Coleman et al. | |
| 5,132,324 A | 7/1992 | Meglasson | |
| 5,384,308 A | 1/1995 | Henkin | |
| 5,525,329 A * | 6/1996 | Snyder et al. | ........... 424/45 |
| 5,591,645 A | 1/1997 | Rosenstein | |
| 5,601,986 A | 2/1997 | Takacs | |
| 5,614,627 A | 3/1997 | Takase et al. | |
| 5,622,871 A | 4/1997 | May et al. | |
| 5,707,802 A | 1/1998 | Sandhu et al. | |
| 5,714,993 A | 2/1998 | Keoshkerian et al. | |
| 5,788,967 A | 8/1998 | Henkin | |
| 5,849,741 A | 12/1998 | Watanabe et al. | |
| 5,859,006 A | 1/1999 | Daugan | |
| 5,869,516 A | 2/1999 | Arlt et al. | |
| 6,207,703 B1 | 3/2001 | Ponikau | |
| 6,228,660 B1 | 5/2001 | May et al. | |
| 6,387,639 B1 | 5/2002 | Posner et al. | |
| 6,929,925 B1 | 8/2005 | Zuker et al. | |
| 7,109,042 B2 | 9/2006 | May et al. | |
| 8,293,489 B2 | 10/2012 | Henkin | |
| 8,580,801 B2 | 11/2013 | Henkin | |

(Continued)

FOREIGN PATENT DOCUMENTS

| | | |
|---|---|---|
| EP | 0967214 A1 | 12/1999 |
| WO | WO 96/26940 A1 | 9/1996 |

(Continued)

OTHER PUBLICATIONS

Misaka et al., Taste buds have a cyclic nucleotideactivated channel, CNGust, J. Biol. Chem. 272, 22623-22629, 1997.*

(Continued)

Primary Examiner — Elly-Gerald Stoica

(74) Attorney, Agent, or Firm — Wilson, Sonsini, Goodrich & Rosati, PC

(57) ABSTRACT

The invention is directed to a method of detecting a biological substance in the nasal secretion and diagnosing a disease following the detection of the biological substance wherein the biological substance is not related to a respiratory disease. The invention also provides treatment of the diseases following the detection of the biological substance and/or diagnosis of the disease. In some embodiments, the diseases are cancer, hepatitis, smell loss, taste loss, diabetes, and leprosy. The invention also provides a kit for diagnosing a disease.

The present invention includes methods of analyzing samples from the nose for the detection of biological substances. In particular, nasal secretion or nasal mucus is collected and analyzed for biological substances. The results of this analysis are then suitable for use in diagnosis, prognosis, and determination of suitability of therapeutic interventions.

22 Claims, 12 Drawing Sheets

(56) References Cited

U.S. PATENT DOCUMENTS

| | | | |
|---|---|---|---|
| 8,663,938 | B2 | 3/2014 | Henkin |
| 2006/0275801 | A1 | 12/2006 | Henkin |
| 2008/0318913 | A1 | 12/2008 | Fox et al. |
| 2010/0022563 | A1 | 1/2010 | Henkin |
| 2010/0227875 | A1 | 9/2010 | Henkin |
| 2011/0166166 | A1 | 7/2011 | Henkin |
| 2012/0178768 | A1 | 7/2012 | Henkin |
| 2013/0011849 | A1 | 1/2013 | Henkin |

FOREIGN PATENT DOCUMENTS

| | | |
|---|---|---|
| WO | WO 96/41194 A1 | 12/1996 |
| WO | WO 97/03675 A1 | 2/1997 |
| WO | WO 97/03985 A1 | 2/1997 |
| WO | WO 97/43287 A1 | 11/1997 |
| WO | WO 98/17668 A1 | 4/1998 |
| WO | WO 98/49166 A1 | 11/1998 |
| WO | WO 99/01135 A1 | 1/1999 |
| WO | WO 99/21562 A1 | 5/1999 |
| WO | WO 99/30697 A2 | 6/1999 |
| WO | WO 01/48477 A1 | 7/2001 |
| WO | WO 03/25224 A2 | 3/2003 |
| WO | WO 03/25224 A3 | 11/2003 |
| WO | WO 2008/141438 A1 | 11/2008 |
| WO | WO 2009/115235 A1 | 9/2009 |
| WO | WO 2010/147981 A1 | 12/2010 |
| WO | WO 2012/016845 A2 | 2/2012 |
| WO | WO 2012/016889 A2 | 2/2012 |

OTHER PUBLICATIONS

Margolskee R.F., Molecular mechanism of taste transduction, Pure Appl. Chem., 74, 1125-1133, 2002.*
Nakajima et al., Studies on Cyclic Nucleotides in Bronchopulmonary Diseases with Special Reference to cAMP, cGMP in Patients with Nasal Allergy and Bronchial AsthmaActa Med. Kinki Univ., 4, 257-272, 1979.*
U.S. Appl. No. 14/152,927, filed Jan. 10, 2014, Henkin.
Abbott Axsym system. Theophylline II package insert. Abbott Laboratories. 2003.
Agarwal, et al. A simple method for simultaneous estimation of zinc and copper in erythrocytes. Bio. Tr. Elem. Res. 1985;7: 199-208.
Ajani, et al. Alcohol consumption and risk of coronary heart disease by diabetes status. Circulation. Aug. 1, 2000;102(5):500-5.
Anholt, et al. Molecular neurobiology of olfaction. Crit. Rev. Neurobiol. 1993;7:1-22.
Asakura, et al. cAMP and cGMP in the human parotid saliva. Arch. Otorhinolaryngol. 1980;226:145-154.
Atkinson, et al. The pathogenesis of insulin-dependent diabetes mellitus. New Engl. J. Med. 1994;331:1428-1436.
Bakalyar, et al. Identification of a specialized adenylyl cyclase that may mediate odorant detection. Science. Dec. 7, 1990;250(4986):1403-6.
Bogardus, et al. Relationships between insulin secretion, insulin action, and fasting plasma glucose concentration in nondiabetic and noninsulin-dependent diabetic subjects. J Clin Invest. Oct. 1984;74(4):1238-46.
Borisy, et al. High-affinity cAMP phosphodiesterase and adenosine localized in sensory organs. Brain Res. May 7, 1993;610(2):199-207.
Breer. Molecular reaction cascades in olfactory signal transduction. J Steroid Biochem Mol Biol. Oct. 1991;39(4B):621-5.
Bromley, et al. Smell and taste disorders: a primary care approach. Amer. Fam. Physician. 2000;61:427-436.
Cai, et al. Neuronal cyclic AMP controls the developmental loss in ability of axons to regenerate. J. Neurosci. 2001;21:4731-4739.
Cai, et al. Prior exposure to neurotrophins blocks inhibition of axonal regeneration by MAG and myelin via a cAMP dependent mechanism. Neuron. 1999;22:89-101.
Carlsson, et al. Alcohol consumption and the increase of Type II diabetes: Finnish twin cohort study. Diabetes Care. 2003, 26: 2785-2790.
Cho, et al. Development of udenafil-loaded microemulsions for intranasal delivery: in vitro and in vivo evaluations. Int J Pharm. Feb. 28, 2012;423(2):153-60. doi: 10.1016/j.ijpharm.2011.12.028. Epub Dec. 23, 2011.
Chou. Wake up and smell the coffee. Caffeine, coffee, and the medical consequences. West J Med. Nov. 1992;157(5):544-53.
Church, et al. Hyposmia associated with atopy. Ann. Aller. 1978;40:105-109.
Cicinelli, et al. Post-stroke reorganization of brain motor output to the hand: a 2-4 month follow-up with focal magnetic transcranial stimulation. Electroencephalogr Clin Neurophysiol. Dec. 1997;105(6):438-50.
Cullen, et al. Disorders of smell and taste. Med. Clin. North Amer. 1999;83:57-74.
Davidson, et al. Smell impairment: can it be reversed? Postgrad. Med. 1995;98:107-109, 112-118.
Deems, et al. Smell and taste disorders, a study of 750 patients from the University of Pennsylvania Smell and Taste Center. Arch. Otolaryngol. Head Neck Surg. 1991;177:519-528.
Doerty, et al. Carbonic anhydrase (CA) activity in nasal mucus appears to be a marker for loss of smell (hyposmia) in humans. J. Invest. Med. 1997;45:237A.
Doty, et al. Human odor intensity perception: correlation with frog epithelial adenylate cyclase activity and transepithelial voltage response. Brain Res. Sep. 10, 1990;527(1):130-4.
Elshafeey Ah, et al. Intranasal microemulsion of sildenafil citrate: in vitro evaluation and in vivo pharmacokinetic study in rabbits. AAPS PharmSciTech. 2009;10(2):361-7. doi: 10.1208/s12249-009-9213-6. Epub Mar. 31, 2009.
FDA. Guidance for industry. Estimating the maximum safe starting dose in initial clinical trials for therapeutics in adult healthy volunteers. Center for Drug Evaluation and Research. Jul. 2005.
Firestein, et al. Regulation of sensory neuron precursor proliferation by cyclic GMP dependent protein kinase. J. Neurochem. 1998;71:1846-1853.
Firestein, et al. Single odor-sensitive channels in olfactory receptor neurons are also gated by cyclic nucleotides. J. Neurosci. 1991;11:3565-72.
Franz, et al. Evidence-based nutrition principles and recommendations for diabetes and related complications. Diabetes Care. 2002, 25:148-198.
Gillespie, et al. Pharmacologic Management of Chronic Rhinosinusitis, Alone or with Nasal Polyposis. Current Allergy and Asthma Reports, 2004, vol. 4, No. 6, pp. 478-485.
Glenert, et al. A single assay for cyclic adenosine 3':5'-monophosphate in human saliva. J. Cyclic Nucleotide Protein Phosphor. Res. 1985;10:451-461.
Harris, et al. Clinical evaluation and symptoms of chemosensory impairment: one thousand consecutive cases from the Nasal Dysfunction Clinic in San Diego. Amer. J. Rhinol 2006;20:101-108.
Henkin, et al. A double blind study of the effects of zinc sulfate on taste and smell dysfunction. Amer. J. Med. Sci. 1976;272: 285-299.
Henkin, et al. A zinc protein isolated from human parotid saliva. Proc. Nat. Acad. Sci. USA 1975;72:488-492.
Henkin, et al. Aberrant signaling in the olfactory system: a mechanism for smell loss. FASEB Journal, vol. 18, No. 4-5, pp. Abst. 792.7, 2004.
Henkin, et al. Age related changes in cyclic nucleotides in saliva and nasal mucus possible feedback mechanism in development of gustatory and olfactory receptor function. FASEB J. 2005;19:A1368.
Henkin, et al. cAMP and cGMP in human parotid saliva: relationships to taste and smell dysfunction, gender and age. Amer. J. Med. Sci. 2007;334:431-440.
Henkin, et al. cAMP and cGMP in nasal mucus related to severity of smell loss in patients with smell dysfunction. Clinical Invest. Med. 2008;31:E78-E84.
Henkin, et al. cAMP and cGMP in nasal mucus: relationships to taste and smell dysfunction, gender and age. Clinical Invest. Med. 2008;31:E71-E77.
Henkin, et al. Decreased parotid saliva gustin/carbonic anhydrase VI secretion: an enzyme disorder manifested by gustatory and olfactory dysfunction. Amer. J. Med. Sci. 1999;318:380-391.

(56) References Cited

OTHER PUBLICATIONS

Henkin, et al. Decreased parotid salivary cyclic nucleotides related to smell loss severity in patients with taste and smell dysfunction. Metabolism. Dec. 2009;58(12):1717-23. doi: 10.1016/j.metabol. 2009.05.027. Epub Jul. 23, 2009.
Henkin, et al. Effective treatment of smell loss with theophylline. Exper. Biol. 2008;22:B976.2.
Henkin, et al. Efficacy of exogenous zinc in treatment of patients with carbonic anhydrase VI deficiency. Amer. J. Med. Sci. 1999;318:392-404.
Henkin, et al. Fractionation of human parotid saliva. J. Biol. Chem. 1978;253:7556-7565.
Henkin, et al. Hypogeusia, dysgeusia, hyposmia and dysosmia following influenza-like infection. Ann. Otol. Rhin Laryngol. 1975;84:672-682.
Henkin, et al. Idiopathic hypogeusia with dysgeusia, hyposmia and dysosmia: a new syndrome. J. Amer. Med. Assoc. 1971;217:434-440.
Henkin, et al. Insulin receptors as well as insulin are present in saliva and nasal mucus. Journal of Investigative Medicine. 2006; 54(Suppl. 2):S378.
Henkin, et al. Interleukin 6 in hyposmia. JAMA Otolaryngol Head Neck Surg. Jul. 2013;139(7):728-34. doi: 10.1001/jamaoto.2013. 3392.
Henkin, et al. Intranasal theophylline treatment of hyposmia and hypogeusia: a pilot study. Arch Otolaryngol Head Neck Surg. Nov. 2012;138(11):1064-70. doi: 10.1001/2013.jamaoto.342.
Henkin, et al. Nasal seroproteins: a new frontier in the exploration of physiology and pathology of nasal and sinus disease. New Frontiers in Immunobiology. 2000; pp. 127-152.
Henkin, et al. Rapid changes in taste and smell function following transcranial magnetic stimulation (TCMS) in humans: relationship to CAN plasticity. FASEB J. 2002; 16:A878.
Henkin, et al. Treatment of abnormal chemsensation in human taste and smell. In: Norris DM, ed. Perception of Behavioral Chemicals. Amsterdam, netherlands: Elsevier/North Holland Biomedical Press; 1981:227-265.
Henkin, R.I. et al. "Is Increased IL-6 the Result or Cause of Smell Loss in Patients with Hyposmia?", FASEB Journal, 2009, vol. 23 (Meeting Abstract Supplement), Abstract 835.1.
Henkin, R.I. et al. "New Data on Human Cytokine Changes with Age", FASEB Journal, 2009, vol. 23 (Meeting Abstract Supplement), Abstract 571.9.
Henkin, R.I. et al. "Taste and smell function in chronic disease: A review of clinical and biochemical evaluations of taste and smell dysfunction in over 5000 patients at the Taste and Smell Clinic in Washington, DC", American Journal of Otolaryngology-Head and Neck Medicine and Surgery, 2013, vol. 34, pp. 477-489.
Henkin. Concepts of therapy in taste and smell dysfunction: repair of sensory receptor function as primary treatment. Olfaction and Taste XI, (Kurihara, K., Suzuki, N., Ogawa, H., Eds.), Springer Verlag, 1994, pp. 568-573.
Henkin. Dichotomous changes in cAMP and cGMP in human parotid saliva after oral theophylline. FASEB J. 2003;17:A1028.
Henkin. Drug-induced taste and smell diorders. Incidence, mechanisms and management related primarily to treatment of sensory receptor dysfunction. Drug safety. 1994; 11(5):318-377.
Henkin. Effects of ACTH, adrenocorticosteroids and thyroid hormone on sensory function, in Anatomical Neuroendocrinology, (Stumpf, W.E., Grant, L.D., Eds.), Karger, A.G., Basel, 1975, pp. 298-316.
Henkin. Evaluation and treatment of human olfactory dysfunction, in Otolaryngology (English, G.M. Ed.), Lippincott, Philadelphia, 1993, vol. 2, pp. 1-86.
Henkin. Olfaction in human disease. In: English GM, ed. Loose-leaf Series of Otolaryngology. New York, NY: Harper and Row; 1982:1-39.
Henkin. Taste and smell disorders, human. Encyclopedia of Neuroscience, 3rd Ed., (Adelman, G., Smith, B.H., Eds.), Birkhauser, Boston, 2004.

Henkin. The definition of primary and accessory areas of olfaction as the basis for a classification of decreased olfactory acuity, in Olfaction and Taste II, (Hayashi, T. Ed.), Pergamon Press, London, 1967, pp. 235-252.
Henkin. The role of adrenal corticosteroids in sensory processes, in Adrenal Gland, (Blaschko, H., Sayers, G., Smith, A.D., Eds.), Handbook of Physiology. Endocrinology, Washington, DC. Amer. Physiol. Soc., Sect. 7, vol. VI, 1975, pp. 209-230.
Henkin. Zinc, saliva and taste: Interrelationships of gustin, nerve growth factor, saliva and zinc, in Zinc and Copper in Clinical Medicine, (Hambidge, K.M., Nichols, B.L., Eds.), Spectrum Publ. Inc., Jamaica, NY, 1978, pp. 35-48.
Huque, et al. Odorant- and guanine nucleotide-stimulated phosphoinositide turnover in olfactory cilia. Biochem Biophys Res Commun. May 29, 1986;137(1):36-42.
International search report and written opinion dated Apr. 8, 2014 for PCT/US2014/014940.
International search report and written opinion dated Dec. 5, 2013 for PCT/US2013/064416.
International search report and written opinion dated Dec. 12, 2013 for PCT/US2013/063331.
Kanamori, et al. Origin of cyclic adenosine monophosphate in saliva. J. Dent. Res. 1975;54:535-539.
Kim, et al. Defects in the peripheral taste structure and function in the MRL/lpr mouse model of autoimmune disease. PLoS One. 2012;7(4):e35588. doi: 10.1371/journal.pone.0035588. Epub Apr. 19, 2012.
Krägelund, et al. N-terminal Pro-B-type natriuretic-peptide and long-term mortality in stable coronary heart disease. New Engl. J. Med. 2006; 252:666-675.
Kurihara, et al. High activity of adenyl cyclase in olfactory and gustatory organs. Biochem Biophys Res Commun. Jul. 11, 1972;48(1):30-4.
Lancet, et al. Molecular transduction in smell and taste. Cold Spring Harb Symp Quant Biol. 1988;53 Pt 1:343-8.
Law, et al. Distribution of calmodulin in taste buds. Life Sci. 1985; 36:1189-1195.
Law, et al. Low parotid saliva calmodulin in patients with taste and smell dysfunction. Biochem Med Metab Biol. Aug. 1986;36(1):118-24.
Law, et al. Zinc deficiency decreases the activity of calmodulin regulated cyclic nucleotide phosphodiesterases in vivo in selected rat tissues. Biol Trace Elem Res. Aug. 1988;16(3):221-6.
Lee, et al. Thiolated chitosan nanoparticles enhance anti-inflammatory effects of intranasally delivered theophylline. Respir Res. Aug. 24, 2006;7:112.
Levin, et al. Soluble endoglin and other circulating antiangiogenic factors in preeclampsia. New Engl. J. Medicine. 2006;355:992-1005.
Levy, et al. Increased brain activation in response to odors in patients with hyposmia after theophylline treatment demonstrated by fMRI. J. Comp. Asst. Tomog. 1998;22:760-770.
Lindheimer, et al. Explaining and predicting preeclampsia. New Engl. J. Medicine. 2006;355:1056-1058.
Lowe, et al. Contribution of the ciliary cyclic nucleotide-gated conductance to olfactory transduction in the salamander. J Physiol. Mar. 1993;462:175-96.
Maitra, et al. The pancreas in Pathological Basis of Disease. 7th Edition. Elsevier. 2004; pp. 1155-1207.
Margolskee, Robert F. Molecular mechanisms of taste transduction. Pure and applied chemistry. 2002; 74(7):1125-1133.
McAuley, et al. Diagnosing insulin resistance in the general population. Diabetes Care. Mar. 2001;24(3):460-4.
Meret, et al. Simultaneous direct estimation by atomic absorption spectrophotometry of copper and zinc in serum, urine, and cerebrospinal fluid. Clin Chem. May 1971;17(5):369-73.
Moharram, et al. Growth factor regulation in human olfactory system function: the role of transcranial magnetic stimulation (TCMS). FASEB J. 2004; 18(4):A201.
Moon, et al. Regulation of intracellular cyclic GMP levels in olfactory sensory neurons. J. Neurochem. 2005;95:200-9.
Nakamura, et al. Proceedings of the 25th Japanese Symposium on Taste and Smell: 1. Current and Ca influx induced by intracellular cAMP in the newt olfactory receptor. Chem Sense. 1991; 17:85-116.

(56) References Cited

OTHER PUBLICATIONS

Neumann, et al. Regeneration of sensory axons within the injured spinal cord induced by intraganglionic cAMP elevation. Neuron. 2002;34:885-893.
Office action dated Jan. 14, 2011 for U.S. Appl. No. 12/649,320.
Office action dated Mar. 9, 2012 for U.S. Appl. No. 12/508,530.
Office action dated Apr. 17, 2007 for U.S. Appl. No. 11/415,942.
Office action dated Apr. 17, 2008 for U.S. Appl. No. 11/415,942.
Office action dated May 25, 2011 for U.S. Appl. No. 12/649,320.
Office action dated May 26, 2009 for U.S. Appl. No. 11/415,942.
Office action dated Jul. 26, 2012 for U.S. Appl. No. 12/508,530.
Office action dated Aug. 10, 2012 for U.S. Appl. No. 12/649,320.
Office action dated Oct. 17, 2007 for U.S. Appl. No. 11/415,942.
Office action dated Nov. 12, 2008 for U.S. Appl. No. 11/415,942.
Pace, et al. Odorant-sensitive adenylate cyclase may mediate olfactory reception. Nature. 1985;316:255-8.
Papathanassiu, et al. cAMP is present in human nasal mucus and may act as a growth factor in cells of the olfactory epithelium. FASEB J. 2002;16:A1153.
Pelangaris, et al. Oncogenic co-operation in beta-cell tumorigenesis. Endocr Relat Cancer. Dec. 2001;8(4):307-14.
Philips, et al. Factors determining the appearance of glucose in upper and lower respiratory tract secretions. Intensive Care Med. Dec. 2003;29(12):2204-10.
Rickli, et al. Carbonic anhydrases from human erythrocytes. Preparation and properties of two enzymes. J Biol Chem. Apr. 1964;239:1065-78.
Riste, et al. High prevalence of Type 2 diabetes in all ethnic groups, including Europeans, in a British Inner City. Diabetes Care. 2001;24:1377-1383.
Rock, et al. Inhibitors of the proteosome block the degradation of most cell proteins and the generation of peptides presented on MHC class 1 molecules. Cell. 1994;78:761-771.
Rosezweig, et al. Possible novel mechanism for bitter taste mediated through cGMP. J. Neurophysiol. 1999;81: 1661-5.
Sano, et al. Immuno PCR: very sensitive antigen detection by means of specific antibody-DNA conjugates. Science. 1992;258:120-122.
Schaeffer, et al. Detection of cAMP in parotid saliva of normal individuals. J. Dent. Res. 1973;52:629.
Schechter, et al. Abnormalities of taste and smell following head trauma. J. Neurol. Neurosurg. Psychiat. 1974;37:802-810.
Schechter, et al. Idiopathic hypogeusia: a description of the syndrome and a single blind study with zinc sulfate, in Internat. Rev. Neurobiol. Suppl. 1., (Pfeiffer, C., Ed.), Academic Press, NY, 1972, pp. 125-133.
Schiffman, et al. Methyl xanthines enhance taste: evidence for modulation of taste by adenosine receptor. Pharmacol Biochem Behav. Feb. 1985;22(2):195-203.
Seal, et al. Point-of-care nucleic acid lateral flow tests. IVD Techology. 2006;41-51.
Seiden, et al. Office management of taste and smell disorders. Otolaryngol. Clin. North Amer. 1992;25:817-835.
Shepherd, et al. Sensory transduction entering the mainstream of membrane signaling. Cell. 1991;67:845-851.
Shin, et al. Virus-induced Type 1 IFN stimulates generation of immunoproteasomes at the site of infection. J. Clin. Invest. 2006;116(11):3006-3014.
Shirley, et al. Olfactory adenylate cyclase of the rat. Stimulation by odorants and inhibition by Ca2+. Biochem J. Dec. 1, 1986;240(2):605-7.
Sklar, et al. The odorant-sensitive adenylate cyclase of olfactory receptor cells. Differential stimulation by distinct classes of odorants. J Biol Chem. Nov. 25, 1986;261(33):15538-43.
Sobottka, et al. Disseminated Encephalitozoon (Septata) intestinalis infection in a patient with AIDS: novel diagnostic approaches and autopsy-confirmed parasitological cure following treatment with albendazole. J Clin Microbiol. Nov. 1995;33(11):2948-52.
Suzuki. Proceedings of the 21st Japanese Symposium on Taste and Smell: cyclic nucleotides as intracellular messengers in the olfactory transduction process. Chem Sense. 1988; 13:311-332.
Temmel, et al. Characteristics of olfactory disorders in relation to major causes of olfactory loss. Arch. Otolaryngol. Head Neck Surg. 2002;128:635-641.
The Expert Committee. Report of the Expert Committee on the Diagnosis and Classification of Diabetes Mellitus. Diabetes Care. 2003;26:S5-S20.
Thompson. Cyclic nucleotide phosphodiesterase: pharmacology, biochemistry and function. Pharmacol. Ther. 1991;51:13-33.
Vaughan. Second wind for second-messenger research. Bioscience. 1987; 37:642-646.
Velicu, et al. Insulin is present in human saliva and nasal mucus. Journal of Investingative Medicine. 2006; 54:S385.
Velicu, et al. On the antiapoptotic mechanism of action of theophylline in restoring smell function in patients with hyposmia. J. Invest. Med. 2005;53(Suppl. 2):5402.
Voegels, et al. Expression of interleukins in patients with nasal polyposis. Otolaryngology—Head and Neck Surgery, 2005, vol. 132, No. 4, pp. 613-616.
Weinstock, et al. Olfactory dysfunction in humans with deficient guanine nucleotide-binding protein. Nature. Aug. 14-20, 1986;322(6080):635-6.
Weyer, et al. The natural history of insulin secretory dysfunction and insulin resistance in the pathogenesis of type 2 diabetes mellitus. J Clin Invest. Sep. 1999;104(6):787-94.
Will, et al. Cigarette smoking and diabetes mellitus from a large prospective cohort study. Int. J. Epidemiol. 2001; 30: 540-546.
Williams, G. Diabetes. In Endocrine Disorder. Oxford Testbook of Medicine. vol. 2, 4th Edition, Oxford Univ. Press 2003, pp. 317-359.
Woods, et al. Effect of hyperglycaemia on glucose concentration of human nasal secretions. Clin Sci (Load). May 2004;106(5):527-33.
Wysocki, et al. National Geographic Smell Survey: Effects of age are heterogeneous. Ann. NY Acad. Sci. 1989;561:12-28.

* cited by examiner

Lanes 1-7 HLA   M Mol. wt. markers – not plotted
      8-14 β-globin

METHODS FOR DIAGNOSING AND TREATING LOSS OR DISTORTION OF TASTE

CROSS-REFERENCE

This application is a continuation application of U.S. application Ser. No. 12/649,320, filed Dec. 29, 2009, now U.S. Pat. No. 8,506,934, issued on Aug. 13, 2013, which is a divisional application of U.S. application Ser. No. 11/415,942, filed May 1, 2006, now U.S. Pat. No. 7,670,849, issued on Mar. 2, 2010, which claims priority to U.S. Provisional Application No. 60/743,495, filed Mar. 15, 2006, and U.S. Provisional Application No. 60/676,252, filed Apr. 29, 2005, each of which is incorporated herein by reference in its entirety.

BACKGROUND OF THE INVENTION

Detection and identification of biological substances in tissue samples is used for the diagnosis, prognosis, and monitoring of diseases. Efficient identification of biological substances aids in devising effective treatment strategies.

Most of the current diagnostic techniques involve invasive procedures for the removal of tissue samples. Hence, there is need for the development of minimally invasive procedures for biological sample retrieval.

The present invention provides methods for detection of biological substances, diagnosis of diseases based on this detection and methods for treatment of the diseases after the diagnosis.

SUMMARY OF THE INVENTION

One aspect of the present invention is a method of diagnosing a disease by obtaining a nasal specimen, detecting a biological substance in the specimen, and diagnosing the disease, wherein the diagnosis is based on the detection of the biological substance, and wherein the biological substance is not related to a respiratory disease. In some embodiments, the biological substance is a nucleic acid. In some preferred embodiments, the nucleic acid is DNA, RNA or a combination thereof. In some embodiments, the detection is by a nucleic acid detection method. In some embodiments, the nucleic acid detection method is selected from the group consisting of polymerase chain reaction (PCR), ligase chain reaction (LCR), strand displacement amplification (SDA), self-sustained sequence replication (3SR), array based test, and TAQMAN. In some preferred embodiments, the nucleic acid detection method is PCR.

In some embodiments of the present invention, the biological substance is selected from the group consisting of insulin, insulin receptor, leptin, agouti-related protein, ghrelin, glucose, growth factor, caspase, adenylyl cyclase, and carbonic anhydrase. In some embodiments, the biological substance is selected from the group consisting of p53, or mutated p53, TNFα, TNFR I, TNFR II, TRAIL, IL3, endostatin, erythropoietin, bone morphogenic protein, brain derived neurotrophic factor, ciliary neurotrophic factor, granulocyte macrophage growth factor, hepatocyte growth factor, platelet derived growth factor, carbonic anhydrase VI, cAMP, cGMP, nitric oxide, insulin like growth factor, and endoglin. In some preferred embodiments, the biological substance is TNFα. In some preferred embodiments, the biological substance is insulin or insulin receptor. In some preferred embodiments, the biological substance is leptin or agouti-related protein. In some preferred embodiments, the biological substance is TRAIL or carbonic anhydrase VI. In some preferred embodiments, the biological substance is p53.

One aspect of the present invention is method of treating a disease wherein the treatment is based on diagnosing the disease, wherein the diagnosis is based on a detection of a biological substance in a nasal specimen, and wherein the biological substance is not related to a respiratory disease. In some embodiments, the disease is selected from the group consisting of smell loss, taste loss, diabetes, obesity, anorexia, cancer, leprosy, and hepatitis. In some preferred embodiments, the cancer is ovarian cancer. In some embodiments, the treatment is selected from the group consisting of oral administration, transmucosal administration, buccal administration, nasal administration, parental administration, intravenous, subcutaneous, intramuscular, sublingual, transdermal administration, and rectal administration. In some preferred embodiments, the treatment is by nasal administration. Further the efficacy of the treatment can be monitored by analysis of the nasal specimens.

Another aspect of the present invention is a method of providing a conclusion regarding a disease to a patient, a health care provider or a health care manager where the conclusion is based on a diagnosis, wherein the diagnosis is based on a detection of a biological substance in a nasal specimen, and wherein the biological substance is not related to a respiratory disease.

One aspect of the present invention is a method of diagnosing diabetes in a patient by obtaining a nasal specimen, detecting insulin, insulin receptor or a combination thereof in the specimen, and diagnosing the diabetes in the patient, wherein the diagnosis is based on the detection of insulin, insulin receptor or a combination thereof in the nasal specimen. Another aspect of the present invention is a method of monitoring an efficacy of a diabetes therapy in a patient by obtaining a nasal specimen, detecting insulin, insulin receptor or a combination thereof in the specimen, and determining the efficacy of the diabetes therapy, wherein the determining is based on the detection of the insulin, insulin receptor or a combination thereof in the nasal specimen.

One aspect of the present invention is a method of diagnosing cancer in a patient by obtaining a nasal specimen, detecting TNFα in the specimen, and diagnosing the cancer in the patient, wherein the diagnosis is based on the detection of TNFα in the nasal specimen. Another aspect of the present invention is a method of monitoring an efficacy of a cancer therapy by obtaining a nasal specimen, detecting TNFα in the specimen, and determining the efficacy of the cancer therapy, wherein the determining is based on the detection of TNFα in the nasal specimen. Yet another aspect of the present invention is a method of treating cancer by obtaining a nasal specimen, detecting TNFα in the specimen, and administering a drug to the patient, wherein the drug modulates the TNFα.

One aspect of the present invention is a method of diagnosing smell loss in a subject by obtaining a nasal specimen, detecting a TNFα, TRAIL, adenylyl cyclases, or carbonic anhydrase VI in the specimen, and diagnosing the smell loss in the patient, wherein the diagnosis is based on the detection of TNFα, TRAIL, adenylyl cyclases, or carbonic anhydrase VI in the nasal specimen. In some embodiments, the smell loss is hyposmia, dyosmia, or anosmia. In some embodiments, the method further comprises of treating the smell loss by administering theophylline by inhalation.

One aspect of the present invention is a method of diagnosing hepatitis in a patient by obtaining a nasal specimen, detecting antibodies against a hepatitis causing virus in the specimen, and diagnosing the hepatitis in the patient wherein the diagnosis is based on the detection of antibodies against the hepatitis causing virus in the nasal specimen. In some embodiments, the hepatitis is hepatitis A, hepatitis B, hepatitis C, hepatitis D, hepatitis E, and hepatitis G.

Another aspect of the present invention is a method of treating a disease by obtaining a nasal specimen, detecting a biological substance in the specimen, and administering a drug to the patient, wherein the drug modulates the biological substance. In some preferred embodiments, the disease is cancer and the biological substance is TNFα. In some preferred embodiments, the disease is diabetes and the biological substance is insulin or insulin receptor. In some preferred embodiments, the disease is obesity or anorexia and the biological substance is leptin, ghrelin, or agouti-related protein. In some preferred embodiments, the disease is smell loss or taste loss and the biological substance is TNFα, TRAIL, adenylyl cyclases, or carbonic anhydrase VI.

Yet another aspect of the present invention is a computer-readable medium wherein the medium comprises the result of an analysis of a biological substance, wherein the biological substances is detected from a specimen of nasal secretion and the biological substance is not related to a respiratory disease. In some embodiments, a computer-readable medium further comprises of a diagnosis of a disease. In some embodiments, at least one step in the methods of the present invention is implemented with a computer.

Yet another aspect of the present invention is a kit for a diagnosis of a disease which comprises a sterile nasal swab for collection of nasal secretions, an elongated storage and transport tube for receiving the swab wherein the tube is glass or plastic and the tube having a replaceable end closure, and containing a sterile nutrient medium for isolation of the nasal secretions, a sterile assay solution for addition to the transport tube, and a detector medium for the detection of a biological substance in the nasal secretion wherein the biological substance is not related to a respiratory disease.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
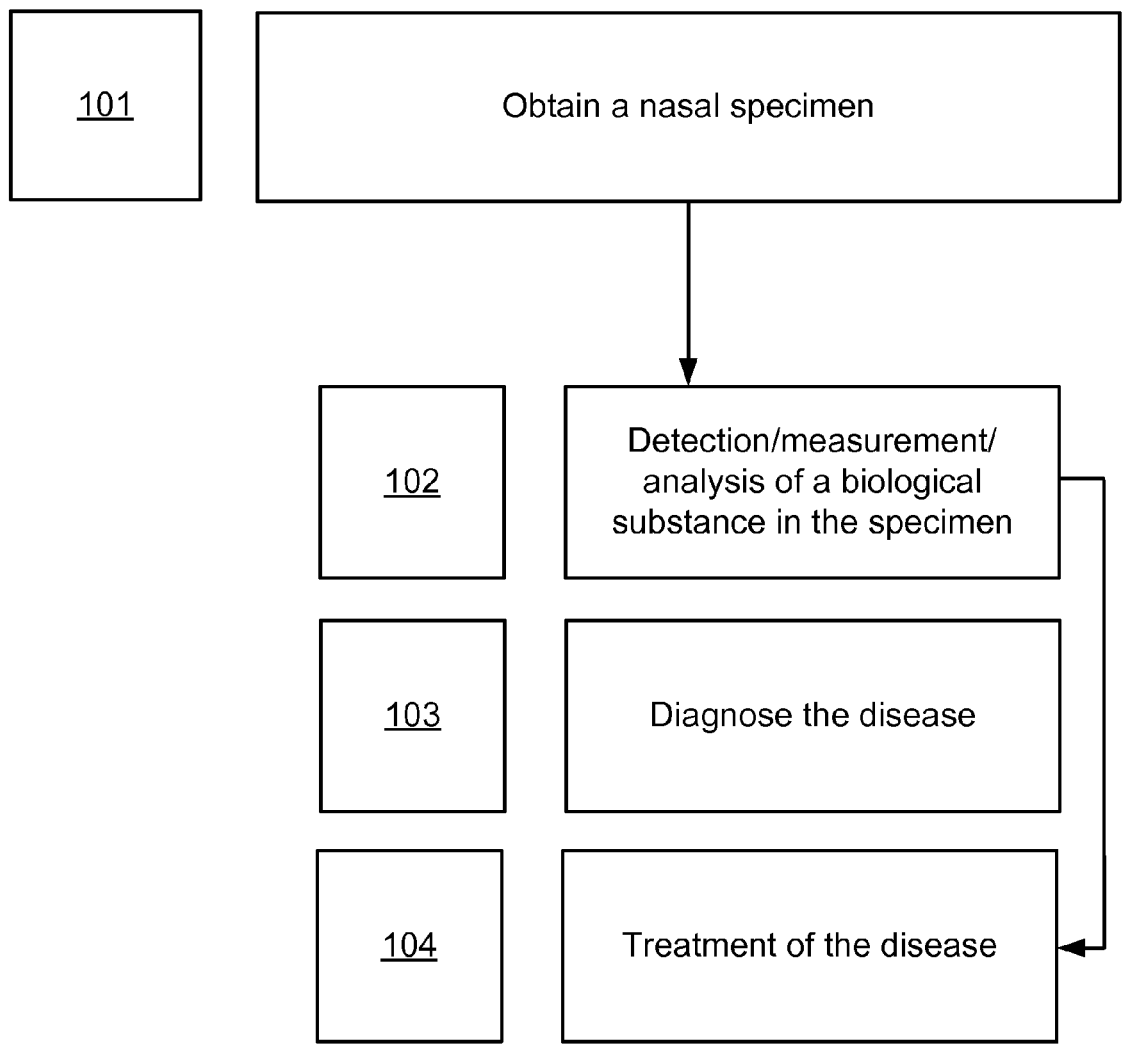
FIG. 1 is a flow chart showing the steps of the methods of the present invention.

The term "diagnosis" as used herein and its grammatical equivalents, means the testing of subjects to determine if they have a particular trait for use in a clinical decision. Diagnosis includes testing of subjects at risk of developing a particular disease resulting from infection by an infectious organism or a non infectious disease, such as cancer or a metabolic disease. Diagnosis also includes testing of subjects who have developed particular symptoms to determine the cause of the symptoms. Diagnosis also includes prognosis, monitoring progress of a disease, and monitoring the efficacy of therapeutic regimens. The result of a diagnosis can be used to classify patients into groups for performance of clinical trials for administration of certain therapies.

The term "drug" as used herein, means any compounds of any degree of complexity that perturbs a biological state, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; pesticides; herbicides; and insecticides.

The term "nucleic acid" refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. The term also refers to synthetically generated nucleic acid.

The term "pathogen" as used herein includes, viral, bacterial, fungal, prion, microbial, or other material that can be detected using the teachings of the present invention. The term "pathogen" as used herein can be natural or synthetically generated.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers. As used herein, the terms encompass amino acid chains of any length, including full length proteins (i.e., antigens), wherein the amino acid residues are linked by covalent peptide bonds. The term also refers to synthetically generated polypeptide, peptide or protein.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

METHODS OF THE INVENTION

The present invention includes methods of analyzing samples from the nose for the detection of biological substances. In particular, nasal secretion or nasal mucus is collected and analyzed for biological substances. The results of this analysis are then suitable for use in diagnosis, prognosis, and determination of suitability of therapeutic interventions. The techniques of the present invention allow for detection of biological substances that are typically not considered to be present in the nasal area, but are known to be present in other biological fluids such as blood, serum, plasma, etc. Use of nasal specimens provides a minimally invasive manner of obtaining biological samples for analysis. Also, the techniques are used to detect substances that are not present in other biological fluids such as blood, serum, plasma, etc., but have been now detected in the nasal area.

The term "biological substance" as used herein, and its grammatical equivalents, includes cells and their extra-cellular and intra-cellular constituents. For example, biological substances include pathogens, metabolites, DNA, RNA, lipids, proteins, carbohydrates, receptors, enzymes, hormones, growth factors, growth inhibitory factors, cells, organs, tissues, portions of cells, tissues, or organs, subcellular organelles, chemically reactive molecules like $H^+$, superoxides, ATP, citric acid, protein albumin, as well as combinations or aggregate representations of these types of biological variables. In addition, biological substances can include therapeutic agents such as methotrexate, steroids, non-steroidal anti-inflammatory drugs, soluble TNF-alpha receptor, TNF-alpha antibody, and interleukin-1 receptor antagonists.

A first aspect of the present invention is a method of detecting a biological substance in a nasal specimen, wherein the biological substance is not related to a respiratory disease caused by a pathogen. Respiratory diseases caused by pathogens include upper respiratory tract viral infection, upper respiratory tract bacterial infection, bacterial sinusitis, and whooping cough. However, in some embodiments, the methods of the present invention are suitable for detection of substances related to respiratory diseases that are not caused by pathogens, such as allergic rhinitis, asthma, and chronic obstructive pulmonary disease. It is understood that although some of these diseases are not caused by pathogens, they can be triggered or worsened by pathogens.

A second aspect of the invention is a method of diagnosing a disease by analyzing a nasal specimen for a biological substance that is not related to a respiratory disease. The results of this analysis can then be used for diagnosis, prognosis, and determination of suitability of therapeutic interventions.

The biological substances that can be detected by the methods of the present invention include, but are not limited to, insulin, insulin receptors, leptin, agouti-related protein, ghrelin, glucose, caspases, adenylyl cyclases, carbonic anhydrases, TNF α, TNFR I, TNFR II, TRAIL, IL3, endostatin, erythropoetin, bone morphogenic protein, brain derived neurotrophic factor, ciliary neurotrophic factor, granulocyte macrophage growth factor, hepatocyte growth factor, platelet derived growth factor, carbonic anhydrase VI, cAMP, cGMP, nitric oxide, insulin like growth factor, and endoglin.

One embodiment of the invention is the detection of substances related to glucose metabolism such as insulin and insulin receptors. The detection of insulin, insulin receptors, and glucose is used in the diagnosis insulin resistance related conditions, such as diabetes. Use of nasal specimens for the detection of glucose and insulin provides a minimally invasive technique for diagnosis of diabetes and managing diabetes care, in contrast to the invasive techniques such as venipucture.

Another embodiment of the invention is the detection of TNFα in nasal specimens. Elevated levels of TNFα have been shown to play a role in diverse disease processes. TNFα in nasal mucus was found to be about 30 times higher than in saliva. The concentration of TNFα in nasal specimens, thus, can be reflective of underlying disease processes. This detection is used in the diagnosis of various cancers and inflammatory diseases. Also, TNFα level monitoring in nasal specimens can be used to monitor the efficacy of cancer and inflammatory disease therapeutics. Further, nasal administration of anti-TNFα drugs provides a means for treatment of diseases in which TNFα plays a role. Also, levels of TNFα in nasal specimens can be used to study apoptosis.

Yet another embodiment of the invention is the detection of leptin, ghrelin and agouti-related protein in nasal specimens. Also, the methods include the administration of substances that modulate leptin, ghrelin and agouti-related protein for the control of appetite and treatment of obesity and anorexia. Nasal administration of leptin can inhibit appetite and nasal administration of agouti-related protein can stimulate appetite. Antibodies to leptin, ghrelin and agouti-related protein can be administered intranasally to modulate appetite. This modulation includes control and/or stimulation.

In some embodiments, the methods of the present invention include detecting cAMP and cGMP in nasal specimens. Comparison of the measurement of cAMP and cGMP in normal subjects with patients with taste and smell loss indicated that patients with taste and smell loss had decreased levels of cAMP in their nasal mucus. Hence, cAMP in nasal mucus can be an index of smell loss. The detection of cAMP and cGMP in the nasal mucus provides a non-invasive method for the detection of taste and smell loss in a subject.

A third aspect of the invention is a method of treating a disease wherein the treatment is based on the diagnosis of the disease by analyzing a nasal specimen for a biological substance that is not related to a respiratory disease. Preferably, following the diagnosis, a therapeutic is administered which modulates the biological specimen. In some embodiments, the treatment includes nasal administration of biological substances, such as, by way of example only, leptin, ghrelin, agouti-related protein, TNFα, insulin, or hormones. In some embodiments, the treatment includes nasal administration of therapeutic that modulates the identified biological substances.

In one embodiment for treating diabetes and/or insulin resistance, following detection of insulin, insulin receptor and/or glucose, a drug that modulates the insulin, insulin receptor and/or glucose is administered. Preferably, this administration is via nose. The drug can include antidiabetic drugs, including insulin. In one embodiment for treating cancer, following detection of TNFα, p53 or mutated p53, a drug that modulates the TNFα, p53 or mutated p53 is administered. Preferably, this administration is via nose. The drug can include anticancer drugs. In one embodiment for treating leprosy, following detection of antibodies against *mycobacterium leprae*, an antibiotic drug is administered. Preferably, this administration is via nose. In one embodiment for treating hepatitis, including hepatitis A, B, C, D, E and G, following detection of antibodies against hepatitis causing virus, a drug, such as, by way of example only, interferon is administered. Preferably, this administration is via nose. In one embodiment for treating obesity, following detection of leptin or agouti-related protein, a drug that modulates the leptin or agouti-related protein is administered. Preferably, this administration is via nose. The drug can include anti-agouti-related protein or leptin. In one embodiment for treating anorexia, following detection of leptin or agouti-related protein, a drug that modulates the leptin or agouti-related protein is administered. Preferably, this administration is via nose. The drug can include anti-leptin or agouti-related protein. In one embodiment for treating smell loss or taste loss, following detection of TNFα, CA VI, or TRAIL, a drug that modulates the TNFα, CA VI, or TRAIL is administered. Preferably, this administration is via nose. The drug can include theophylline or other drugs known in the art. In one embodiment for treating flu, following detection of flu causing pathogen or antibodies against flu causing pathogen, a drug that modulates the infection is administered. Preferably, this administration is via nose. The drug can include antibiotics or other drugs known in the art.

The biological substances in the body interact with the brain via a feedback mechanism. The biological substances present in the nose are secreted by glands that are controlled by a brain function and via the feedback mechanism, these biological substances after secretion, in turn affect the brain function. The nasal administration of the biological substance after diagnosing the disease by detecting the biological substance in the nasal secretion may be reflective of this feedback mechanism.

In some embodiments, the treatment includes transcranial magnetic stimulation (TCMS). TCMS or rTCMS (repetitive TCMS) can induce secretion of biological substances in the body, thereby inducing clinical changes. The patients suffering from loss of taste and/or smell (hypogeusia and/or hyposmia, respectively) when treated with rTCMS, showed improvement in their sensory acuity and decrease in their sensory distortions. Some biological substances in these patients, such as, CA I, II and VI, zinc, and copper were found to be significantly higher in blood plasma, erythrocytes and saliva after treatment with TCMS. The increase of the biological substances in the body after TCMS indicates that TCMS induces biochemical changes in the body and can be used to treat various diseases including clinical abnormalities of sensory function and neurological disorders.

The methods of the present invention disclosed herein include methods for detecting, diagnosing, and treating a disease in a subject, by analyzing one or more biological substances in nasal tissue or secretion. The steps of the methods of the present invention are depicted in FIG. 1. Without limiting the scope of the present invention, the steps can be performed independent of each other or one after the other.

One or more steps may be skipped in the methods of the present invention. A sample of nasal secretion is collected from a subject at step 101. One or more biological substances in the specimen is detected, measured and/or analyzed at step 102 by detection techniques known in the art, such as, PCR, mass spectrometry, protein assays etc. By way of example only some of the detection techniques are disclosed herein. A disease is diagnosed at step 103 based on the detection, measurement and/or analysis of the biological substance. A decision regarding treatment of the disease is made at step 104, the treatment decision being made based on the diagnosis.

The identification of the biological substances may involve one or more comparisons with reference specimens. The reference specimen may be obtained from the same subject or from a different subject who is either not affected with the disease or is a patient. The reference specimen could be obtained from one subject, multiple subjects or be synthetically generated. The identification may also involve the comparison of the identification data with the databases to identify the biological substance.

The steps of the methods of the present invention are provided herein. Without limiting the scope of the present invention, other techniques for collection of sample, detection of the biological substances and diagnosis of the disease are known in the art and are within the scope of the present invention.

Sample Collection

In the sample collection step, specimens from the nasal area are collected for analysis. In some embodiments of the invention, a sample of nasal secretions is collected directly from the nose into a collection tube or device. In other embodiments of the invention, a sample of nasal secretion is collected on a sample collection device by passing it into the nostril of a patient. The device may be inserted sequentially into each nostril of the patient and advanced parallel to the hard palate with slow rotation. The device is then typically transferred to a transport tube, such as a glass or plastic test tube. The transport tube may include a suitable volume of a sterile medium such as ethanol or the like.

Suitable sample collection devices are well known to those skilled in the art. Preferably, a sample collection device can be a swab, a wooden spatula, bibulous materials such as a cotton ball, filter, or gauze pad, an absorbent-tipped applicator, capillary tube, and a pipette. Preferably, a swab can be used as a sample collection device, and the sample processing element comprises a swab holder or a swab processing insert. The swab holder or swab processing insert can be tapered or angled to allow a single sample processing element to accommodate all types of swabs by allowing swabs with different amounts of fiber, or that are wound to different levels of tightness, to be held securely within the holder or insert. Most preferably, the swab holder or swab processing insert securely holds the swab to provide stability.

In some instances, samples may be collected from individuals repeatedly over a longitudinal period of time (e.g., once a day, once a week, once a month, biannually or annually). Obtaining numerous samples from an individual over a period of time can be used to verify results from earlier detections and/or to identify an alteration as a result of, for example, drug treatment. Samples can be obtained from humans or non-humans. Preferably, samples are obtained from humans.

Analysis

In the present invention, a specimen of nasal mucus, secretion, or tissue is collected and analyzed using one or more analytical techniques including enzymatic technique, ELISA, fluorometric technique, mass spectrography, HPLC, GLC, PCR, and other similar techniques. The present invention also includes methods of diagnosing a disease by analyzing nucleic acids in a nasal specimen by nucleic acid detection methods such as, but are not limited to polymerase chain reaction (PCR), ligase chain reaction (LCR), strand displacement amplification (SDA), self-sustained sequence replication (3SR), array based tests, and TAQMAN. A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159.

Polymerase Chain Reaction (PCR)

The polymerase chain reaction (PCR) is a process for amplifying one or more desired specific nucleic acid sequences found in a nucleic acid. Because large amounts of a specific sequence may be produced by this process, it is used for improving the efficiency of cloning DNA or messenger RNA and for amplifying a target sequence to facilitate detection thereof.

PCR involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction would be a discrete nucleic acid duplex with termini corresponding to the ends of the specific primers employed.

Any source of nucleic acid, in purified or non purified form, can be utilized as the starting nucleic acid or acids, provided it contains or is suspected of containing the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acid produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, it is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells.

It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be 100% homologous with the end of the desired sequence to be amplified.

An appropriate agent may be added for inducing or catalyzing the primer extension reaction and the reaction is allowed to occur under conditions known in the art. The inducing agent may be any compound or system which will function to accomplish the synthesis of primer extension products, including enzymes. Suitable enzymes for this purpose may include, for example, $E.$ $coli$ DNA polymerase I, Klenow fragment of $E.$ $coli$ DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis can be initiated at the 3' end of each primer and proceed in the 5' direction along the template strand, until synthesis terminates, producing molecules of different lengths. There may be inducing agents, however, which initiate synthesis at the 5' end and proceed in the other direction, using the same process as described above.

The newly synthesized strand and its complementary nucleic acid strand form a double-stranded molecule which can be used in the succeeding steps of the process. In the next step, the strands of the double-stranded molecule may be separated to provide single-stranded molecules. New nucleic acid may be synthesized on the single-stranded molecules. Additional inducing agent, nucleotides and primers may be added if necessary for the reaction to proceed under the conditions prescribed above. Again, the synthesis would be initiated at one end of the oligonucleotide primers and would proceed along the single strands of the template to produce additional nucleic acid. After this step, half of the extension product would consist of the specific nucleic acid sequence bounded by the two primers. The steps of strand separation and extension product synthesis can be repeated as often as needed to produce the desired quantity of the specific nucleic acid sequence. The amount of the specific nucleic acid sequence produced would accumulate in an exponential fashion. After the appropriate length of time has passed to produce the desired amount of the specific nucleic acid sequence, the reaction may be halted by inactivating the enzymes in any known manner or separating the components of the reaction.

Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed but where rapid detection is desirable.

Any known techniques for nucleic acid (e.g., DNA and RNA) amplification can be used with the assays described herein. Preferred amplification techniques are the polymerase chain reaction (PCR) methodologies which comprise solution PCR and in situ PCR.

The invention is not limited to the use of straightforward PCR. A system of nested primers may be used for example. Other suitable amplification methods known in the field can also be applied such as, but not limited to, ligase chain reaction (LCR), strand displacement amplification (SDA), self-sustained sequence replication (3SR), array based test, and TAQMAN.

As used herein "amplification" may refer to any in vitro method for increasing the number of copies of a nucleic acid sequence with the use of a DNA polymerase. Nucleic acid amplification results in the incorporation of nucleotides into a DNA molecule or primer thereby forming a new DNA molecule complementary to a DNA template. The newly formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5-100 "cycles" of denaturation, annealing, and synthesis of a DNA molecule.

Fluorescence Microscopy

Some embodiments of the invention include fluorescence microscopy for a detection of a biological substance in a nasal specimen. Fluorescence microscopy enables the molecular composition of the structures being observed to be identified through the use of fluorescently-labeled probes of high chemical specificity such as antibodies. It can be done by directly conjugating a fluorophore to a protein and introducing this back into a cell. Fluorescent analogue may behave like the native protein and can therefore serve to reveal the distribution and behavior of this protein in the cell. Along with NMR, infrared spectroscopy, circular dichroism and other techniques, protein intrinsic fluorescence decay and its associated observation of fluorescence anisotropy, collisional quenching and resonance energy transfer are techniques for protein detection.

The naturally fluorescent proteins can be used as fluorescent probes. The jellyfish *aequorea victoria* produces a naturally fluorescent protein known as green fluorescent protein (GFP). The fusion of these fluorescent probes to a target protein enables visualization by fluorescence microscopy and quantification by flow cytometry. Without limiting the scope of the present invention, some of the probes are as following:

Labels:

Sensitivity and safety (compared to radioactive methods) of fluorescence has led to an increasing use for specific labeling of nucleic acids, proteins and other biomolecules. Besides fluorescein, other fluorescent labels cover the whole range from 400 to 820 nm. By way of example only, some of the labels are, fluorescein and its derivatives, carboxyfluoresceins, rhodamines and their derivatives, atto labels, fluorescent red and fluorescent orange: Cy3/Cy5 alternatives, lanthanide complexes with long lifetimes, long wavelength labels—up to 800 nm, DY cyanine labels, and phycobili proteins.

Conjugates:

Antibody conjugates can be generated with specificity for virtually any epitope and are therefore, applicable to imaging a wide range of biomolecules. By way of example only, some of the conjugates are, isothiocyanate conjugates, streptavidin conjugates, and biotin conjugates.

Enzyme Substrates:

By way of example only, some of the enzyme substrates are fluorogenic and chromogenic substrates.

Micro- and Nanoparticles:

By way of example only, some of the fluorochromes are: FITC (green fluorescence, excitation/emission=506/529 nm), rhodamine B (orange fluorescence, excitation/emission=560/584 nm), and nile blue A (red fluorescence, excitation/emission=636/686 nm). Fluorescent nanoparticles can be used for various types of immunoassays. Fluorescent nanoparticles are based on different materials, such as, polyacrylonitrile, and polystyrene etc.

Molecular Rotors:

Fluorescent molecular rotors are sensors of microenvironmental restriction that become fluorescent when their rotation is constrained. Few examples of molecular constraint include increased dye (aggregation), binding to antibodies, or being trapped in the polymerization of actin.

IEF-Markers:

IEF (isoelectric focusing) is an analytical tool for the separation of ampholytes, mainly proteins. An advantage for IEF-Gel electrophoresis with fluorescent IEF-marker is the possibility to directly observe the formation of gradient. Fluorescent IEF-marker can also be detected by UV-absorption at 280 nm (20° C.).

Any or all of these fluorescent probes can be used for the detection of biological substances in the nasal mucus. A peptide library can be synthesized on solid supports and, by using coloring receptors, subsequent dyed solid supports can be selected one by one. If receptors cannot indicate any color, their binding antibodies can be dyed. The method can not only be used on protein receptors, but also on screening binding ligands of synthesized artificial receptors and screening new metal binding ligands as well. Automated methods for HTS and FACS (fluorescence activated cell sorter) can also be used. A FACS machine originally runs cells through a capillary tube and separate cells by detecting their fluorescent intensities.

Immunoassays

Some embodiments of the invention include immunoassay for a detection of a biological substance in a nasal specimen. In immunoblotting like the western blot of electrophoretically separated proteins a single protein can be identified by its antibody. Immunoassay can be competitive binding immunoassay where analyte competes with a labeled antigen for a limited pool of antibody molecules (e.g. radioimmunoassay, EMIT). Immunoassay can be noncompetitive where antibody is present in excess and is labeled. As analyte antigen complex is increased, the amount of labeled antibody-antigen complex may also increase (e.g. ELISA). Antibodies can be polyclonal if produced by antigen injection into an experimental animal, or monoclonal if produced by cell fusion and cell culture techniques. In immunoassay, the antibody may serve as a specific reagent for the analyte antigen.

Without limiting the scope and content of the present invention, some of the types of immunoassays are, by way of example only, RIAs (radioimmunoassay), enzyme immunoassays like ELISA (enzyme-linked immunosorbent assay), EMIT (enzyme multiplied immunoassay technique), microparticle enzyme immunoassay (MEIA), LIA (luminescent immunoassay), and FIA (fluorescent immunoassay). These techniques can be used to detect biological substances in the nasal specimen. The antibodies—either used as primary or secondary ones—can be labeled with radioisotopes (e.g. 125I), fluorescent dyes (e.g. FITC) or enzymes (e.g. HRP or AP) which may catalyse fluorogenic or luminogenic reactions.

EMIT (Enzyme Multiplied Immunoassay Technique):

EMIT is a competitive binding immunoassay that avoids the usual separation step. A type of immunoassay in which the protein is labeled with an enzyme, and the enzyme-protein-antibody complex is enzymatically inactive, allowing quantitation of unlabelled protein.

ELISA (Enzyme Linked Immunosorbent Assay):

Some embodiments of the invention include ELISA to detect biological substances in the nasal specimen. ELISA is based on selective antibodies attached to solid supports combined with enzyme reactions to produce systems capable of detecting low levels of proteins. It is also known as enzyme immunoassay or EIA. The protein is detected by antibodies that have been made against it, that is, for which it is the antigen. Monoclonal antibodies are often used.

The test may require the antibodies to be fixed to a solid surface, such as the inner surface of a test tube, and a preparation of the same antibodies coupled to an enzyme. The enzyme may be one (e.g., β-galactosidase) that produces a colored product from a colorless substrate. The test, for example, may be performed by filling the tube with the antigen solution (e.g., protein) to be assayed. Any antigen molecules present may bind to the immobilized antibody molecules. The antibody-enzyme conjugate may be added to the reaction mixture. The antibody part of the conjugate binds to any antigen molecules that were bound previously, creating an antibody-antigen-antibody "sandwich". After washing away any unbound conjugate, the substrate solution may be added. After a set interval, the reaction is stopped (e.g., by adding 1 N NaOH) and the concentration of colored product formed is measured in a spectrophotometer. The intensity of color is proportional to the concentration of bound antigen.

ELISA can also be adapted to measure the concentration of antibodies, in which case, the wells are coated with the appropriate antigen. The solution (e.g., serum) containing antibody may be added. After it has had time to bind to the immobilized antigen, an enzyme-conjugated anti-immunoglobulin may be added, consisting of an antibody against the antibodies being tested for. After washing away unreacted reagent, the substrate may be added. The intensity of the color produced is proportional to the amount of enzyme-labeled antibodies bound (and thus to the concentration of the antibodies being assayed).

Radioimmunoassay:

Some embodiments of the invention include radioimmunoassays to detect biological substances in the nasal specimen. Radioactive isotopes can be used to study in vivo metabolism, distribution, and binding of small amount of compounds. Radioactive isotopes of $^1H$, $^{12}C$, $^{31}P$, $^{32}S$ and $^{127}I$ in body are used such as $^3H$, $^{14}C$, $^{32}P$, $^{35}S$ and $^{125}I$.

In receptor fixation method in 96 well plates, receptors may be fixed in each well by using antibody or chemical methods and radioactive labeled ligands may be added to each well to induce binding. Unbound ligands may be washed out and then the standard can be determined by quantitative analysis of radioactivity of bound ligands or that of washed-out ligands. Then, addition of screening target compounds may induce competitive binding reaction with receptors. If the compounds show higher affinity to receptors than standard radioactive ligands, most of radioactive ligands would not bind to receptors and may be left in solution. Therefore, by analyzing quantity of bound radioactive ligands (or washed-out ligands), testing compounds' affinity to receptors can be indicated.

The filter membrane method may be needed when receptors cannot be fixed to 96 well plates or when ligand binding needs to be done in solution phase. In other words, after ligand-receptor binding reaction in solution, if the reaction solution is filtered through nitrocellulose filter paper, small molecules including ligands may go through it and only protein receptors may be left on the paper. Only ligands that strongly bound to receptors may stay on the filter paper and the relative affinity of added compounds can be identified by quantitative analysis of the standard radioactive ligands.

Fluorescence Immunoassays:

Some embodiments of the invention include fluorescence immunoassays for a detection of a biological substance in a nasal specimen. Fluorescence based immunological methods are based upon the competitive binding of labeled ligands versus unlabeled ones on highly specific receptor sites.

The fluorescence technique can be used for immunoassays based on changes in fluorescence lifetime with changing analyte concentration. This technique may work with short lifetime dyes like fluorescein isothiocyanate (FITC) (the donor) whose fluorescence may be quenched by energy transfer to eosin (the acceptor). A number of photoluminescent compounds may be used, such as cyanines, oxazines, thiazines, porphyrins, phthalocyanines, fluorescent infrared-emitting polynuclear aromatic hydrocarbons, phycobiliproteins, squaraines and organo-metallic complexes, hydrocarbons and azo dyes.

Fluorescence based immunological methods can be, for example, heterogenous or homogenous. Heterogenous immunoassays comprise physical separation of bound from free labeled analyte. The analyte or antibody may be attached to a solid surface. The technique can be competitive (for a higher selectivity) or noncompetitive (for a higher sensitivity). Detection can be direct (only one type of antibody used) or indirect (a second type of antibody is used). Homogenous immunoassays comprise no physical separation. Double-antibody fluorophore-labeled antigen participates in an equilibrium reaction with antibodies directed against both the antigen and the fluorophore. Labeled and unlabeled antigen may compete for a limited number of anti-antigen antibodies.

Some of the fluorescence immunoassay methods include simple fluorescence labeling method, fluorescence resonance energy transfer (FRET), time resolved fluorescence (TRF), and scanning probe microscopy (SPM). The simple fluorescence labeling method method can be used for receptor-ligand binding, enzymatic activity by using pertinent fluorescence, and as a fluorescent indicator of various in vivo physiological changes such as pH, ion concentration, and electric pressure. TRF is a method that selectively measures fluorescence of the lanthanide series after the emission of other fluorescent molecules is finished. TRF can be used with FRET and the lanthanide series can become donors or acceptors. In scanning probe microscopy, in the capture phase, for example, at least one monoclonal antibody is adhered to a solid phase and a scanning probe microscope is utilized to detect antigen/antibody complexes which may be present on the surface of the solid phase. The use of scanning tunneling microscopy eliminates the need for labels which normally is utilized in many immunoassay systems to detect antigen/antibody complexes.

Nuclear Magnetic Resonanace (NMR)

Some embodiments of the invention include NMR for detection of a biological substance in a nasal specimen. NMR spectroscopy is capable of determining the structures of biological macromolecules like proteins and nucleic acids at atomic resolution. In addition, it is possible to study time dependent phenomena with NMR, such as intramolecular dynamics in macromolecules, reaction kinetics, molecular recognition or protein folding. Heteronuclei like $^{15}N$, $^{13}C$ and $^2H$, can be incorporated in proteins by uniform or selective isotopic labeling. Additionally, some new information about structure and dynamics of macromolecules can be determined with these methods.

X-Ray Crystallography

Some embodiments of the invention include X-ray crystallography for detection of a biological substance in a nasal specimen. X-ray crystallography is a technique in which the pattern produced by the diffraction of X-rays through the closely spaced lattice of atoms in a crystal is recorded and then analyzed to reveal the nature of that lattice. This generally leads to an understanding of the material and molecular structure of a substance. The spacings in the crystal lattice can be determined using Bragg's law. X-ray diffraction is commonly carried out using single crystals of a material, but if these are not available, microcrystalline powdered samples may also be used which may require different equipment.

Fluorescence Spectroscopy

Some embodiments of the invention include fluorescence spectroscopy for detection of a biological substance in a nasal specimen. By way of example only, conventional fluorometry is measurement of emission light intensities at defined wavelengths for a certain emission maxima of a fluorophore. Total fluorometry is a collection of data for a continuum of absorption as well as emission wavelengths. Fluorescence polarization is when polarized light is used for excitation and binding of fluorochrome-labeled antigens to specific antibodies. Line narrowing spectroscopy is low-temperature solid-state spectroscopy that derives its selectivity from the narrow-line emission spectra.

Time-dependent fluorescence spectroscopy comprises time-resolved measurements containing more information than steady-state measurements, since the steady-state values represent the time average of time-resolved determinations. It is a single photon timing technique where the time between an excitation light pulse and the first photon emitted by the sample is measured.

Matrix Assisted Laser Desorption Ionization Time-of-Flight Mass Spectrometry (MALDI TOF-MS)

Some embodiments of the invention include MALDI TOF-MS for detection of a biological substance in a nasal specimen. MALDI TOF-MS provides accurate mass determinations and primary sequence information. Improved mass resolution in MALDI TOF-MS can be obtained by the utilization of a single-stage or a dual-stage reflectron (RETOF-MS). In the reflectron mass spectrum, the isotopic multiplet is well resolved producing a full width half maximum (FWHM) mass resolution of about 3400. Mass resolutions up to 6000 (FWHM) can be obtained for peptides up to about 3000 Da with RETOF-MS. Enhancing the mass resolution can also increase the mass accuracy when determining the ion's mass.

Both linear and reflectron MALDI-TOF-MS can be utilized for molecular weight determinations of molecular ions and enzymatic digests leading to structural information of proteins. These digests are typically mass analyzed with or without purification prior to molecular weight determinations. Varieties of methodologies have been developed to obtain primary sequence information for proteins and peptides utilizing MALDI TOF-MS. Two different approaches can be taken. The first method is known as protein ladder sequencing and can be employed to produce structurally informative fragments of the analyte prior to insertion into the TOF mass spectrometer and subsequent analysis. The second approach utilizes the phenomenon of metastable ion decay that occurs inside the TOF mass spectrometer to produce sequence information.

The ladder sequencing with TOF-MS consists of either a time-dependent or concentration-dependent chemical degradation from either the N- or C-terminus of the protein/peptide into fragments, each of which differs by one amino acid residue. The mixture is mass analyzed in a single MALDI-TOF-MS experiment with mass differences between adjacent mass spectral peaks corresponding to a specific amino acid residue. The order of occurrence in the mass spectrum defines the sequence of amino acids in the original protein/peptide.

Post-source decay with RETOF-MS MALDI is an ionization technique that produces intact protonated pseudomolecular ion species. A significant degree of metastable ion decay occurs after ion acceleration and prior to detection. The ion fragments produced from the metastable ion decay of peptides and proteins typically include both neutral molecule losses (such as water, ammonia and portions of the amino acid side chains) and random cleavage at peptide bonds. In-source decay with linear TOF-MS is an alternative approach to RETOF-MS for studying metastable ion decay of MALDI generated ions. Primary structural information for peptides and proteins can be obtained by this method. Coherent mass spectral peaks can be produced from these metastable decayed ions giving rise to significant structural information for peptides and proteins.

Surface-Enhanced Laser Desorption Ionization-Time of Flight (SELDI-TOF)

Some embodiments of the invention include SELDI TOF-MS for detection of a biological substance in a nasal specimen. This technique utilizes stainless steel or aluminum-based supports, or chips, engineered with chemical (hydrophilic, hydrophobic, pre-activated, normal-phase, immobilized metal affinity, and cationic or anionic) or biological (antibody, antigen binding fragments (e.g. scFv), DNA, enzyme, or receptor) bait surfaces of 1-2 mm in diameter. These varied chemical and biochemical surfaces allow differential capture of proteins based on the intrinsic properties of the proteins themselves. Solubilized tissue or body fluids in volumes as small as 0.1 µA can be directly applied to these surfaces, where proteins with affinities to the bait surface may bind. Following a series of washes to remove non-specifically or weakly bound proteins, the bound proteins are laser desorbed and ionized for MS analysis. Masses of proteins ranging from small peptides of less than 1000 Da up to proteins of greater than 300 kDa can be calculated based on time-of-flight. As mixtures of proteins may be analyzed within different samples, a unique sample fingerprint or signature may result for each sample tested. Consequently, patterns of masses rather than actual protein identifications can be produced by SELDI analysis. These mass spectral patterns can be used to differentiate patient samples from one another, such as diseased from normal.

UV-Vis

Some embodiments of the invention include optical absorption spectroscopy (UV/VIS) for detection of a biological substance in a nasal specimen. UV/VIS provides light absorption data which helps in the determination of concentration of macromolecules such as, proteins, DNA, nucleotides etc. Organic dyes can be used to enhance the absorption and to shift the absorption into the visible range (e.g. coomassie blue reagents). Resonance raman spectroscopy (RRS) can be used to study molecular structure and dynamics. RRS helps in investigating specific parts of macromolecules by using different excitation wavelengths.

Liquid Chromatography (LC)

Some embodiments of the invention include LC for a detection of biological substance in a nasal specimen. Examples of LC are but not limited to, affinity chromatography, gel filtration chromatography, anion exchange chromatography, cation exchange chromatography, diode array-LC and high performance liquid chromatography (HPLC).

Gel filtration chromatography separates proteins, peptides, and oligonucleotides on the basis of size. Molecules may move through a bed of porous beads, diffusing into the beads to greater or lesser degrees. Smaller molecules may diffuse further into the pores of the beads and therefore move through the bed more slowly, while larger molecules may enter less or not at all and thus move through the bed more quickly. Both molecular weight and three dimensional shapes contribute to the degree of retention. Gel Filtration Chromatography may be used for analysis of molecular size, for separations of components in a mixture, or for salt removal or buffer exchange from a preparation of macromolecules.

Affinity chromatography is the process of bioselective adsorption and subsequent recovery of a compound from an immobilized ligand. This process allows for the specific and efficient purification of many diverse proteins and other compounds. Ion exchange chromatography separates molecules based on differences between the overall charges of the proteins. It can be used for the purification of protein, oligonucleotides, peptides, or other charged molecules.

HPLC can be used in the separation, purification and detection of biological substances in the nasal mucus. Crude tissue extracts may be loaded directly onto the HPLC system and mobilized by gradient elution. Rechromatography under the identical conditions is an option if further purification is warranted or necessary. Reversed phase chromatography (RPC) can be utilized in the process of protein structure determination. HPLC may be coupled with MS. The HPLC method described in Henkin et al., *New Frontiers in Immunobiology,* 2000, pp. 127-152, is incorporated herein in its entirety.

The size-exclusion chromatography (SEC) and ion-exchange chromatography (IEC) can be used for separation and purification of biologically active proteins, such as enzymes, hormones, and antibodies. In liquid affinity chromatography (LAC), interaction may be based on binding of the protein due to mimicry of substrate, receptor, etc. The protein may be eluted by introducing a competitive binding agent or altering the protein configuration which may facilitate dissociation. A procedure that can be used in the separation of membrane proteins is the use of nonionic detergents, such as Triton X-100, or protein solubilization by organic solvents with IEC.

Diode array detector-liquid chromatography (DAD-LC) provides complete, multiple spectra for each HPLC peak, which, by comparison, can provide indication of peak purity. These data can also assign presence of tyr, trp, phe, and possibly others (his, met, cys) and can quantitate these amino acids by 2nd derivative or multi-component analysis. By a post-column derivatization, DAD-LC can also identify and quantitate cys, his and arg in individual peptides. Thus, it is possible to analyze for 6 of the 20 amino acids of each separated peptide in a single LC run, and information can be obtained about presence or absence of these amino acids in a given peptide in a single step. This is assisted by knowing the number of residues in each peptide.

Electrophoresis

Some embodiments of the invention include electrophoresis for detection of a biological substance in a nasal specimen. Electrophoresis can be gel electrophoresis or capillary electrophoresis.

Gel Electrophoresis:

Gel electrophoresis is a technique that can be used for the separation of proteins. During electrophoresis, macromolecules are forced to move through pores when an electrical current is applied. Their rate of migration through the electric field depends on strength of the field, size and shape of the molecules, relative hydrophobicity of the samples, and on an ionic strength and temperature of a buffer in which the molecules are moving. After staining, the separated macromolecules in each lane can be seen in a series of bands spread from one end of the gel to the other. Using this technology it is possible to separate and identify protein molecules that differ by as little as a single amino acid. Also, gel electrophoresis allows determination of crucial properties of a protein such as its isoelectric point and approximate molecular weight. Electrofocusing or isoelectric focusing is a technique for separating different molecules by their electric charge differences (if they have any charge). It is a type of zone electrophoresis that takes advantage of the fact that a molecule's charge changes as the pH of its surroundings changes.

Capillary Electrophoresis:

Capillary electrophoresis is a collection of a range of separation techniques which may involve the application of high voltages across buffer filled capillaries to achieve separations. The variations include separation based on size and charge differences between analytes (termed capillary zone electrophoresis (CZE) or free solution CE (FSCE)), separation of neutral compounds using surfactant micelles (micellar electrokinetic capillary chromatography (MECC) or sometimes referred to as MEKC) sieving of solutes through a gel network (capillary gel electrophoresis, GCE), separation of cations (or anions) based on electrophoretic mobility (capillary isotachophoresis, CITP), and separation of zwitterionic solutes within a pH gradient (capillary isoelectric focusing, CIEF). Capillary electrochromatography (CEC) can be an associated electrokinetic separation technique which involves applying voltages across capillaries filled with silica gel stationary phases. Separation selectivity in CEC can be a combination of both electrophoretic and chromatographic processes. Many of the CE separation techniques rely on the presence of an electrically induced flow of solution (electroosmotic flow, EOF) within the capillary to pump solutes towards the detector.

Arrays

Some embodiments of the invention include arrays for detection of a biological substance in a nasal specimen. Arrays involve performing parallel analysis of multiple samples against known protein targets. The development of various microarray platforms can enable and accelerate the determination of protein abundance, localization, and interactions in a cell or tissue. Microarrays provide a platform that allows identification of protein interaction or function against a characterized set of proteins, antibodies, or peptides. Protein-based chips array proteins on a small surface and can directly measure the levels of proteins in tissues using fluorescence-based imaging. Proteins can be arrayed on either flat solid phases or in capillary systems (microfluidic arrays), and several different proteins can be applied to these arrays. In addition to the use of antibodies as array probes, single-stranded oligonucleotides, whose specificity is optimized by in vitro elution (aptamers), offer a viable alternative. Nonspecific protein stains can be then used to detect bound proteins.

Arrays include, but are not limited to, bead arrays, bead based arrays, bioarrays, bioelectronic arrays, cDNA arrays, cell arrays, DNA arrays, gene arrays, gene expression arrays, frozen cell arrays, genome arrays, high density oligonucleotide arrays, hybridization arrays, microcantilever arrays, microelectronic arrays, multiplex DNA hybridization arrays, nanoarrays, oligonucleotide arrays, oligosaccharide arrays, planar arrays, protein arrays, solution arrays, spotted arrays, tissue arrays, exon arrays, filter arrays, macroarrays, small molecule microarrays, suspension arrays, theme arrays, tiling arrays, and transcript arrays.

Sensors

Some embodiments of the invention include sensors for detection of a biological substance in a nasal specimen. Sensors can be used for both in vivo and in vitro detection. Sensors can be chemical sensors, optical sensors, and biosensors. Chemical sensors are miniaturized analytical devices which may deliver real-time and online information on the presence of specific compounds or ions in complex samples. Optical sensors are based on measurement of either intrinsic optical properties of analytes, or of optical properties of indicator dyes or labeled biomolecules attached to solid supports.

Biosensors can be affinity biosensor based on capabilities of enzymes to convert substrates into products or catalytic biosensors. Biosensors detect antibody and analyte complexes using a variety of physical methods. Some biosensors measure the change in surface charge that occurs when analyte is bound to antibodies or other binding agents, which in turn are bound to a surface. Other biosensors use binding agents attached to a surface and measure a change in a physical property of the support, other than surface charge, upon binding of analyte. Some biosensor techniques use a specific property of a labeled binding agent or antigen to produce a measurable change.

Methods for Identifying Proteins from a Library Screen

Protein identification methods by way of example only include low-throughput sequencing through Edman degradation, mass spectrometry techniques, peptide mass fingerprinting, de novo sequencing, and antibody-based assays. The protein quantification assays include fluorescent dye gel staining, tagging or chemical modification methods (i.e. isotope-coded affinity tags (ICATS), combined fractional diagonal chromatography (COFRADIC)). The purified protein may also be used for determination of three-dimensional crystal structure, which can be used for modeling intermolecular interactions. Common methods for determining three-dimensional crystal structure include x-ray crystallography and NMR spectroscopy. Detailed below are a few of the methods for identifying proteins in the present invention.

Protein Sequencing:

N-terminal sequencing aids in the identification of unknown proteins, confirm recombinant protein identity and fidelity (reading frame, translation start point, etc.), aid the interpretation of NMR and crystallographic data, demonstrate degrees of identity between proteins, or provide data for the design of synthetic peptides for antibody generation, etc. N-terminal sequencing utilises the Edman degradative chemistry, sequentially removing amino acid residues from the N-terminus of the protein and identifying them by reverse-phase HPLC. Sensitivity can be at the level of 100 s femtomoles and long sequence reads (20-40 residues) can often be obtained from a few 10 s picomoles of starting material. Pure proteins (>90%) can generate easily interpreted data, but insufficiently purified protein mixtures may also provide useful data, subject to rigorous data interpretation. N-terminally modified (especially acetylated) proteins cannot be sequenced directly, as the absence of a free primary amino-group prevents the Edman chemistry. However, limited proteolysis of the blocked protein (e.g. using cyanogen bromide) may allow a mixture of amino acids to be generated in each cycle of the instrument, which can be subjected to database analysis in order to interpret meaningful sequence information. C-terminal sequencing is a post-translational modification, affecting the structure and activity of a protein. Various disease situations can be associated with impaired protein processing and C-terminal sequencing provides an additional tool for the investigation of protein structure and processing mechanisms.

Proteome Analyses:

Proteomics can be identified primarily by computer search algorithms that assign sequences to a set of empirically acquired mass/intensity data which are generated from conducting electrospray ionization (ESI), matrix-assisted laser desorption/ionization (MALDI-TOF), or three-dimensional quadrupole ion traps on the protein of interest.

Diagnosis

The identification and analysis of biological substances as disclosed herein has numerous therapeutic and diagnostic applications. Clinical applications include, for example, detection of disease, distinguishing disease states to inform prognosis, selection of therapy, and/or prediction of therapeutic response, disease staging, identification of disease processes, prediction of efficacy of therapy, monitoring of patients trajectories (e.g., prior to onset of disease), prediction of adverse response, monitoring of therapy associated with efficacy and toxicity, and detection of recurrence.

Measuring a concentration of the biological substance can aid in the diagnosis of a course of a disease. For example, the diabetic state of a patient who was previously diagnosed with diabetes can be determined by monitoring the nasal secretions of the patient for insulin. A biological substance, for example, growth factor may be one that is specific for the patient's specific disease. Alternatively, a panel of two or more specific or non-specific growth factors may be monitored. The concentrations of either an individual factor or several factors, in the biological sample of the patient may be affected by the disease.

The presence or increase or decrease of biological substances' concentration allows the physician or veterinarian to predict the course of the disease or the efficacy of treatment regimes. If, for example, a patient who had a certain type of disease, which was treated, subsequently exhibits an increase in the concentration of biological substances that is associated with that disease, the physician or veterinarian can predict that the patient may have progression of the disease in the future or predict a higher risk of fatality in the patient. In addition, the amount of biological substances may be predictive of the outcome of the patient, e.g., how well certain chemotherapeutic agents may act.

One aspect of the present invention is a method of diagnosing a disease by obtaining a specimen of nasal secretion, detecting a biological substance in the specimen, and diagnosing the disease wherein the diagnosis is based on the detection of the biological substance, and wherein the biological substance is not related to a respiratory disease. In one embodiment leprosy is diagnosed by detection of antibodies against leprosy causing pathogen for example, *mycobacterium leprae*. In one embodiment hepatitis, such as hepatitis A, B, C, D, E, and G, is diagnosed by detection of antibodies against hepatitis causing virus. In some embodiments, the biological substances include insulin or insulin receptors for a diagnosis of diabetes. In some embodiments, the biological substance is p53 for a diagnosis of cancer.

Some embodiments of the invention include diagnosing diabetes by detecting insulin or insulin receptor in the nasal specimen. Table 6 depicts detection and measurement of human insulin concentration in nasal mucus as compared to insulin concentration in blood plasma and saliva. Table 7 depicts the detection and measurement of human insulin receptor concentration in nasal mucus as compared to the insulin receptor concentration in plasma and saliva. The appearance of insulin or insulin receptors in nasal mucus refects either their synthesis in nasal serous glands or response to a physiological and/or pathological phenomena. The presence of insulin or insulin receptors in nasal mucus offers a non-invasive method for the diagnosis of diabetes and other disorders of carbohydrate metabolism.

Some embodiments of the invention include diagnosing cancer by detecting caspase in the nasal specimen. Cysteine-dependent aspartate-specific proteases (caspases) are a family of proteases that cleave their substrates at aspartic acid (D)-X bonds. 14 mammalian caspases have been identified. Caspase-2, -3, -6, -7, -8, -9 and -10 are major players in the execution phase of apoptosis, whereas caspase-1, -4, -5, and -11 are involved in cytokine processing associated with inflammation. Caspase 3, also known as CPP32, cleaves and activates a variety of proteins such as sterol regulatory element binding proteins (SREBPs). Caspase-3 also cleaves poly (ADP-ribose) polymerase (PARP) at the onset of apoptosis and amyloid β precursory protein (APP) which is associated with neuronal death in Alzheimer's disease. Caspase 3 is activated by graszyne β, ADAF-1, caspase 9 and caspases 6, 8 and 10. This substance is one of the apoptotic substances found during the apoptotic process. Table 10 illustrates a comparison between the detection of caspase 3 in nasal mucus as well as saliva. The presence of caspase in nasal mucus is about 13% of that in saliva and reflects the magnitude of the apoptotic process. The presence of caspase in nasal mucus indicates the activity of cellular death in nasal mucus and shows that cancer can be diagnosed by detecting caspase in the nasal specimen.

Some embodiments of the invention include diagnosing cancer, taste loss or smell loss by detecting tumor necrosis factor α (TNFα) in the nasal specimen. TNFα is a 17 KD cleavage product mediated by TNFα converting enzyme which interacts with two distinct TNFα receptors (I, II) on the cell surface. TNFα is upregulated in many pathological processes involving inflammation and oncological processes such as rheumatoid arthritis, refractory bronchial asthma, liver disease, cancer and in patients with taste and smell loss. It is also called cachectin and is produced by many normal and tumor cells in response to a wide variety of stimuli including viruses, bacteria, parasites, cytokines and mitogens. Both the transmembrane and the soluble secreted forms of TNFα are biologically active. TNFα is an extremely pleotrophic cytokine due to the ubiquity of its receptors, its ability to activate multiple signal transduction pathways and its ability to induce or suppress the expression a large number of genes.

Detecting the levels of TNFα in nasal mucus as disclosed herein makes the diagnosis of a disease possible on a clinical basis since obtaining cellular diagnosis through tissue biopsy can not only be invasive but also can be difficult and at times dangerous. Table 11 illustrates detection and measurement of TNFα in nasal mucus and saliva in 75 subjects. Results indicate that TNFα in nasal mucus is about 30 times higher than in saliva. These data suggest that various cancers can be diagnosed by measurements of TNFα in nasal mucus and their treatment can be monitored by following its concentration in nasal mucus. Since levels of TNFα may also reflect the inflammatory aspects of disease processes inducing it, use of anti TNFα drugs through nasal administration reflect a method of treating these various disease processes. Concentrations of TNFα in nasal mucus in patients with smell loss can be greater than for example, 5000 times that found in normal subjects thereby reflecting its function as a "death protein" indicator of excessive apoptosis as in its role in cancer.

Monitoring the levels of TNFα in nasal mucus may help in diagnosis of arterial venous malfunction (AVM). AVM is normally diagnosed by MRI but detection and measurement of TNFα in nasal mucus provides a non-invasive method of diagnosing AVM. Monitoring the level of TNFα can help in diagnosing the progression or stage of AVM or the susceptibility of the subject towards AVM.

Some embodiments of the invention include diagnosing cancer, taste loss or smell loss by detecting tumor necrosis factor receptor I (TNFR I) in the nasal specimen. TNF receptor I (TNFRI) is one of the two cellular receptors upon which TNFα operates. It is one of the prototypic members of the TNF receptor super family members designated TNFRSF I α. In disease processes associated with increased TNFα activity TNFR I may be upregulated. Its presence in nasal mucus can reflect the activity of many inflammatory, oncological and other pathological processes, including taste and smell dysfunction. Table 12 illustrates detection and measurement of TNFR I in 47 subjects. Results indicate that TNFR I in nasal mucus is about 16 times its concentration in saliva and its concentration is significantly increased over that found in plasma, red blood cells, or urine. Thus the detection of TNFR I in the nasal specimen can be used to establish clinical diagnoses of excessive apoptosis and can be used as a treatment modality in inhibiting pathological apoptosis.

TNFR II is the other of the two cellular receptors upon which TNFα operates. TNFR II is one of the high-affinity receptors for TNFα and is one of the prototypic members of the TNF super family members designated TNFSF Iβ. TNFR II may be upregulated in many inflammatory and oncological disease processes. It may also be solubilized and have properties similar to TNFR I. Table 13 illustrates detection and measurement of TNFR II in 47 subjects. Results indicate that TNFR II in nasal mucus is about 24 times its concentration in saliva and its concentration in nasal mucus is significantly higher than found in plasma, rbcs, or urine. The results reflect that detection of TNFR II in nasal specimen can provide a non invasive method of diagnosing various pathological processes related to TNFR II.

TNF related apoptosis-inducing ligand (TRAIL) is also known as apo-2 ligand and TNFSF-10. It is a Type II transmembrane protein with a carboxy terminal extracellular domain that exhibits homology to other TNF super family members. Among TNF super family members TRAIL is the most homologous Fas ligand, sharing 28% amino acid sequence identity in their extracellular domain. Human TRAIL shares 65% amino acid sequence identity with mouse TRAIL. TRAIL reflects the terminal protein in the apoptotic sequence. Table 14 in the examples illustrates detection and measurement of TRAIL in saliva and nasal mucus in normal subjects and in patients with smell loss. Results indicate that TRAIL in nasal mucus is about 5 times higher than in saliva and both are significantly higher than in blood, rbcs or urine. The results reflect that detection of TRAIL in nasal mucus can provide a non invasive method of diagnosing various diseases related to TRAIL. The methods of the present invention include treatment of diseases by modulating these elevated concentrations by use of anti-TRAIL drugs or agents. In some embodiments, the treatment is preferably by nasal administration.

Some embodiments of the invention include diagnosing disease by detecting interleukin in the nasal specimen. Interleukin 2 (IL2) is a T-cell growth factor that is produced by T-cells following activation by mitogins or antigens and it stimulate growth and differentiation of β cells, natural killer (NK) cells, lymphocyte killer (LAK) cells, monocytes/macrophages and oligodendrocytes. At the amino acid sequence level there can be about 50-90% homology between species. Interleukin 3 (IL 3), also known as mast cell growth factor, is a pleitrophic factor produced primarily by activated T cells. It can stimulate proliferation and differentiation of pluripotent hematopoetic stem cells as well as various lineage committed progenitors. Mature human and mouse IL 3 share about 29% amino acid sequence homology. Table 18 in the examples illustrates detection and measurement of IL 3 in both human saliva and nasal mucus. Levels of IL 3 in nasal mucus were found to be about ½ the concentration in saliva but both levels were higher than that found in plasma, rbcs or urine. IL 3 present in nasal mucus provides a non invasive method of diagnosing various diseases related to IL3. The methods of the present invention include treatment of diseases by modulating the concentration of IL3 with drugs. In some embodiments, the treatment is by nasal administration.

Some embodiments of the invention include diagnosing disease by detecting endostatin in the nasal specimen. Endostatin is a 20 KD G terminal fragment of collagen XVII. Its function is as an antiangiogenic substance or angiogenic antagonist. It is a naturally occurring protein which has been used as an anti cancer agent to inhibit blood vessel growth and spread of any form of cancer. Table 19 in the examples illustrates detection and measurement of endostatin in plasma, urine, saliva and nasal mucus in 15 subjects. Endostatin levels in nasal mucus were 5 times higher than in saliva but 7% that found in plasma. On the basis of endostatin/protein, levels of nasal mucus are about 14% that found in plasma. Presence of endostatin in nasal mucus indicates a non-invasive method of detection of endostatin in nasal mucus and its use in diagnosing various diseases. The methods of the present invention include treatment of diseases by modulating the concentration of endostatin with drugs. In some embodiments, the treatment is by nasal administration.

Some embodiments of the invention include diagnosing disease by detecting erythropoietin in the nasal specimen. Erythropoietin (EPO) is a 30 KD glycosylated protein produced primarily by the kidney. It is the principal factor that regulates erythropoesis. Production of EPO by the kidney cell is increased in response to hyposmia or anemia. The cDNA for EPO has been cloned from many species. Mature proteins from various species are highly conserved exhibiting greater than 80% amino acid sequence homology. Table 20 in the examples illustrates detection and measurement of EPO in plasma, urine, saliva and nasal mucus. EPO was not found in urine or saliva. The level of EPO in nasal mucus was found to be between 1.1 and 4.5 times higher than in plasma. Presence of EPO in nasal mucus illustrates a non-invasive method of detection of EPO in nasal mucus and its use in diagnosing various diseases. The diagnosis can further lead to treatment of disease by modulating the concentration of EPO with drugs. In some embodiments, the treatment is by nasal administration.

Some embodiments of the invention include diagnosing disease by detecting bone morphogenic protein in the nasal specimen. Bone morphogenic protein BMP I, also known as procollagen C-proteinase (PCP) is a zinc protease of the astacin family. BMP I/PCP plays a key role in formation of extracellular matrix (KCM) by connecting precursor proteins into their mature and functional form. Precursor proteins identified as substrates for BMP I/PCP include collagens, biglycan, laminin S, dentin matrix protein I and lysyl oxidase. Table 21 in the examples illustrates detection and measurement of BMP I in plasma, urine, saliva and nasal mucus in 20 subjects. BMP I was found in plasma but not in urine, saliva or nasal mucus.

Some embodiments of the invention include diagnosing disease by detecting brain-derived neurotrophic factor in the nasal specimen. Brain-derived neurotrophic factor (BDNF) is a member of the NGF family of neurotrophic factors, BDNF, NGF, NT-3 and NT 4/5. BDNF is required for differentiation and survival of specific subpopulations in both central and peripheral nervous systems. High levels of BDNF expression have been found in hippocampus, cerebellum, fetal eye and placenta. Table 22 in the examples illustrates detection and measurement of BDNF in plasma, urine, saliva and nasal mucus in 20 subjects. BDNF was found in plasma and nasal mucus but not in urine or saliva. Levels of BDNF in plasma were higher than in nasal mucus. The results indicate that nasal mucus is a repository of the family of nerve growth factors and the concentration of BDNF as shown in Table 22, may help understand both physiology and pathology of neurotrophic factors related to growth and homeostasis of cells in the nasal cavity as well as reporting on the presence of these factors in the systemic circulation. Presence of BDNF in nasal mucus illustrates a non-invasive method of detection of BDNF in nasal mucus and its use in diagnosing various diseases. The diagnosis can further lead to treatment of diseases by modulating the concentration of BDNF with drugs. In some embodiments, the treatment is by nasal administration.

Some embodiments of the invention include diagnosing disease by detecting ciliary neurotrophic factor in the nasal specimen. Ciliary neurotrophic factor (CNTF) 15 structurally related to IL-6, IL-11, L1F, CLC and OSM. CNTF is a trophic factor for embryonic chick ciliary parasympathetic neurons in culture. CNTF is also a survival factor for additional numerous cell types including dorsal root ganglion sensory neurons, sympathetic ganglion neurons, embryonic motor neurons, major pelvic ganglion neurons and hippocampal neurons. Table 23 in the examples illustrates detection and measurement of CNTF in plasma, urine, saliva and nasal mucus in 19 subjects. Levels of CNTF in plasma and nasal mucus were found to be similar but lower in saliva. Presence of CNTF in nasal mucus illustrates a non-invasive method of detection of CNTF in nasal mucus and its use in diagnosing various diseases. The diagnosis can further lead to treatment of diseases by modulating the concentration of CTNF with drugs. In some embodiments, the treatment is by nasal administration.

Some embodiments of the invention include diagnosing disease by detecting granulocyte macrophage growth factor in the nasal specimen. Granulocyte macrophage growth factor (GM-CSF) is a 22 KD mononeric hematopoetic cytokine that is characterized as a growth factor that supports the in vitro colony formation of granulocyte macrophage progenitors. It is produced by a number of different cell types including activated T cells, B cells, macrophages, mast cells, endothelial cells and fibroblasts, in response to cytokines or immune and inflammatory stimuli. GM-CSF is species specific. Table 24 in the examples illustrates detection and measurement of GM-CSF in plasma, urine, saliva and nasal mucus in 16 subjects. The results provide a non-invasive method for the detection of GM-CSF in nasal mucus. Levels in nasal mucus were found to be over 6 times that found in plasma. The detection of GM-CSF in nasal mucus provides a non invasive method of diagnosing various diseases related to GM-CTF. The methods of the present invention include treatment of diseases by modulating the concentrations of GM-CSF by use of drugs. In some embodiments, the treatment is by nasal administration.

Some embodiments of the invention include diagnosing disease by detecting hepatocyte growth factor in the nasal specimen. Hepatocyte growth factor (HGF), also known as hepatopoeitin A, is a mitogenic protein for a variety of cell types including endothelial and epithelial cells, melanocytes and keratinocytes. It is identical to scatter factor, a fibroblast-derived soluble factor that promotes the dissociation of epithelial and vascular endothelial cell colonies in monolayer cultures by stimulating cell migration. Table 25 in the examples illustrates detection and measurement of HGF in plasma, urine, saliva and nasal mucus in 17 subjects. Concentrations of HGF in nasal mucus were found to be higher than that found in either plasma or urine. These results suggest that HGF may be synthesized in the serous glands of the nose for a specific mechanism involved with nasal homeostasis as well as a mechanism involved with systemic cell migration. The results provide a non-invasive method for the detection of HGF in nasal mucus. The detection of HGF in nasal mucus provides a non invasive method of diagnosing various diseases related to human physiology and pathology. The diagnosis further leads to a treatment of diseases by modulating the concentrations of HGF by use of drugs.

Some embodiments of the invention include diagnosing disease by detecting platelet derived growth factor in the nasal specimen. Platelet derived growth factor (PDGF) family is a group of disulfide-linked dimeric proteins which act mainly on connective tissue. This family may consist of four homodimeric proteins, PDGF-AA, PDGF-BB, PDGF-CC and PDGF-DD and one heterodimeric protein, PDGF-AB. The technique of ELISA measurement used is associated with the ability of PDGF to stimulate incorporation of 3H-thymidine in quiescent NRGR-3 T 3 fibroblastis. Table 26 in the examples illustrates detection and measurement of PDGF in human plasma, urine, saliva and nasal mucus in 18 subjects. Concentrations of PDGF expressed per mg protein were found to be higher in saliva and nasal mucus than in plasma. These results suggest that PDGF may be synthesized in the serous glands of the nose for a specific mechanism involved with nasal homeostasis. The results provide a non-invasive method for the detection of PDGF in nasal mucus. The detection of PDGF in nasal mucus provides a non invasive method of diagnosing various diseases related to human physiology and pathology. The diagnosis can provide treatment of diseases by modulating the concentrations of PDGF by use of drugs.

Some embodiments of the invention include diagnosing taste loss or smell loss by detecting carbonic anhydrase in the nasal specimen. Carbonic anhydrase is a zinc-containing enzyme and at least twenty carbonic anhydrase variants, called "isozymes" have been identified. Carbonic Anhydrase VI (CA VI) is a 36 KD zinc metalloglycoprotein. Its synthesis in nasal mucus may take place in nasal serous glands (in the oral parotid glands). It can act as a taste bud growth factor in the oral cavity and as an olfactory receptor growth factor in the nasal cavity. It can also act on taste bud and olfactory receptor stem cells to induce growth and development of the entire panoply of cell types for the taste buds and olfactory epithelium. Its decreased synthesis may induce both loss of taste and smell. Its resumed synthesis may return cell growth to normal. Treatment which increases synthesis of CA VI may involve several complex processes including increasing zinc-cofactor concentration. Administration of zinc ion to some patients who are either zinc deficient or who may have metabolic processes which inhibit zinc incorporation into the protein, may have their taste and smell function improved through this treatment. Since the carbohydrates in this protein are part of its function, any process that repairs glycoprotein incorporation into this protein may also therapeutically be effective in restoring taste and smell function.

Table 27 in the examples illustrates decrease in CA VI in patients with smell and taste loss. Table 28 in the examples illustrates loss of smell function by disease etiology with respect to measurements of CA VI concentration in nasal mucus. Results indicate that patients with post influenza hyposmia hypogeusia (PIHH), allergic rhinitis and post anesthesia have significantly decreased CA VI concentrations in nasal mucus. These results provide a method for the detection and measurement of CA VI in nasal mucus as an index of smell and taste loss and its continual measurement during treatment of these disorders in order to monitor efficacy of therapy. The detection of CA VI in nasal mucus provides a non invasive method of diagnosing various diseases related to human physiology and pathology. The diagnosis can further lead to treatment of diseases by modulating the concentrations of CA VI by use of drugs Some embodiments of the invention include diagnosing a disease by detecting cAMP and cGMP in the nasal specimen. Table 29 in the examples illustrates detection and measurement of cAMP and cGMP in saliva and in nasal mucus in normal subjects. Table 30 in the examples illustrates comparison of the measurement of cAMP and cGMP in normal subjects with the patients with taste and smell loss. Results indicated that patients with smell loss had decreased levels of cAMP in their nasal mucus. These results indicate that cAMP in nasal mucus can be an index of smell loss and that its secretion may be inhibited in smell loss. The results provide a non-invasive method for the detection of cAMP and cGMP in nasal mucus.

Table 31 in the examples illustrates detection and measurement of cAMP and cGMP secretion in nasal mucus in patients with graded severity of smell loss (anosmia<Type I hyposmia<Type II hyposmia from most severe to least severe). Data indicates that as degree of smell loss increased, levels of cAMP in nasal mucus decreased. These data confirm the relationship between cAMP secretion in nasal mucus and degree of smell loss. Results also indicate that there was less significant difference between cGMP in nasal mucus in normal subjects or in patients with hyposmia. However, the concentration of cGMP in saliva is essentially similar to that of cAMP, phenomena different from that observed in other tissues.

The ability to smell and, in part, the ability to taste or to obtain flavor from food is regulated by the olfactory nerve system. The olfactory nerve system is complex and interconnected with several systems in the brain. Olfactory receptors located in the nose are specialized bipolar neurons with cilia protruding into the mucous covering the epithelium. The axons of the bipolar neurons are packed into bundles that form connections in the olfactory bulb in the brain. The olfactory bulbs contain a rich supply of neurotransmitters and neuromodulators. Chemosensory dysfunctions are usually described by the following terms: ageusia (absence of taste), hypogeusia, (diminished sensitivity of taste), dysgeusia (distortion of normal taste), anosmia (absence of smell), hyposmia (diminished sense of smell), and dysosmia (distortion of normal smell).

Treatment with drugs which increase cAMP secretion (e.g., the phosphodiesterase theophylline or cilostazol) increases nasal mucus cAMP concentration and are associated with increases in smell function. Thus, cAMP measurements are critical to monitor both loss of smell function and changes in smell function following treatment. The detection of cAMP and cGMP in nasal mucus provides a non invasive method of diagnosing various diseases related to human physiology and pathology. The methods of the present invention include treatment of diseases by modulating the concentrations of cAMP and cGMP by use of drugs or agents. The method of treatment is preferably by nasal administration.

Some embodiments of the invention include diagnosing a disease by detecting nitric oxide in the nasal specimen. Nitric Oxide (NO) is a pletrophic-signaling molecule implicated in diverse biological processes including inhibition of platelet aggregation, regulation of neurotransmission, vasodilation, immune responses and inflammation. NO is synthesized from arginine and $O_2$ by three nitric oxide synthase (NOS), enzymes endothelial NOS (eNOS), neuronal NOS (nNOS), and inducible NOS (iNOS). Each enzyme isoform is expressed in a variety of tissues and cell types. While eNOS and nNOS generally exhibit constitutive expression and are involved in physiological signaling and cellular maintenance functions, iNOS expression may be induced by inflammatory stimuli and may be associated with both normal and pathological immune responses. Table 32 in the examples illustrates detection and measurement of NO in human saliva and nasal mucus. NO was found to be present is in both saliva and nasal mucus and its mean concentration in saliva were 21% lower in patients than in normal subjects whereas in nasal mucus mean levels were 25% lower in patients. Treatment which increases cAMP in nasal mucus and improves smell function may be mirrored by increases in nasal mucus NO.

Some embodiments of the invention include diagnosing a disease by detecting insulin-like growth factor I in the nasal specimen. Insulin-like growth factor I (IGF 1), also known as somatomedin C belongs to the family of insulin-like growth factors that are structurally homologous to proinsulin. IGF 1 is a potent mitogenic factor that mediates growth-promoting activities of growth hormone postnatally. IGF 1 also promotes growth during embryonic growth and differentiation. Table 34 in the examples illustrates detection and measurement of IGF 1 in human saliva and nasal mucus in 26 subjects. Results show that IGF 1 concentration in nasal mucus was significantly greater than in saliva. Results indicate that the measurement of nasal mucus IGF 1 can be used as an index of human physiology and pathology. The detection of IGF 1 in nasal mucus provides a non invasive method of diagnosing various diseases related to human physiology and pathology. The diagnosis can further help in treatment of diseases by modulating the concentrations of IGF 1 by use of drugs.

Some embodiments of the invention include diagnosing a disease by detecting endoglin in the nasal specimen. Endoglin, also known as CD 105, is a type 1 integral membrane glycoprotein and is an accessory receptor for TGF-β super family ligands. Endoglin is expressed on vascular endothelial cells, chrondrocytes and syncytiotrophoblasts of term placenta. It is also found on activated monocytes, mesenchymol stem cells and leukemic cells of lymphoid and myeloid lineages. Table 39 illustrates detection and measurement of endoglin in the nasal mucus. Results indicate that the measurement of nasal mucus endoglin can be used as an index of human physiology and pathology. The detection of endoglin in nasal mucus provides a non invasive method of diagnosing various diseases related to human physiology and pathology.

Some embodiments of the invention include diagnosing a disease by detecting fibroblast growth factor (FGF) in the nasal specimen. FGF acidic is a member of the FGF family of mitogenic peptides. Unlike other members of the family, it lacks signal peptides. FGF is apparently secreted by mechanisms other than the classical protein secretion pathways. There are approximately 23 distinct members of this family. The nucleotide sequence of human FGF acidic is well known and it is a 155 amino acid protein. FGF mediates cellular responses by binding to and activating a family of four receptor tyrosine kinases. FGF is involved in wound healing as it binds heparin. It promotes endothelial cell proliferation by physical organization of endothelial cells into tubes. It promotes angiogenesis and stimulates the proliferation of fibroblasts that give rise to granulation tissue. It is a more potent angiogenic factor than either VFGF or PDGF. It acts on PC 12 cells; these cells also respond to NGF in a similar manner. Low levels of FGF have been found in blood of patients with depression. Acidic FGF was measured in blood plasma, urine, saliva and nasal mucus in 13 subjects. No FGF was found in any sample of plasma, urine or saliva. FGF was measured in three samples of the nasal mucus or in 23 percent of the subjects. Values ranged from 8-44 pg/ml with a mean±SEM of 24±13 pg/ml. These results suggest that FGF is present in nasal mucus and may be part of a feedback mechanism involving nasal cavity and brain since FGF is synthesized in the brain.

The diagnosis of the disease as disclosed herein can be used to enable or assist in the pharmaceutical drug development process for therapeutic agents. The analysis can be used to diagnose disease for patients enrolling in a clinical trail. The diagnosis can indicate the state of the disease of patients undergoing treatment in clinical trials, and show changes in the state during the treatment. The diagnosis can demonstrate the efficacy of a treatment, and can be used to stratify patients according to their responses to various therapies.

The methods of the present invention can be used to evaluate the efficacy of treatments over time. For example, sample of nasal secretions can be obtained from a patient over a period of time as the patient is undergoing treatment. The DNA from the different samples can be compared to each other to determine the efficacy of the treatment. Also, the methods described herein can be used to compare the efficacies of different therapies and/or responses to one or more treatments in different populations (e.g., different age groups, ethnicities, family histories, etc.).

Figure 2:
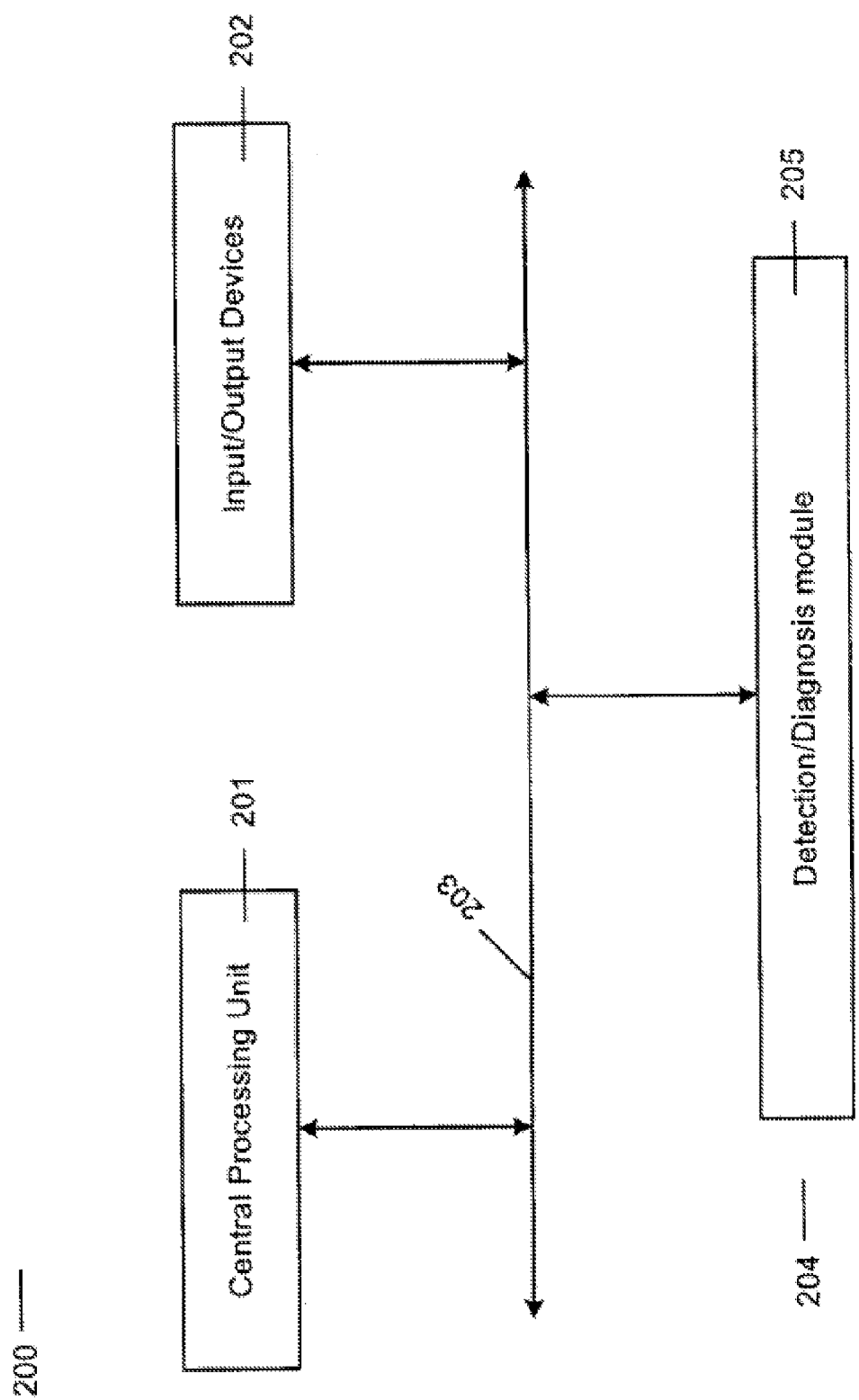
FIG. 2 illustrates a computer for implementing selected operations associated with the methods of the present invention.

In preferred embodiment, at least one step of the methods of the present invention is performed using a computer as depicted in FIG. 2. FIG. 2 illustrates a computer for implementing selected operations associated with the methods of the present invention. The computer 200 includes a central processing unit 201 connected to a set of input/output devices 202 via a system bus 203. The input/output devices 202 may include a keyboard, mouse, scanner, data port, video monitor, liquid crystal display, printer, and the like. A memory 204 in the form of primary and/or secondary memory is also connected to the system bus 203. These components of FIG. 2 characterize a standard computer. This standard computer is programmed in accordance with the invention. In particular, the computer 200 can be programmed to perform various operations of the methods of the present invention.

The memory 204 of the computer 200 may store a detection/diagnosis module 205. In other words, the detection/diagnosis module 205 can perform the operations associated with step 102, 103, and 104 of FIG. 1. The term "detection/diagnosis module" used herein includes, but not limited to, analyzing one or more biological substances, identifying the biological substance, and diagnosing the disease after the identification. The executable code of the detection/diagnosis module 205 may utilize any number of numerical techniques to perform the diagnosis.

Examples of Biological Substances

Various substances that can be diagnosed by the methods of the present invention include, by way of example only, proteins, carbohydrates, lipids, hormones (e.g., leptin, ghrelin) in control of appetite, cholesterol and other lipids and lipid carrying proteins in control of lipid metabolism, growth factors (e.g., hepatic growth factor, granulocyte colony growth factor, brain derived neurotrophic factor), liver enzymes (SGOT, SGPT) therapeutic and recreational drugs of abuse, trace metals [either excess as in toxicity (e.g., lead, mercury, arsenic) or in deficiency diseases involving zinc, copper, magnesium] and most other substances found in plasma, erythrocytes, urine and saliva. Each metabolite in nasal mucus may reflect both physiological and pathological changes in human body metabolism specific to each metabolite and may reflect the manner in which nasal mucus provides information both on human body metabolism such as provided by plasma, erythrocytes, urine and saliva or information relatively unique to nasal mucus.

The methods of the present invention include PCR to enable detection and/or characterization of specific nucleic acid sequences associated with infectious diseases, genetic disorders or cellular disorders. Various infectious diseases can be diagnosed by the presence in clinical samples of specific DNA sequences characteristic of the causative microorganism.

Infectious organisms may comprise viruses, (e.g., single stranded RNA viruses, single stranded DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria, M. tuberculosis, Salmonella, Chlamydia, Neisseria, Streptococci, E. coli, Staphylococci, C. psittaci* and *C. pecorum*), fungi (e.g., *Acremonium; Absidia* (e.g., *Absidia corymbifera*). *Aspergillus* (e.g., *Aspergillus clavatus, Aspergillus flavus, Aspergillus fumigatus, Aspergillus nidulans, Aspergillus niger, Aspergillus terreus, Aspergillus versicolor*, etc), *Blastomyces* (e.g., *Blastomyces dermatitidis*, etc), *Candida* (e.g., *Candida albicans, Candida glabrata, Candida guilliermondii, Candida kefyr, Candida krusei, Candida parapsilosis, Candida stellatoidea, Candida tropicalis, Candida utilis*, etc.), *Cladosporium* (e.g., *Cladosporium trichoides*, etc), *Coccidioides* (e.g., *Coccidioides immitis*, etc), *Cryptococcus* (e.g., *Cryptococcus neoformans*, etc), *Cunninghamella* (e.g., *Cunninghamella elegans*, etc), *Dermatophyte, Exophiala* (e.g., *Exophiala dermatitidis, Exophiala spinifera*, etc), *Epidermophyton* (e.g., *Epidermophyton floccosum*, etc), *Fonsecaea* (e.g., *Fonsecaea pedrosoi*, etc), *Fusarium* (e.g., *Fusarium solani*, etc), *Geotrichum* (e.g., *Geotrichum candiddum*, etc), *Histoplasma* (e.g., *Histoplasma capsulatum* var. *capsulatum*, etc), *Malassezia* (e.g., *Malassezia furfur*, etc), *Microsporum* (e.g., *Microsporum canis, Microsporum gypseum*, etc), *Mucor, Paracoccidioides* (e.g., *Paracoccidioides brasiliensis*, etc), *Penicillium* (e.g., *Penicillium marneffei*, etc), *Phialophora, Pneumocystis* (e.g., *Pneumocystis carinii*, etc), *Pseudallescheria* (e.g., *Pseudallescheria boydii*, etc), *Rhizopus* (e.g., *Rhizopus microsporus* var. *rhizopodiformis, Rhizopus oryzae*, etc), *Saccharomyces* (e.g., *Saccharomyces cerevisiae*, etc), *Scopulariopsis, Sporothrix* (e.g., *Sporothrix schenckii*, etc), *Trichophyton* (e.g., *Trichophyton mentagrophytes, Trichophyton rubrum*, etc), *Trichosporon* (e.g., *Trichosporon asahii, Trichosporon cutaneum*, etc).), *Pneumocystis carinii*, and prions.

Other examples of biological substances, includes, but is not limited to, colony stimulating factors (1, 2, 3, GM, α, β, γ, and the like), B cell factors (B cell growth factor and the like), T cell factors, protein A, suppressive factor of allergy, suppressor factors, cytotoxic glycoprotein, immunocytotoxic agents, immunotoxins, lymphotoxins, cachectin, oncostatins, tumor inhibitory factors, albumin, α-1-antitrypsin, apolipoprotein, erythroid potentiating factors, erythropoietin, factor VII, factor VIII(c), factor IX, hemopoietin-1, kidney plasminogen activator, tissue plasminogen activator, urokinase, pro-urokinase, streptokinase, lipocortin, lipomodulin, macrocortin, lung surfactant protein, protein C, protein 5, C-reactive protein, renin inhibitors, collagenase inhibitors, superoxide dismutase, growth hormone, osteogenic growth factors, atrial naturetic factor, auriculin, atriopeptin, bone morphogenic protein, calcitonin, calcitonin precursor, calcitonin gene-related peptide, cartilage inducing factor, connective tissue activator protein, fertility hormones (follicle stimulating hormone, luteinizing hormone, human chorionic gonadotropin), growth hormone releasing factor, osteogenic protein, insulin, proinsulin, nerve growth factor, parathyroid hormone and analogues, parathyroid hormone antagonists, relaxin, secretin, somatomedin C, somatostatin and somatostatin analogues, inhibin, adrenocoricotrophic hormone, glucagon, vasoactive intestinal polypeptide, gastric inhibitory peptide, motilin, cholecystokinin, pancreatic polypeptide, gastrin releasing peptide, corticotropin releasing factor, thyroid stimulating hormone, growth inhibitory factors, vaccine antigens including antigens of HTLV-I, II, HTLV-III/LAV/HIV (AIDS virus), cytomegalovirus, hepatitis A, B, and non-A/non-B, herpes simplex virus-I, herpes simplex virus II, malaria, pseudorabies, retroviruses, feline leukemia virus, bovine leukemia virus, transmissible gastroenteritis virus, infectious bovine rhinotracheitis, parainfluenza, influenza, rotaviruses, respiratory syncytial virus, varicella zoster virus, epstein-barr virus, pertussis, and anti-infective antibodies including monoclonal and polyclonal antibodies to gram negative bacteria, pseudomonas, endotoxin, tetanus toxin, and other bacterial or viral or other infectious organisms.

In addition to naturally-occurring allelic forms of growth inhibitory factor, the present invention also embraces other inhibitory factor products such as polypeptide analogs of inhibitory factor. Such analogs include fragments of inhibitory factor. Other examples of biological substances, includes, substances that are associated with cancer (either active or remission) and/or with reaction to transplantation (either tissue acceptance or rejection).

Examples of Diseases

Without limiting the scope of the present invention, the examples of some of the diseases which can be diagnosed by detecting the biological substance, is provided herein. However, these examples are not intended to limit the scope of the invention. The disease as provided herein include, infections, hematological disorders, oncological disorders, endocronological disorders, metabolic disorders, immunological disorders, neurological disorders, vascular disorders, mast cell disorders, psychiatric disorders, neoplastic disorders, nutritional disorders, post irradiation disorders, and changes in the trace metal metabolism.

Infectious diseases include acute and chronic parasitic and/or infectious diseases from bacterial, viral or fungal sources, but are not limited to, single or multiple cutaneous lesions, mucosal disease, chagas' disease, toxoplasmosis, leishmaniasis, trypanosomiasis, shistosomiasis, cryptosporidiosis, *mycobacterium avium* infections, leprosy, dengue, yellow fever, inner ear infections, urinary tract infections, bacterial endocarditis, osteomyelitis, *H. pylori* associated ulcers, antibiotic associated colitis, sexually transmitted diseases, malaria, rheumatoid arthritis, inflammatory bowel disease, interstitial cystitis, fibromyalgia, autonomic nervous dysfunction, pyoderma gangrenosum, chronic fatigue, chronic fatigue syndrome, sepsis syndrome, cachexia, circulatory collapse and shock resulting from acute or chronic bacterial infection, AIDS (including symptoms of cachexia, autoimmune disorders, AIDS dementia complex and infections), wegners granulomatosis, aneurysms, hemorrhoids, sarcoidosis, chronic inflammatory bowel disease, Crohn's disease, vascular inflammatory pathologies, such as, but not limited to, disseminated intravascular coagulation, atherosclerosis, and Kawasaki's pathology, inflammatory diseases such as coronary artery disease, hypertension, stroke, asthma, chronic hepatitis, multiple sclerosis, peripheral neuropathy, chronic vascular headaches (including migraines, cluster headaches, and tension headaches), demyelinating diseases, such as multiple sclerosis and acute transverse myelitis, extrapyramidal and cerebellar disorders, such as lesions of the corticospinal system, disorders of the basal ganglia or cerebellar disorders, hyperkinetic movement disorders such as huntington's chorea and senile chorea, drug-induced movement disorders, such as those induced by drugs which block CNS dopamine receptors, hypokinetic movement disorders, such as Parkinson's disease, progressive supranucleo palsy, cerebellar and spinocerebellar disorders, such as astructural lesions of the cerebellum, spinocerebellar degenerations (spinal ataxia, friedreich's ataxia, cerebellar cortical degenerations, multiple systems degenerations (mencel, Dejerine-Thomas, Shi-Drager, and Machado Joseph)), systemic disorders (Refsum's disease, abetalipoprotemia, ataxia, telangiectasia, and mitochondrial multi-system disorder), disorders of the motor unit, such as neurogenic muscular atrophies (anterior horn cell degeneration, such as amyotrophic lateral sclerosis, infantile spinal muscular atrophy and juvenile spinal muscular atrophy), Alzheimer's disease, Down's Syndrome in middle age, diffuse Lewy body disease, senile dementia of lewy body type, Wernicke-Korsakoff syndrome, chronic alcoholism, Creutzfeldt-Jakob disease, subacute sclerosing panencephalitis, Hallerrorden-Spatz disease, and Dementia pugilistica, dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, *chromomycosis*, coccidioidomycosis, histoplasmosis, blastomycosis, paracoccidioidomycosis, pseudallescheriosis, mycetoma, mycotic keratitis, otomycosis, and pneumocystosis.

Ocular neovascularization, psoriasis, duodenal ulcers etc can also be treated when demonstrated by the diagnostic procedures described herein. Similarly, other diseases (their biological substances in parenthesis), include, but not limited to, neutropenia, gout, dwarfism or congenital short stature (growth hormone releasing hormone (GHRH)); congestive heart disease (atrial natriuretic peptide or factor (ANP or ANF)); osteoporosis (parathyroid hormone (PTH)); Paget's disease (calcitonin); accromegally, insulin sparing effects, treatment of long term complications of diabetes and treatment of various endocrine secreting tumors (somatostatin); Addison's Disease and Cushing's Syndrome, shipping fever (bovine respiratory syndrome) or ulcers, and stress-induced immunosuppression (corticotrophin releasing factor (CRF)); contraception, fertility control, suppression or interruption of heat, treatment of ovarian cysts, precocious puberty, prostatic hyperplasia and tumors, gynecologic diseases, and termination of pregnancy (luteinizing hormone-releasing hormone (LHRH)); aplastic anemia, paroxysmal nocturnal hemoglobinurea, chronic myelocytic leukemia, polycythemia vera, essential thrombocythemia, myelofibrosis, myelodysplastic syndrome and acute leukemia; and hematological diseases such as megaloblastic anemia, AIDS, multiple myeloma, metastatic cancer of the bone marrow, and drug-induced myelosuppression (hematopoietic stem cell growth factor (SCGF)); body weight disorders, including obesity, cachexia, and anorexia, and diabetes, neoplasms, and hyperamylinemia (agouti-related protein); impairment of functions, increased ceramide formation, which triggers nitric oxide-mediated lipotoxicity and lipoapoptosis, obesity and hyperphagia (leptin); hypolipidimia, coronary heart disease, Niemann Pick Disease, Gaucher's disease, Batten's syndrome, Farber's lipogranulomatosis, Krabbe's disease, metachromic leukodystrophy, Tay-Sach's disease, GM1 gangliosidoses, Fabry's disease, cystinosis, aspartylglycosaminuria (lipid profile which includes triglycerides, LDL-cholesterol and HDL-cholesterol), and generalized vascular disease, chronic hyperglycemia, obesity, hypertension, atherosclerosis and heart disease, carbohydrate deficient glycoprotein syndrome type 1a, glycogenoses, and galactosemia (carbohydrates).

Detection of the concentration of the caspases in the nasal secretion can provide diagnosing a disorder or selection of therapeutic strategies involving, e.g., inappropriate apoptosis and/or excessive cell proliferation, such as an inflammatory disease, a neurodegenerative disease, cancer, a cardiovascular disease and, any disorder or disease characterized by a gradual and prolonged development of apoptosis. Apoptosis functions in maintaining normal tissue homeostasis in a variety of physiological processes including embryonic development, immune cell regulation, normal cellular turnover and programmed cell death of cancer cells. Thus, the dysfunction or loss of regulated apoptosis can lead to a variety of pathological disease states. For example, the loss of apoptosis can lead to the pathological accumulation of self-reactive lymphocytes such as occurs in many autoimmune diseases. Inappropriate loss of apoptosis can also lead to the accumulation of virally infected cells and of hyperproliferative cells such as neoplastic or tumor cells. Inappropriate activation of apoptosis can contribute to a variety of diseases such as AIDS, neurodegenerative diseases and ischemic injury.

Dysregulation of apoptosis has been implicated in numerous diseases such as neurodegenerative disorders including Alzheimer's disease, Parkinson's disease, Huntington's disease, and amyotrophic lateral sclerosis (ALS), cerebellar degeneration, stroke, traumatic brain injury, CNS ischemic reperfusion injury including neonatal hypoxic-ischemic brain injury or myocardial ischemic-reperfusion injury, injury caused by hypoxia, cardiovascular diseases (e.g., myocardial infarction), especially those which are associated with apoptosis of endothelial cells, degenerative liver disease, multiple sclerosis, rheumatoid arthritis, hematological disorders including lymphoma, leukemia, aplastic anemia, and myelodysplastic syndrome, osteoporosis, polycystic kidney disease, AIDS, myelodysplastic syndromes, aplastic anemia and baldness. Diseases of the eye include glaucoma, retinitis pigmentosa and macular degeneration.

Inflammatory disease states include systemic inflammatory conditions and conditions associated locally with migration and attraction of monocytes, leukocytes and/or neutrophils. Inflammation may result from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Examples of pathological conditions resulting from increased cell survival include cancers such as lymphomas, carcinomas and hormone-dependent tumors (e.g., breast, prostate or ovarian cancer). Abnormal cellular proliferation conditions or cancers that may be treated in either adults or children include solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Viral infections that may be detected include infections caused by herpesviruses (including CMV, HSV-1, HSV-2, VZV, EBV, HHV-6, HHV-7 and HHV-8), paramyxoviruses (including parainfluenza, mumps, measles, and respiratory syncytial virus (RSV)), picornaviruses (including enteroviruses and rhinoviruses), togaviruses, coronaviruses, arenaviruses, bunyaviruses, rhabdoviruses, orthomyxoviruses (including influenza A, B and C viruses), reoviruses (including reoviruses, rotaviruses and orbiviruses), parvoviruses, adenoviruses, hepatitis viruses (including A, B, C, D and E) and retroviruses (including HTLV and HIV). Treatments of both acute and chronic infection are contemplated.

Adenylyl cyclases are a family of enzymes that catalyze the formation of Adenosine-3':5-cyclic monophospate (cAMP) from adenosine-5'-triphosphate (5'ATP), mediate the physiological effects of numerous hormones and neurotransmitters, and belong to a super family of membrane-bound transporters and channel proteins. Adenosine-3':5'-cyclic monophosphate (cAMP) is the second messenger involved in signal transduction for numerous neurotransmitters and hormones, and thus may have an impact upon some of the mediators for smooth muscle cells (SMC) proliferation and migration. Many hormones and other substances may activate cAMP and may activate the subsequent signaling cascades via their indirect influence on adenylyl cyclase. cAMP is a growth factor for neurite growth and is involved in development in tissue culture of sympathetic ganglion cells similar to the action of NGF. Adenylyl cyclase is a growth factor which acts on stem cells in taste buds and olfactory epithelium to induce growth and development of all cell types in taste buds and olfactory epithelium. cGMP, guanosine 3',5"-cyclic monophosphate is formed by the action of guanylyl cyclase on GTP. cGMP is present at levels typically lower than cAMP in most tissues. Hormones, such as insulin and oxytocin as well as other substances including acetylcholine, serotonin and histamine may increase cGMP levels. Stimulators of cGMP may include vasodilators and peptides that relax smooth muscle.

Adenylyl cyclases also play a role in the disease progression of Congestive heart failure (CHF). CHF is defined as an abnormal heart function resulting in an inadequate cardiac output for metabolic needs. Heart failure is usually not recognized until a more advanced stage of heart failure which is referred to as congestive heart failure. On physical examination, patients with CHF tend to have elevations in heart and respiratory rates, rates (an indication of fluid in the lungs), edema, jugular venous distension, and, in general, enlarged hearts. The most common cause of CHF is atherosclerosis which causes blockages in the blood vessels (coronary arteries) that provide blood flow to the heart muscle. Ultimately, such blockages may cause myocardial infarction (death of heart muscle) with subsequent decline in heart function and resultant heart failure.

Fibroproliferative vasculopathy includes restenosis following coronary bypass surgery and PTCA (percutaneous transluminal coronary angioplasty), allograft arteriosclerosis in chronic allograft rejection, diabetic angiopathy and all forms of common arteriosclerosis. Vascular intimal dysplasia and remodeling are characteristic features of reinjury following balloon angioplasty, coronary bypass surgery and in chronic allograft rejection. An initial response to vascular injury is inflammatory and involves attraction of lymphocytes, macrophages and thrombocytes to the site of injury and secretion of cytokines, eicosanoids and growth factors. Under the influence of growth factors and cytokines, smooth muscle cells (SMC) may proliferate and migrate from the media to the intima and contribute to intimal hyperplasia and stenosis. cAMP has an impact upon some of the key mediators for SMC proliferation and migration.

Glucose is irreversibly oxidized within the cells to produce water and carbon dioxide. In the presence of a catalyst, especially a carbonic anhydrase enzyme (of which several forms exist, of which the form present depends upon the type of tissue cells present), the water and carbon dioxide may reversibly produce a hydrogen ion and a bicarbonate ion. Hydrogen ion produced by carbonic anhydrase enzymes can be acted upon by cytochrome system, which can then be utilized as the energy source of the ion pump that maintains the integrity of the cell membrane comprising and enclosing each cell. It can also be a source of the brain's electric current. Disruption of the process may cause depolarization of the cell wall membrane, hence sodium (Na), water, and other chemicals can enter the cell in uncontrolled amounts and potassium (K) can exit uncontrollably, leading to the death and destruction of the involved cells followed by cellular edema. As this edema progresses, the cell dies. Along with the progressive and gradual death of cells, gliosis may follow resulting in the aging in the brain. The deficiency of carbonic anhydrase can cause conditions of aging associated with a decreased presence of cell-specific carbonic anhydrase enzymes in the brain, such as chronic neurodegenerative conditions including dementia such as Alzheimer's disease, or showing other forms of dementia or neurodegenerative diseases.

Methods of Treatment

The substances secreted into saliva and nasal mucus act on local oral and nasal tissues, respectively, to induce physiological effects. There are several effects of gland secretion at distant sites: (1) endocrine-secretions from a gland and subsequent action at a distant site, the secretion carried in blood to the distant site; (2) paracrine-secreted substances act at a distant site within the local reach of the fluid; (3) exocrine-secretions from a gland which have direct local effects, e.g, β-cells in the pancreas which act directly to secrete insulin in response to local changes in blood glucose. This is a one directional effect, a secretion from the gland, into the biological fluid, acting at a distant but local site.

There are feedback mechanisms such that whatever effects the gland secretion had on its receptor, the receptor also interacted with the site of secretion. For example, increased glucose induces increased secretion of insulin but as insulin secretion increases, insulin receptor number in liver and pancreas change in response to the increased insulin secretion. This feedback concept can also be exemplified by brain secretion of peptide hormones which acted as master feedback mechanisms to control peripheral hormone secretion. Thus, there are interactions between brain, gland and a receptor with the interactions proceeding in both directions. For example, TRH secreted from the brain hypothalamus stimulates pituitary TSH which acts to stimulate thyroid $T_3$ and $T_4$ which can act back on both pituitary and brain in the form of both long (to brain) and short (to pituitary) feedback loops.

Figure 11:
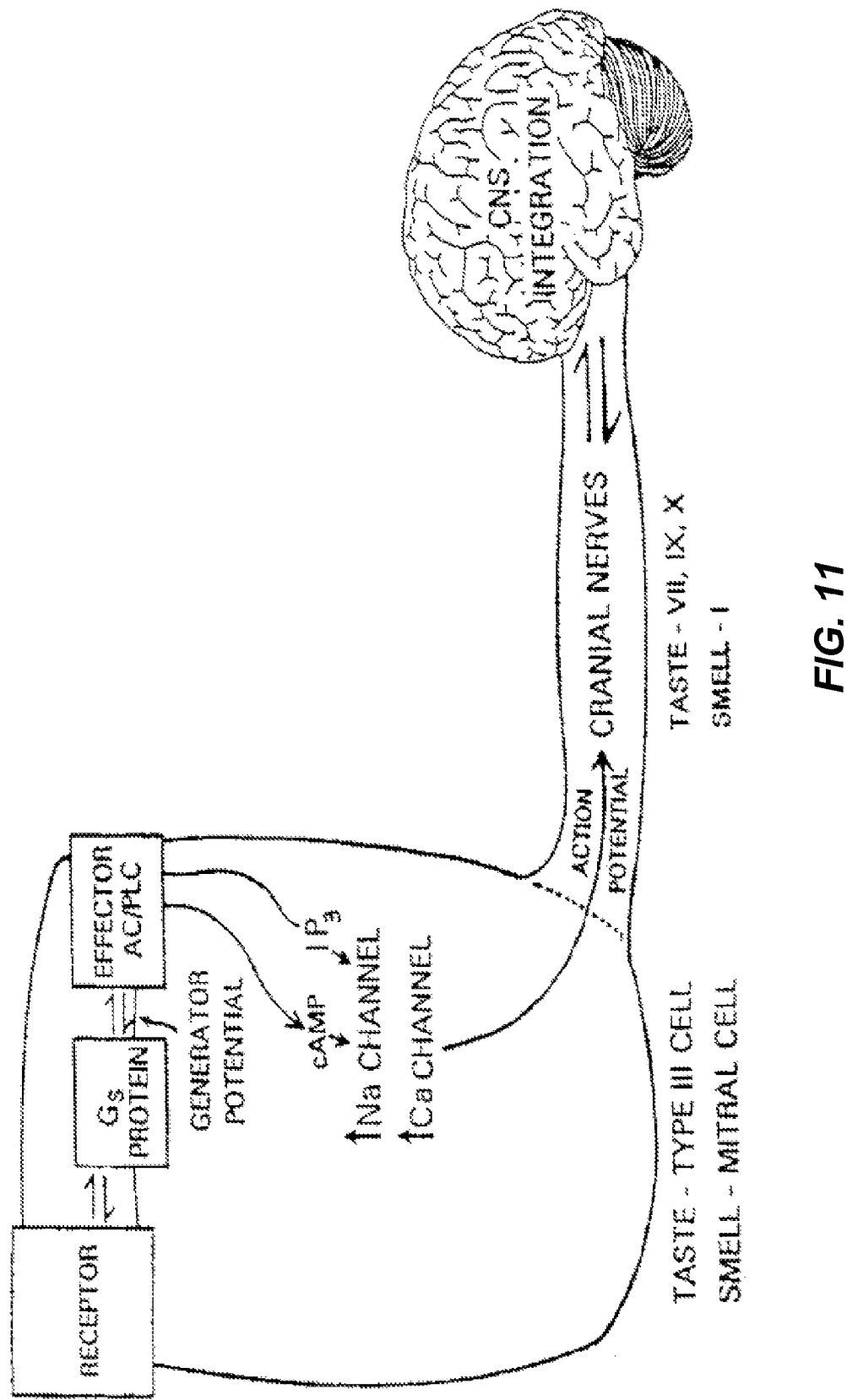
FIGS. 11 and 12 reflect a feedback mechanism with effects acting from nose to brain and from brain to nose.
Figure 12:
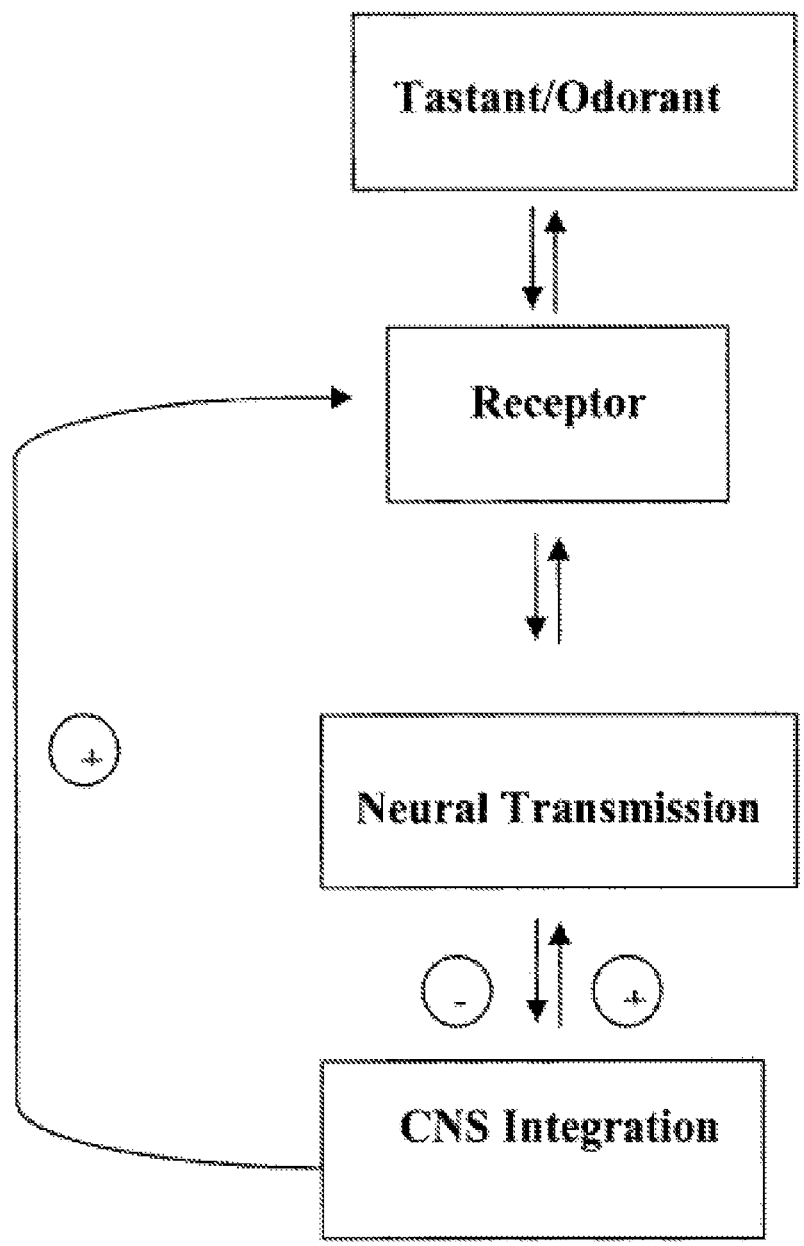

Henkin, R. I., Olfaction and Taste XI, (Kurihara, K., Suzuki, N., Ogawa, H., Eds.), Springer Verlag, 1994, pp. 568-573, incorporated herein by reference in its entirety, described the concept involving saliva and nasal mucus secretions related to taste and smell function (FIGS. 11 and 12). These results suggest that tastants and odorants affect brain function and vice versa. Since saliva and nasal mucus are the critical factors in maintaining the taste and smell systems, respectively, it is understandable that substances in these fluids also affect brain function and vice versa. Therefore, nasal administration of substances can affect brain function and thereby affect various physiological and pathological problems. For example, nasal administration of leptin (to control obesity), agouti-related protein (to increase appetite in anorexic patients), glucose, albumin, insulin (to treat diabetes), hormones (hormonal disorders), etc.

These effects may act through the large arteriovenous plexus of blood vessels in the nose such that absorption of the substances may be enhanced by direct contact and absorption through these exposed vessels. FIGS. 11 and 12 reflect a feedback mechanism with effects acting from nose to brain and from brain to nose, as in both a short and long loop feedback system.

Treatment with Drug

Theophylline treatment restores smell function in some patients with hyposmia (loss of smell). Theophylline is a phosphodiesterase (PDE) inhibitor; it restores smell function through PDE inhibition thereby increasing cAMP, a growth factor which stimulates maturation of olfactory epithelial stem cells, cells whose functions are inhibited among patients with hyposmia. Theophylline may also restore smell function through other mechanisms. One such mechanism may operate through inhibition of excessive apoptosis, a normal process which, if excessively increased, can become pathological and impair cellular anatomy of the olfactory epithelium and cause hyposmia.

Table 16 illustrates detection and measurement of TRAIL in nasal mucus in patients with hyposmia before and after treatment with theophylline at various doses. Data indicated that treatment with theophylline which returned smell function to normal in a dose-dependent manner was associated with a dose-dependent decrease in TRAIL. These data indicate that treatment with a drug demonstrated a dose dependent decrease in TRAIL which indicates a decrease in the abnormal apoptotic processes. These data also indicate both a biochemical and functional improvement in smell function by treatment with theophylline. Without limiting the scope of the present invention, other drugs are also considered with in the scope of the present invention for the treatment of various diseases. This is one of the example of the multiple examples of drugs to treat disease in which changes of various substances found in nasal mucus reflect biochemical normalization and functional improvement in the disease process.

Table 33 in the examples illustrates NO in nasal mucus in patients treated with theophylline in various doses before and after drug treatment. NO levels in nasal mucus changed following the treatment of patients with smell loss. Results show treatment of patients with graded increasing doses of theophylline and measurement of both smell function and NO in nasal mucus in patients with hyposmia. Results indicated that prior to the treatment levels of NO in nasal mucus were lower than in normal subjects. After treatment with theophylline in graded doses there were increases in nasal mucus NO associated with graded increases in smell function. These data demonstrate that treatment with drugs that increase smell function to or toward normal, returns smell function to normal. These results demonstrate the measurements of various substances in nasal mucus as an index of both human physiology and pathology of various diseases. Its continual measurement during treatment of the disorders helps in monitoring efficacy of therapy. The detection of NO in nasal mucus provides a non invasive method of diagnosing various diseases related to human physiology and pathology. The methods of the present invention include treatment of diseases by modulating the concentrations of NO by use of drugs or agents. The method of treatment is preferably by nasal administration.

Tables 36-38 illustrate detection and measurement of TNFα, TNFR 1 and TNFR 2 in nasal mucus of patients with graded loss of smell following treatment with theophylline. Results indicate that detection and measurements of TNFα, TNFR 1 and TNFR 2 in nasal mucus can be used as an index of the disease process and of changes toward normal as the disease is successfully treated, in the present case with theophylline. Further, nasal mucus can be used as an index of disease, disease severity and efficacy of disease treatment. Without limiting the scope of the present invention, this approach is applicable to other substances in nasal mucus in relationship to other disease processes (e.g., cancer, stroke) and to follow-up of their treatment with any drug.

Treatment with Transcranial Magnetic Stimulation

Loss of taste and smell acuity (hypogeusia and hyposmia, respectively) with subsequent gustatory and olfactory distortions in the absence of oral or external olfactory stimuli [(phantageusia and phantosmia, respectively) labeled sensory distortions], are symptoms which may occur in some patients without other neurological or psychological disorders.

Transcranial magnetic stimulation (TCMS) use has been limited by lack of objective methods to measure efficacy of its application. One aspect of the invention includes method of treatment of patients with loss of taste and/or smell (hypogeusia and/or hyposmia, respectively) with subsequent gustatory and/or olfactory distortions (phantageusia and/or phantosmia, respectively) with repetitive TCMS (rTCMS) which improved their sensory acuity and decreased their sensory distortions.

Increased CA VI secretion has been considered a marker for both increased taste and smell function. Thus, before and after rTCMS, CA VI activity and other salivary proteins were measured in patients with both sensory loss and presence of sensory distortions. Since CA VI is a zinc containing glycose talloprotein, the salivary zinc and copper concentrations were also measured to determine if changes in these parameters correlated with changes in CA VI activity. The possibility of the changes in other salivary proteins was also investigated. Changes in erythrocyte CA I, II as well as concentrations of zinc and copper in both erythrocytes and in blood plasma, were also measured.

Example 40 shows the study of ninety-three patients with hyposmia, hypogeusia, phantosmia and/or phantageusia before and after rTCMS. Measurements were made of activities of CA I, II in erythrocytes and of CA VI, of concentrations of zinc and copper in parotid saliva, blood serum, and erythrocytes and of appearance of proteins in saliva by SELDI-TOF mass spectrometry. Results showed that after rTCMS, significant increases occurred in CA I, II, CA VI, and in concentrations of zinc and copper in blood plasma, erythrocytes and saliva. Salivary proteins at m/z value of 21.5K with a repeating pattern at intervals of 5K m/z were induced.

These results demonstrate the biochemical changes in specific enzymatic activities and trace metal concentrations following rTCMS. These changes may relate not only to several aspects of clinical abnormalities of sensory function but also to other neurological disorders including epilepsy, parkinsonism, alzheimer disease, head injury and motor neuron disease. Example 41 shows efficacy of treatment with rTCMS for patients with these cognitive impairments such as hypogeusia, hyposmia, phantageusia, and phantosmia.

Other Example of Drugs

Drugs that may be used in the methods of treatment of the present invention may be selected from the following, viz. vaccination, alcohol abuse preparations, drugs used for Alzheimer's disease, anesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS; stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for slain ailments, steroids and hormones; Examples of alcohol abuse preparations are chlorazepate, chlordiazepoxide, diazepam, I disulfuram, hydroxyzine, naltrexone and their salts.

Examples of analgesics are acetaminophen, aspirin, bupivacain, boprenorphine, butorphanol; celecoxib, clofenadol, choline, clonidine, codeine, diflunisal, dihydrocodeine, dihydroergotamine, dihydromorphine, ethylmorphine, etodolac, eletriptan, eptazocine, ergotamine, fentanyl, fentoprofen, hyaluronic acid, hydrocodon, hydromorphon, hylan, ibuprofen, lindomethacin, ketorolac, lcetotifen, levomethadon, levallorphan, levorphanol, lidocaine, mefenamic acid, meloxicam, meperidine, metll adone, morphine, nabumetone, nalbuphin, nefopam, nalorphine, naloxone, naltrexone, naproxen, naratriptan, nefazodone, mormethadon, oxaprozin, oxycodone, oxymorphon, pentazocin, pethidine, phenpyramid, piritramid, piroxicam, propoxyphene, refecoxib, rizatriptan, salsalaketoprofen, sulindac, sumatriptan, tebacon, tilidin, tolmetin, tramadol, zolmitriptan and their salts.

Examples of antiasthmatics are ablukast, azelastine, bunaprolast, cinalukast, cromitrile, cromolyn, enofelast, isamoxole, ketotifen, levcromekalin, lodoxamide, montelukast, ontazolast, oxarbazole, oxatomide, piriprost potassium, pirolate, pobilukast edamine, quazolast, repirinast, ritolukast, sulukast, tetrazolastmeglumine, tiaramide, tibenelast, tomelukast, tranilast, verlukast, verofylline, szarirlukast.

Examples of anticancer agents are adriamycin, aldesleukin, allopurinol, altretamine, amifostine, anastrozole, asparaginase, betamethasone, bexarotene, bicalutamide, bleomycin, busulfan, capecitabine, carboplatin, cannustine, chlorambucil, cisplatin, cladarabine, conjugated estrogen, cortisone, cyclophosphamide, cylarabine, dacarbazine, daunorubicin, dactinomycin, denileukin, dexamethasone, discodermolide, docetaxel, doxorubicin, eloposidem, epirubicin, epoetin, epothilones, estramustine, esterified estrogen, ethinyl estradiol, etoposide, exemestane, flavopirdol, fluconazole, fludarabine, fluorouracil, flutamide, floxuridine, gemcitabine, gemtuzumab, goserelin, hexamethylmelamine, hydrocortisone, hydroxyurea, idarubicin, ifosfamide, interferon, irinotecan, lemiposide, letrozole, leuprolide, levamisole, levothyroxine, lomustine, mechlorethamine, melphalan, mercaptopurine mechlorethamine, megesterol, methotrexate, methylprednisolone, methyltestosterone, mithramycin, mitomycin, mitotane, mitoxantrone, mitozolomide, mutamycin, nilutamide, paclitaxel, pamidronate, pegaspargase, pentostatin, plicamycin, porfimer, prednisolone, procarbazine, rituximab, sargramostim, semustine, skeptozocin, tamoxifen, temozolomide, teniposide, testolactone, thioguanine, thiotepa, tomudex, topotecan, toremifene, trastumuzab, tretinoin, semustine, skeptozolocin, valrubicin, verteporfin, vinblastine, vincristine, vindesine, vinorelbine and their salts.

Examples of anticoagulants and antithrombic agents are warfarin, dalteparin, heparin, tinzaparin, enoxaparin, danaparoid, abciximab, alprostadil, altiplase, anagralide, anikseplase, argatroban, ataprost, beraprost, camonagreel, cilostazol, clinprost, clopidogrel, cloricromen, dermatan, desirudin, domitroban, drotaverine, epoprostenol, eptifibatide, *adafiban, gabexate, iloprost, isbogrel, lamifiban, lamoteplase, le*adafiban, lepirudin, levosimendan, lexipafant, melagatran, nafagrel, nafamostsat, nizofenone, orbifiban, ozagrel, pamicogrel, parnaparin, quinobendan, reteplase, sarpogralate, satigrel, silteplase, simendan, ticlopidine, vapiprost, tirofiban, xemilofiban, Y20811 and their salts.

Examples of anticonvulsants are carbamazopine, clonazepam, clorazepine, diazepam, divalproex, ethosuximide, ethotion, felbamate, fosphenyloin, gabapentin, lamotrigine, levetiracetam, lorazepam, mephenyloin, mephobarbital, metharbital, methsuximide, oxcarbazepine, phenobarbital, phenyloin, primidone, tiagabine, topiramate, valproic acid, vigabatrin, zonisamide, and their salts. Examples of antidiabetic agents are acarbose, acetohexamide, carbutamide, chlorpropamide, epalrestat, glibornuride, gliclazide, glimepiride, glipizide, gliquidone, glisoxepid, glyburide, glyhexamide, metformin, miglitol, nateglinide, orlistat, phenbutamide, pioglitazone, repaglinide, rosiglitazone, tolazamide, tolbutamide, tolcyclamide, tolrestat, troglitazone, voglibose and their salts.

Examples of antiemetics are alprazolam benzquinamide, benztropine, betahistine, chlorpromazine, dexamethasone, difenidol, dimenhydrinate, diphenhydramine, dolasetron, domperidone, dronabinol, droperidol, granisetron, haloperidol, lorazepam, meclizine, methylprednisolone, metoclopramide, ondansetron, perphenazine, prochlorperazine, promethazine, scopolamine, tributine, triethylperazine, triflupromazine, trimethobenzamide, tropisetron and their salts.

Examples of antiglaucoma agents are alprenoxime, dapiprazole, dipivefrin, latanoprost, naboctate, pirnabine and their salts.

Examples of antihistamines are acrivastine, activastine, albuterol, azelastine, bitolterol, alimemazine, amlexanox, azelastine, benzydamine, brompheniramine, cetirizine, chlorpheniramine, cimetidine, clemastine, cycloheptazine, cyproheptadine, diclofenac, diphenhydramine, dotarizine, ephedrine, epinastine, epinephrine, ethyluorepinephrine, fenpoterol, 2s fexofenadine, flurbiprofen, hydroxyzine, ibuprofen, isoetharine, isoproterenol, ipratropium bromide, ketorolac, levocetirizine, loratidine, mequitazine, metaproterenol, phenylephrine, phenylpropanol amine, pirbuterol, promethazine, pseudo ephedrine, pyrilamine, salmeterol, terbutaline, tranilast, xanthine derivatives, xylometazoline and their salts.

Examples of anti-infective agents are abacavir, albendazole, amantadine, amphotericin, amikacin, aminosalicylic acid, amoxycillin, ampicillin, amprenavir, atovaquin, azithromycin, aztreonam, carbenicillin, cefaclor, cefadroxil, cefamandole, cefazolin, cefdinir, cefepime, cefexime, cefoperazone, cefotaxime, cefotitam, cefoperazone, cefoxitin, ceLpodoxine, cefprozil, ceftazidime, ceftibuten, ceftizoxime, ceftriaxone, cefuroxime, cephalexin, chloroquine, cidofovir, cilastatin, ciprofloxacin, clarithromycin, clavulinic acid, clindamycin, colistimethate, dalfopristine, dapsone, daunorubicin, delavirdin, demeclocycline, didanosine, doxycycline, doxorubicin, efavirenz, enoxacin, erythromycin, ethambutol, ethionamide, famsiclovir, fluconazole, flucytocin, foscarnet, fosfomycin, ganciclovir, gatifloxacin, griseofulvin, hydroxychloroquine, imipenem, indinavir, interferon, isoniazide, itraconazole, ivermectin, ketoconazole, lamivudine, levofloxacin, linezolide, lomefloxacin, lovacarbef, mebendazole, mefloquine, meropenem, methanamine, metronidazole, minocycline, moxefloxacin, nalidixic acid, nelfnavir, neomycin, nevirapine, nitrofurantoin, norfloxacin, ofloxacin, olseltamnivir, oxytetracycline, palivizumab, penicillins, perfloxacin, piperacillin, praziquantel, pyrazinamide, pyrimethamine, quinidine, quinupristine, retonavir, ribavirin, rifabutine, rifampicin, rimantadine, saquinavir, sparfloxacin, stavudine, streptomycin, sulfamethoxazole, teramycin, terbinafine, tetracycline, ticarcillin, thiabendazole, tobramycin, trimethoprim, trimetraxate, troleandomycin, trovafloxacin, valacyclovir, vancomycin, zalcitabine, zanamivir, zidovudine and their salts.

Examples of antiparkinsons are amantadine, adrogolide, altinicline, benztropine, biperiden, brasofensine, bromocriptine, budipine, cabergoline, dihydrexidine, entacapone, etilevodopa, idazoxan, iometopane, lazabemide, melevodopa, carbidopa/levodopa, mofegiline, moxiraprine, pergolide, pramipexole, quinelorane, rasagiline, ropinirole, seligiline, talipexole, tolcapone, trihexyphenidyl and their salts. Examples of antirheumatic agents are azathiprine, betamethasone, celecoxib, cyclosporin, diclofenac, hydroxychloroquine, indomethacin, infliximab, mercaptobutanedioic acid, methylprednisolone, naproxen, penicillamine, piroxicam, prednisolone, sulfasalazine and their salts.

Examples of platelet agents are abciximab, anagrelide, aspirin, cilostazol, clopidogrel, dipyridamole, epoprostenol, eptifbatide, ticlopidine, tinofban and their salts. Examples of antispasmodics and anticholinergic agents are aspirin, atropine, diclofenac, hyoscyamine, mesoprostol, methocarbamol, phenobarbital, scopolamine and their salts.

Examples of antitussives are acetaminophen, acrivastin, albuterol, benzonatate, beractant, brompheniramine, caffeine, calfactant, carbetapentane, chlorpheniramine, codeine, colfuscerin, dextromethorphan, dornase alpha, doxylamine, epinephrine, fexofenadine, guaiphenesin, iprakopium, levalbuterol, metaproterenol, montelukast, pentoxyphyline, phenylephrine, phenylpropanolamine, pirbuterol, poractant alpha, pseudoephedrine, pyrilamine, salbuterol, salmeterol, terbutaline, theophylline, zafirlukast, zileuton and their salts. Examples of carbonic anhydrase inhibitors are acetazolamide, dichlorphenamide, dorzolamide, methazolamide, sezolamide and their salts.

Examples of cardiovascular agents are abciximab, acebutolol, activase, adenosine, adrenaline, amidarone, amiloride, amlodipine, amyl nikate, atenolol, atorvastatin, benazepril, bepiridil, betaxalol, bisoprolol, candesartan, captopril, cartenolol, carvedilol, cerivastatin, chlorthalidone, chlorthiazole, clofibrate, clonidine, colestipol, colosevelam, digoxin, diltiazem, disopyramide, dobutamine, dofetilide, doxazosin, enalapril, epoprostenol, eprosartan, esmolol, ethacrynate, erythrityl, felodipine, fenoidapam, fosinopril, fleicamide, fluorosemide, fluvastatin, gewhibrozil, hydrochlorthiazide, hydroflumethazine, ibutilide, indapamide, isosorbide, irbesartan, labetolol, lacidipine, lisinopril, losartan, lovastatin, mecamylamine, metoprolol, metaraminol, metazolone, methylchlorthiazide, methyldopa, metyrosine, mexiletine, midrodine, milrinone, moexipril, nadolol, niacin, nicardipine, nicorandil, nifedipine, nimodipine, nisoldipine, nikoglycerin, phenoxybenzamine, perindopril, polythiazide, pravastatin, prazosin, procainamide, propafenone, propranolol, quanfacine, quinapril, quinidine, ranipril, reteplase, simvastatin, sotalol, spironolactone, skeptokinase, telmisartan, terazosin, timolol, tocainamide, tors-emide, kandolapril, kiamterene, kapidil, valsartan and their salts.

Examples of cholinesterase inhibitors are donepezil, edrophonium, neostigmine, pyridostigmine, rivasti.gmine, tacrine and their salts. Examples of CNS stimulants are caffeine, doxapram, dexoamphetamine, donepezil, edrophonium, methamphetamine, methylphenidate, modafinil, neostigwine, pemoline, phentermine, pyridostigmine, rivastigwine, tacrin and their salts. Examples of cystic fibrosis management are dornase alpha, pancrelipase, tobramycin and their salts. Examples of dopamine receptor agonists are amantadine, cabergoline, fenoldopam, pergolide, pramipexil, ropinirole and their salts. Examples of drugs used for endometriosis management are danazol, goserelin, leuprolide, nafarelin, norethindrone and their salts. Examples of drugs used for erectile dysfunction therapy are alprostadil, sildenafil, yohimbine and their salts. I Examples of gastrointestinal agents are aldosetron, bisacodyl, bismuth subsalicylate, celecoxib, difoxin, dipheoxylate, docusate, famotidine, glycopyrrolate, infliximab, lansoprazole, loperamide, metaclopramide, nizatidine, omeprazole, pantoprazole, rabeprazole, ranitidine, simethicone, sucralfate, and their salts.

Examples of immunomodulators and immunosupressives are azathioprin, ceftizoxine, cyclosporin, daclizumab, glatiramer, immunoglobulin, interferon, leflunomide, levamisol, mycophenolate, mausomanab, phthalidomide, ribavirin, sirolimus and their salts. Examples of drugs used in Alzheimer's disease are donepezil, galanthamine, metrifonate, rivastigwine, tacrine, TAK-147 and their salts. Examples of drugs used for migraine preparations are acetaminophen, dihydroergotamine, divalproex, ergotamine, propranolol, risatriptan, sumatriptan, trimetrexate and their salts. Examples of muscle relaxants are alcuronium-chloride, azapropazon, atracurium, baclofen, carisoprodol, quinine derivatives, chloromezanon, chlorophenesincarbamate, chlorozoxazon, cyclobenzaprine, dantrolene, decamethoniumbromide, dimethyltubocurariniumchloride, doxacurium, fenyrami dol, gall amintriethio dide, guaiphenesin, hexafluoreniumbromide, hexacarbacholinbromide, memantin, mephenesin, meprobamate, metamisol, metaxalone, methocarbamol, mivacurium, orphenadrin, pancuronium, phenazon, phenprobamate, pip e curonium, rap acuronium, ro curonium, suc cinylcholine, soxamethoniumchloride, tetrazepam, tizanidine, tubocurarine chloride, tybamate, vecuronium and their salts.

Examples of nucleoside analogues are abacavir, acyclovir, didanosine, ganciclovir, gewcitabine, lamivudine, ribavirin, stavudine, zalcitabine and their salts. Examples of drugs used for osteoporosis management are alendronate, calcitonin, estradiol, estropipate, medroxyprogesterone, norethindrone, norgestimate, pamidronate, raloxifen, risdronate, zolendronate and their salts. Examples of parasympathomimetics are bethanechol, piperidine, edrophonium, glycopyrolate, i hyoscyamine, pilocarpine, tacrine, yohimbine and their salts. Examples of prostaglandins are alprostadil, epoprostenol, misoprostol and their salts. Examples of psychotherapeutic agents are acetophenazine, alentemol, alpertine, alprazolam, amitriptyline, aripiprazole, azaperone, batelapine, befipiride, benperidol, benzindopyrine, bimithil, biriperone, brofoxine; bromperidol; bupropion, buspirone, butaclamol, butaperazine; carphenazine, carvotroline, cericlamine, chlorazepine, chlordiazepoxide, chlorpromazine; chlorprothixene, cinperene, cintriamide, citalopram, clomacran, clonazopam, clopenthixol, clopimozide, clopipazan, cloroperone, clothiapine, clothixamide, clozapine; cyclophenazine, dapiprazole, dapoxetine, desipramine, divalproex, dipyridamole, doxepin, droperidol, duloxetine, eltoprazine, eptipirone, etazolate, fenimide, fibanserin, flucindole, flumezapine, fluoxetine, fluphenazine, fluspiperone, fluspirilene, flutroline, fluvoxamine, gepione, gevotroline, halopemide, haloperidol, hydroxyzine, hydroxynortriptyline, iloperidone, imidoline, lamotrigine, loxapine, enperone, mazapertine, mephobarbital, meprobamate, mesoridazine, mesoridazine, milnacipran, mirtazapine, metiapine, milenperone, milipertine, molindone, nafadotride, naranol, nefazodone, neflumozide, ocaperidone, odapipam, olanzapine, oxethiazine, oxiperomide, pagoclone, paliperidone, paroxitene, penfluridol, pentiapine perphenazine, phenelzine, pimozide, pinoxepin, pipamperone, piperacetazine, pipotiazine, piquindone, pilindole, pivagabine, pramipexole, prochlorperazine, prochlorperazine, promazine, quetiapine, reboxetine, remoxipride, remoxipride, risperidone, rimcazole, robolzotan, selegiline, seperidol, sertraline, sertindole; septiline, setoperone, spiperone, sunipitron, tepiindole, thioridazine, thiothixene, tiapride, tioperidone, tiospione, topiramate, tranylcypromine, trifluoperazine, trifluperidol, triflupromazine, triflupromazine, kimipramine, venlafaxine, ziprasidone and their salts.

Examples of sedatives, hypnotics and tranquilisers are bromazepam, buspione, clazolam, clobazam, chlorazepate, diazepam, demoxepam, dexmedetomitine, diphenyhydramine, doxylamine, enciprazine, estrazolam, hydroxyzine, ketazolam, lorazatone, lorazepam, loxapine, medazepam, meperidine, methobarbital, midazolam, nabilone, nisobamate, oxazepam, pentobarbital, promethazine, propofol, triazolam, zalelplon, zolpidem and their salts. Examples of drugs used for treatment of skin ailments are acitretin, alclometasone, allitretinoin, betamethasone, calciprotrine, chlorhexidine, clobetasol, clocortolone, clotriamozole, collagenase, cyclosporin, desonide, difluorosone, doxepine, eflornithine, finasteride, fluocinolone, flurandrenolide, fluticasone, halobetasol, hydrochloroquine, hydroquinone, hydroxyzine, ketoconazole, mafenide, malathion, menobenzone, neostigmine, nystatin, podoflox, povidone, tazorotene, tretinoin and their salts.

Examples of steroids and hormones are alclometasone, betamethasone, calcitonin, cikorelix, clobetasol, clocortolone, cortisones, danazol, desmopressin, desonide, desogestrel, desoximetasone, dexamethasone, diflorasone, estradiol, estrogens, estropipate, ethynlestradiol, i fluocinolone, flurandrenolide, fluticasone, glucagon, gonadotropin, goserelin, halobetasol, hydrocortisone, leuprolide, levonorgestrel, levothyroxine, medroxyprogesterone, menotropins, methylprednisolone, methyltestosterone, mometasone, naferelin, norditropin, norethindrone, norgestrel, octreolide, oxandrolone, oxymetholone, polytropin, prednicarbate, prednisolone, progesterone, sermorelin, somatropin, stanozolol, testosterone, urofollitropin and their salts.

Example of agents that are susceptible to the gastric environment such as proton pump inhibitors are pantoprazole, omeprazole, lansoprazole, esomeprazole, rabeprazole, pariprazole, leminoprazole, or an enantiomer, isomer, derivative, free base or salt thereof; lipid-lowering agents such as lovastatin, pravastatin, atorvastatin, simvastatin; agents that are targeted to the intestine for local action such as 5-aminosalicylic acid, corticosteroids such as beclomethasone, budesonide, fluticasone, tixocortol useful in treating Crohn's disease and ulcerative colitis; agents that may be inactivated by the gastric contents such as enzymes like pancreatin, antibiotics such as erythromycin; agents that cause bleeding or irritation of the gastric mucosa such as aspirin, steroids, nonsteroidal anti-inflammatory compounds like ibuprofen, naproxen, ketoprofen, fenoprofen, flurbiprofen, oxaprozin, diflunisal, diclofenac, indomethacin, tolmetin, sulindac, etodolac, acetaminophen, platelet inhibitors such as abciximab, intergrelin, dipyridamole; nucleoside analogs such as didanosine, transfer factor preparations, hormones, insulin, and other agents that have decreased stability in the gastric environment, as well as agents that are required for local action in the latter part of the gastrointestinal Tact. The agents may be used as their base or as their pharmaceutically acceptable salt or solvate thereof.

The treatment can be via oral administration, transmucosal administration, buccal administration, nasal administration, inhalation, parental administration, intravenous, subcutaneous, intramuscular, sublingual, transdermal administration, and rectal administration. Nasal administration is a preferred mode in the present invention. Nasal administration may delay or obviate drug resistance that may occur through the other routes of administration, such as, oral or parentral.

Effective Dosages

Pharmaceutical compositions suitable for use in the present invention include compositions wherein the active ingredient is contained in a therapeutically or prophylactically effective amount, i.e., in an amount effective to achieve therapeutic or prophylactic benefit. Of course, the actual amount effective for a particular application will depend, inter alia, on the condition being treated and the route of administration. Determination of an effective amount is well within the capabilities of those skilled in the art, especially in light of the disclosure herein.

Therapeutically effective amounts for use in humans can be determined from animal models. For example, a dose for humans can be formulated to achieve circulating concentration that has been found to be effective in animals. The amount administered can be the same amount administered to treat a particular disease or can be an amount lower than the amount administered to treat that particular disease. Patient doses for oral administration of the drug may range from about 1 μg-1 gm/day. The dosage may be administered once per day or several or multiple times per day. The amount of the drug administered to practice methods of the present invention will of course, be dependent on the subject being treated, the severity of the affliction, the manner of administration and the judgment of the prescribing physician. The dose used to practice the invention can produce the desired therapeutic or prophylactic effects, without producing serious side effects.

Routes of Administration

The methods of treatment in the invention include by way of example only, oral administration, transmucosal administration, buccal administration, nasal administration such as inhalation, parental administration, intravenous, subcutaneous, intramuscular, sublingual, transdermal administration, and rectal administration.

In some embodiments of the present invention, the method of treatment is by nasal administration or inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

In some embodiments of the present invention, the method of treatment is by oral administration. Oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the method of treatment of the present invention to provide tablets that disintegrate when exposed to an aqueous environment. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed. A solubilizer may also be added to increase the solubility of the hydrophilic drug and/or other components, such as surfactants, or to maintain the composition as a stable or homogeneous solution or dispersion.

Mixtures of solubilizers may be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The compositions for the treatment can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

The compositions for delivery can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

In some embodiments of the present invention, the method of treatment can be transdermal. Transdermal patches may be used to provide continuous or discontinuous infusion in controlled amounts, either with or without therapeutic agent. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions may also be prepared with one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Kits

Figure 3:
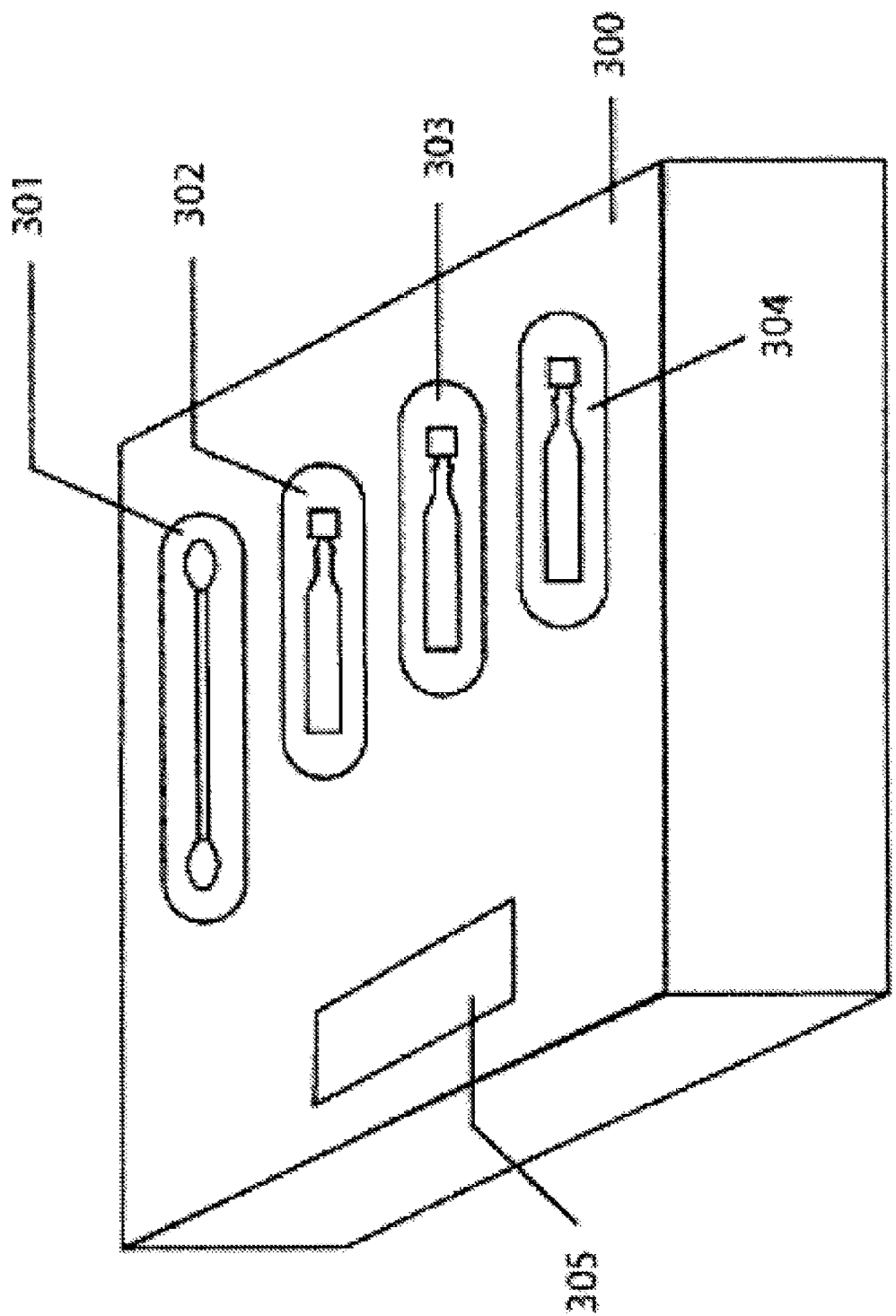
FIG. 3 depicts a kit for a detection of biological substance in a nasal specimen.

The invention also provides kits. As shown in FIG. 3, by way of example only, the kit 300 may include a sterile nasal swab 301 for collection of nasal secretions, an elongated storage and transport tube 302 for receiving the swab wherein the tube can be glass or plastic and the tube may have a replaceable end closure, and contain a sterile nutrient medium for isolation of the nasal secretions, a sterile assay solution 303 for addition to the transport tube, and a detector medium 304 for the detection of a biological substance in the nasal secretion. The kit may also include written instructions 305. In some embodiments, the therapeutic agent can also be provided as separate compositions in separate containers within the kit for the treatment. Suitable packaging and additional articles for use (e.g., measuring cup for liquid preparations, foil wrapping to minimize exposure to air, and the like) are known in the art and may be included in the kit.

The following preparations and examples serve to illustrate the invention. They should not be construed as narrowing it, or limiting its scope.

EXAMPLES

Example 1

PCR Analysis of a Specimen of Nasal Mucus

Figure 4:
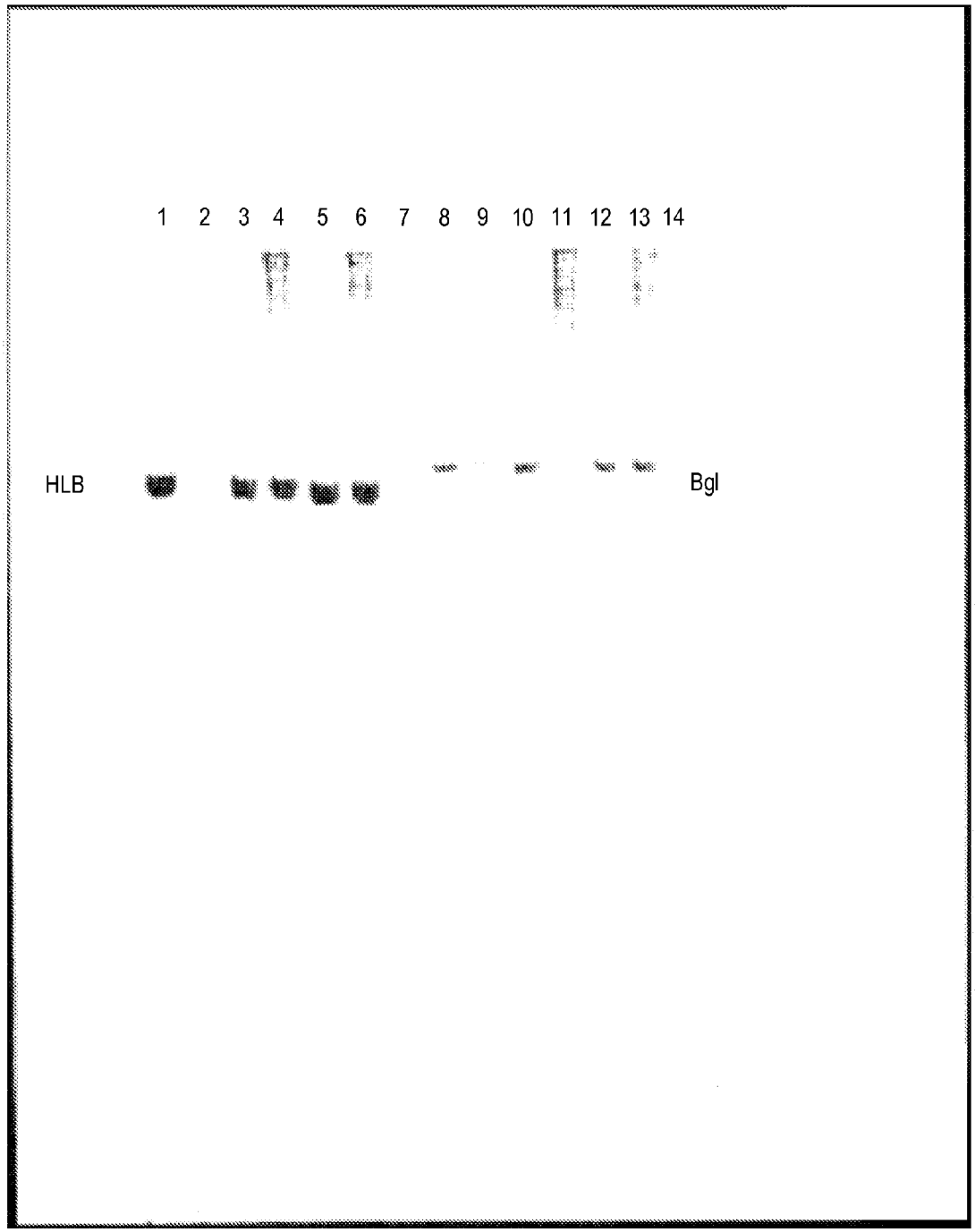
FIG. 4 depicts a polyacrylamide gel electrophoresis of samples as shown in Table 1.

Specimen of nasal mucus from different subjects was collected and analyzed using PCR. FIG. 4 depicts a polyacrylamide gel electrophoresis of samples as shown in Table 1. Lanes 1-7 in FIG. 4 reveal one major band consistent with the presence of HLA. Lanes 8-14 reveal one major band consistent with the presence of β globin. On the right are located molecular weight markers of various KD.

TABLE 1

Results of PCR analysis of two samples of nasal mucus obtained from normal subjects

| Rot. Pos. | Sample Name | Rep. of... | Sample Type* | Known Conc. | Tm1 (° C.) | Area 1 (Units) | Tm2 (° C.) | Area 2 (Units) | Tm3 (° C.) | Area 3 (Units) Ethidium Bromide | Sample Comments |
|---|---|---|---|---|---|---|---|---|---|---|---|
| 1 | WB Pos Cont | | U | | 84.05 | 11.18 | | | | POS | HLA |
| 2 | R. Blk | | U | | 82.08 | 10.96 | | | | NEG | HLA |
| 3 | Specimen # 1 | | U | | 83.91 | 9.602 | | | | POS | HLA |
| 4 | Specimen # 2 | | U | | 84.74 | 10.86 | | | | POS | HLA |
| 5 | Specimen # 1 + Pos Cont | | U | | 83.40 | 7.006 | | | | POS | HLA |
| 6 | Specimen # 1 + Pos Cont | | U | | 84.63 | 8.658 | | | | POS | HLA |
| 7 | R. Blk | | U | | 80.68 | 5.131 | | | | NEG | HLA |
| 8 | WB Pos Cont | | U | | 87.41 | 6.062 | | | | POS | beta globin |
| 9 | R. Blk | | U | | 75.92 | 6.166 | | | | POS | beta globin |
| 10 | Specimen # 1 | | U | | 86.97 | 7.534 | | | | POS | beta globin |
| 11 | Specimen # 2 | | U | | 76.91 | 5.492 | 86.91 | 8.009 | | POS | beta globin |
| 12 | Specimen # 1 + Pos Cont | | U | | 86.81 | 7.983 | | | | POS | beta globin |
| 13 | Specimen # 1 + Pos Cont | | U | | 86.54 | 7.451 | | | | POS | beta globin |
| 14 | R. Blk | | U | | | | | | | NEG | beta globin |

*P = Positive, U = Unknown, N = Negative, S = Standard, <> = De-Selected

Example 2

DNA Extraction Procedure from Body Fluids with QIAGEN Kit

All specimens and all reagents were equilibrated to room temperature. 20 µl Qiagen Protease (or proteinase K) was pipetted into the bottom of a 1.5 ml centrifuge tube. 200 µl of specimen (nasal mucus, plasma, saliva, urine and other biological fluids) was added to the centrifuge tube. In case of specimens containing less than 1 µg of DNA or RNA, 5-10 µg of carrier DNA or RNA (20 µl of poly dA or 8 µl of poly [C]) was added. 200 µl of AL buffer was added to the tube. Mixture was mixed by pulse-vortexing for 15 sec. Mixture was incubated at 56-60° C. for 15 min. Mixture was vortexed and centrifuged briefly. 200 µl of ethanol (96-100%) was added to the tube. Mixture was vortexed and centrifuged briefly. The mixture was carefully applied to a QIAamp spin column (in a 2 ml collection tube) without wetting the rim. Caps of the columns were closed and the mixture was centrifuged for 1 min. The spin column was placed in another clean collection tube and the tube containing the filtrate was discarded. 500 µl of buffer AW1 was added to the spin column, the lid was closed and the column was spun for 1 min. The column was placed in another clean collection tube and the tube containing the filtrate was discarded. 500 µl of buffer AW2 was added to the spin column, the lid was closed and the column was spun at for 3 minutes; the collection tube containing the filtrate was discarded. Since trace amounts of buffer AW2 inhibit PCR, complete removal of the buffer is desirable. The column is then placed in a clean 1.5 ml centrifuge tube and 50 µl of $H_2O$ was added to it. It was incubated at room temperature for 15 minutes and centrifuged for 3 minutes. The resulting DNA solution can be stored at 4° C. for several months.

Example 3

LightCycler Data Analysis Report

TABLE 2

LightCycler Melting Analysis Report of Studies on each of two samples of nasal mucus analyzed by PCR

| Program: | denature | | | Type: | None | Cycles | 1 |
|---|---|---|---|---|---|---|---|
| Segment Number | Temperature Target (° C.) | Hold Time (sec) | Slope (° C.)/sec) | 2° Target Temp (° C.) | Step Size (° C.) | Step Delay (Cycles) | Acquisition Mode |
| 1 | 95 | 600 | 20 | 0 | 0 | 0 | None |
| Program: | PCR | | | Type: | Quantification | Cycles | 45 |
| Segment Number | Temperature Target (° C.) | Hold Time (sec) | Slope (° C.)/sec) | 2° Target Temp (° C.) | Step Size (° C.) | Step Delay (Cycles) | Acquisition Mode |
| 1 | 95 | 10 | 20 | 0 | 0 | 0 | None |
| 2 | 58 | 15 | 20 | 0 | 0 | 0 | None |
| 3 | 72 | 12 | 20 | 0 | 0 | 0 | Single |

TABLE 2-continued

LightCycler Melting Analysis Report of Studies on each of two samples of nasal mucus analyzed by PCR

| Program: | melt | | | Type: | None | Cycles | 1 |
|---|---|---|---|---|---|---|---|
| Segment Number | Temperature Target (° C.) | Hold Time (sec) | Slope (° C.)/sec) | 2° Target Temp (° C.) | Step Size (° C.) | Step Delay (Cycles) | Acquisition Mode |
| 1 | 95 | 0 | 20 | 0 | 0 | 0 | None |
| 2 | 50 | 60 | 20 | 0 | 0 | 0 | None |
| 3 | 95 | 0 | 0.2 | 0 | 0 | 0 | Continuous |

| Program: | cool | | | Type | None | Cycles | 1 |
|---|---|---|---|---|---|---|---|
| Segment Number | Temperature Target (° C.) | Hold Time (sec) | Slope (° C.)/sec) | 2° Target Temp (° C.) | Step Size (° C.) | Step Delay (Cycles) | Acquisition Mode |
| 1 | 40 | 30 | 20 | 0 | 0 | 0 | None |

| Fluorescence Settings | | | |
|---|---|---|---|
| LED Power | CALIB | Display Mode | 3.5 Compatible |
| Color Compensation | N/A | | |
| | N/A | | |
| Car. Movement | Continuous | | |

| Melting Analysis Settings | | | |
|---|---|---|---|
| Channel Setting | F1/1 | | |
| Program Name | melt | | |
| Start Time | 0:52:39.85 | Stop Time | 0:56:28.2 |

Figure 5:
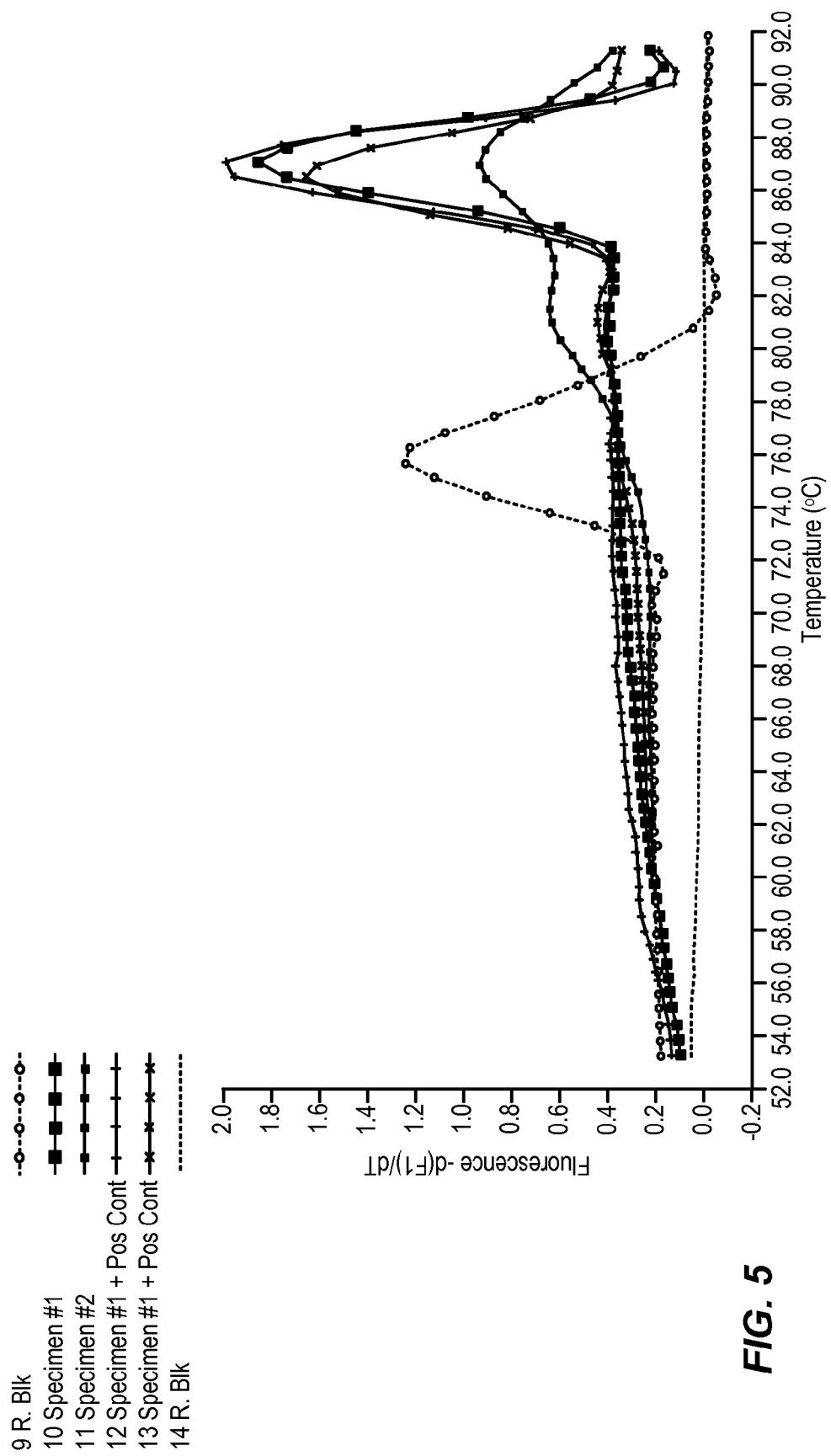
FIG. 5 depict LightCycler melting peak report on results of PCR analysis of two samples of nasal mucus. Fluorescence is plotted on ordinate, temperature on abscissa.
Figure 6:
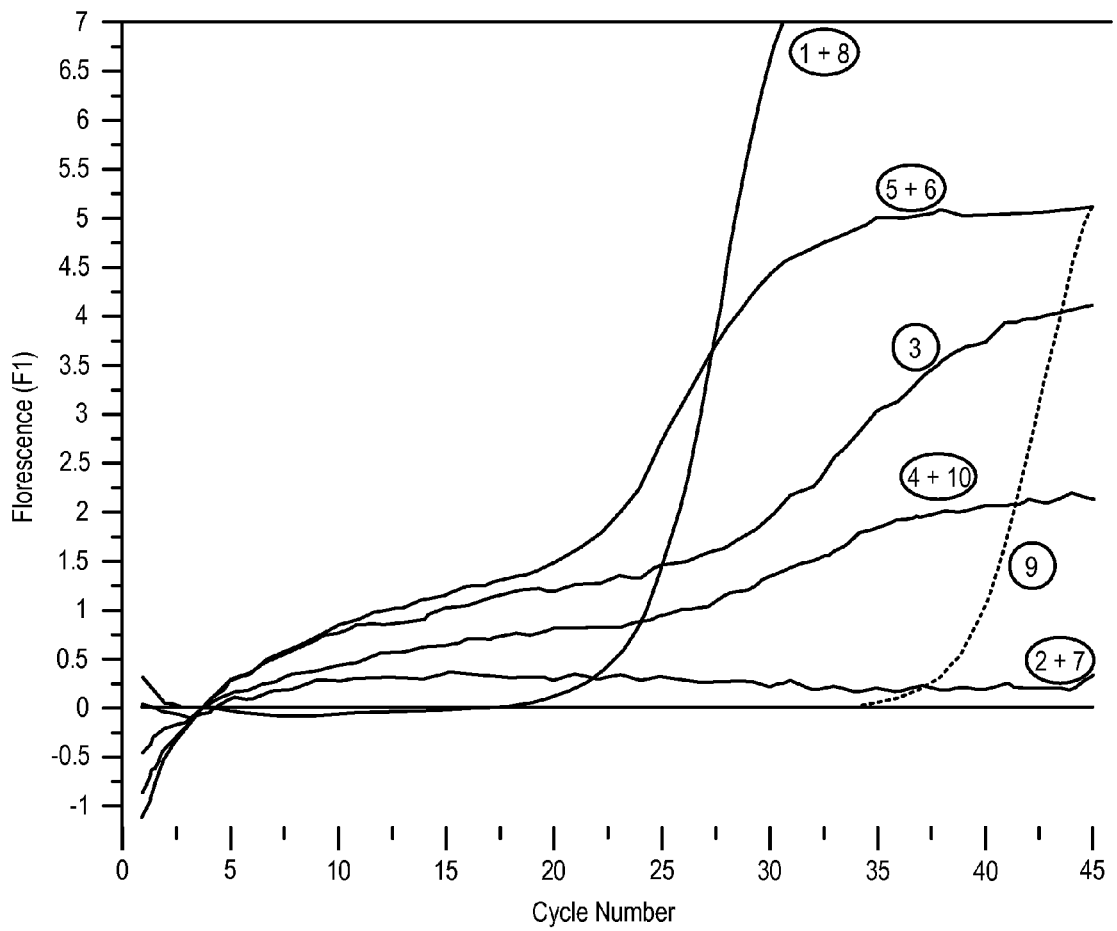
FIG. 6 depicts LightCycler data analysis report on results of PCR analysis of two samples of nasal mucus. Fluorescence is plotted on ordinate, cycle number on abscissa.
Figure 7:
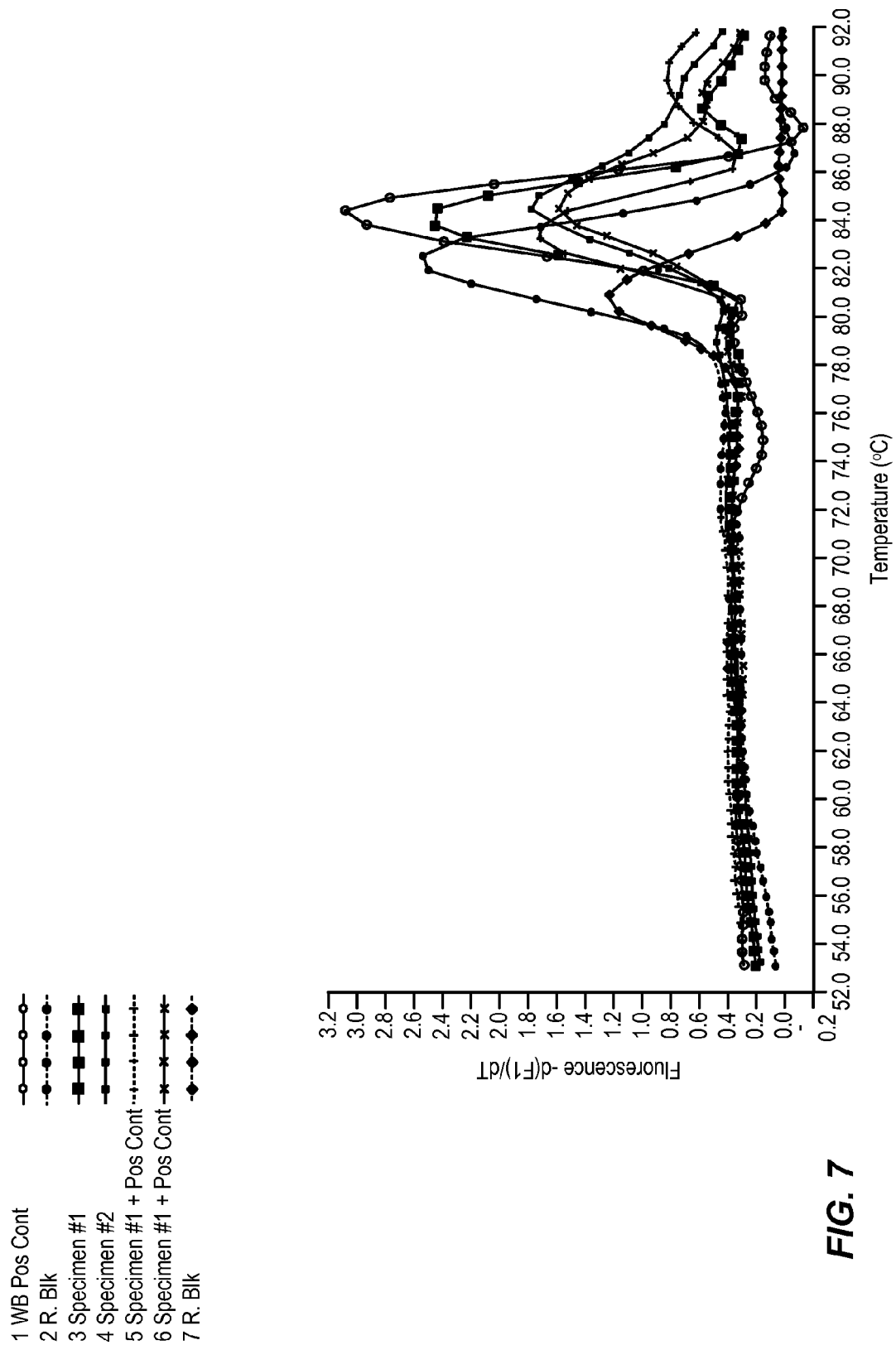
FIG. 7 depicts LightCycler melting peak report on results of PCR analysis of two samples of nasal mucus. Fluorescence is plotted on ordinate, temperature on abscissa.
Figure 8:
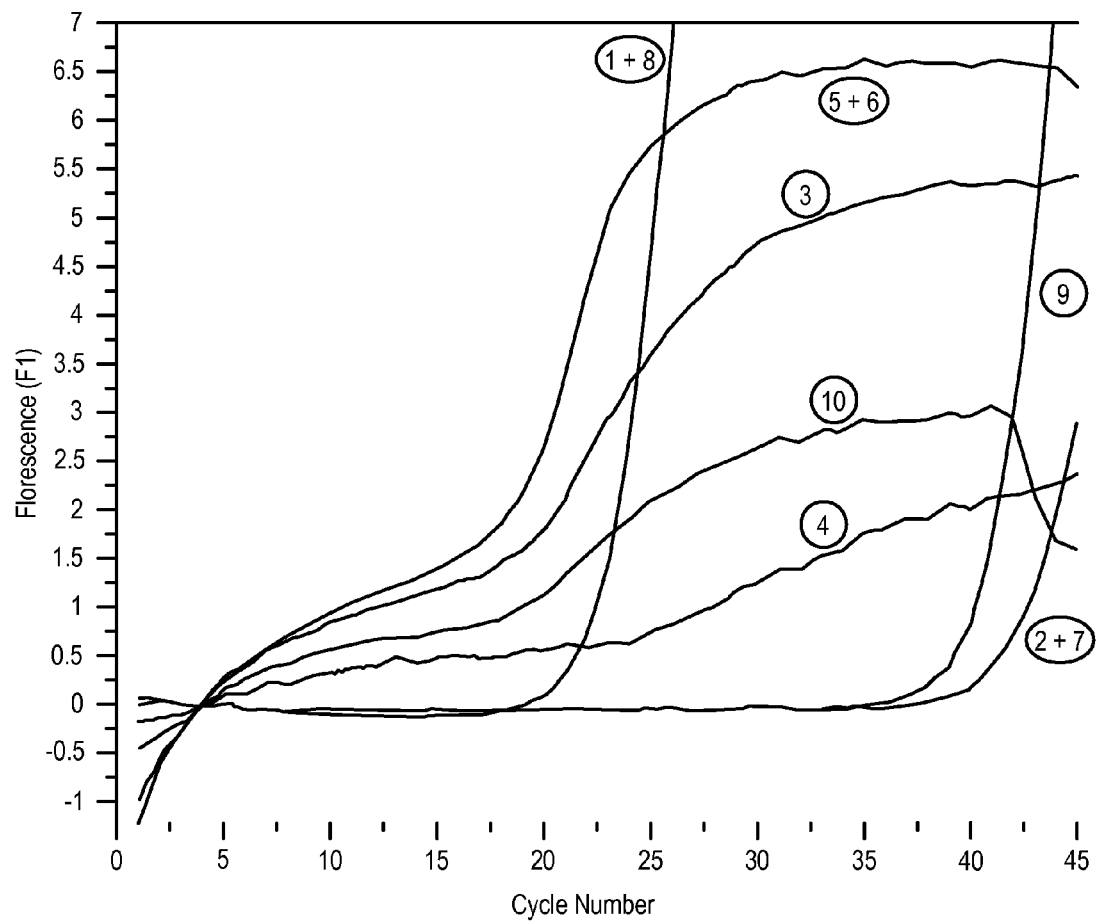
FIG. 8 depicts LightCycler data analysis report on results of PCR analysis of two samples of nasal mucus. Fluorescence is platted on ordinate, cycle number on abscissa.
Figure 9:
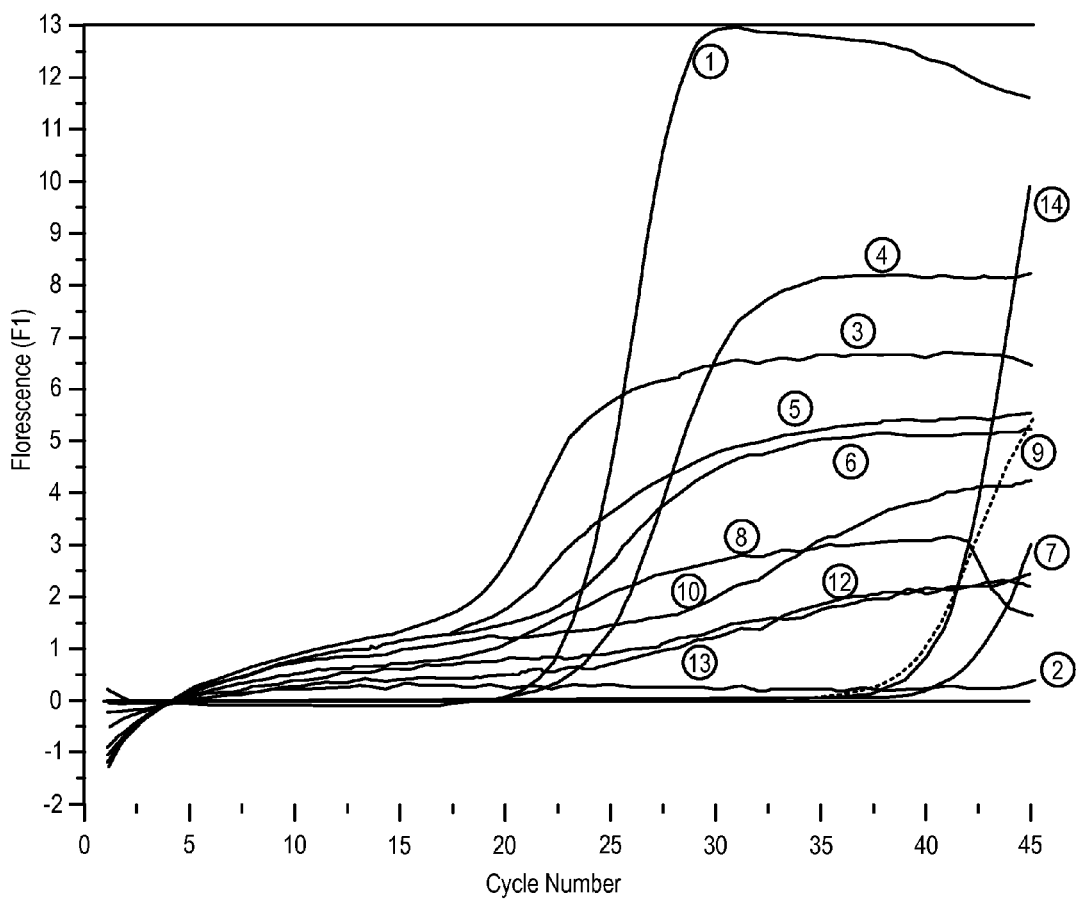
FIG. 9 depicts LightCycler data analysis report on results of PCR analysis of two samples of nasal mucus. Fluorescence is plotted on ordinate, cycle number on abscissa.

FIG. 5 depicts LightCycler melting peak report on results of PCR analysis of two samples of nasal mucus. Fluorescence is plotted on ordinate, temperature on abscissa. FIG. 6 depicts LightCycler data analysis report on results of PCR analysis of two samples of nasal mucus. Fluorescence is plotted on ordinate, cycle number on abscissa. FIG. 7 depicts LightCycler melting peak report on results of PCR analysis of two samples of nasal mucus. Fluorescence is plotted on ordinate, temperature on abscissa. FIG. 8 depicts LightCycler data analysis report on results of PCR analysis of two samples of nasal mucus. Fluorescence is platted on ordinate, cycle number on abscissa. FIG. 9 depicts LightCycler data analysis report on results of PCR analysis of two samples of nasal mucus. Fluorescence is plotted on ordinate, cycle number on abscissa.

Example 4

Analysis of Nasal Mucus Before and after Fasting

Table 3 depicts the results of the ELISA analysis of nasal mucus collected from 49 subjects before (fasting) and after (non-fasting). FL/VOL is flow rate in ml/min, PROT is protein, LEP is leptin, LEP/PR is leptin/protein, AG is agouti related protein, AG/PR is agouti related protein/protein, INS is insulin, INS/PR is insulin/protein, X is mean values of 49 subjects, and SD is standard deviation of results.

TABLE 3

| | Nasal mucus (nM) | | | | | | | |
|---|---|---|---|---|---|---|---|---|
| SUBJECT | BEFORE FL/VOL ml/min | AFTER FL/VOL ml/min | BEFORE PROT mg/ml | AFTER PROT mg/ml | BEFORE LEP pg/ml | AFTER LEP pg/ml | BEFORE LEP/PR ratio | AFTER LEP/PR ratio |
| 1 | 6.52 | | 2.198 | | 496 | | 226 | |
| 2 | 0.81 | | 2.771 | | | 90 | | |
| 3 | 0.31 | | 2.016 | | | 39 | | |
| 4 | 3.27 | | 2.494 | | | | | |
| 5 | 4.64 | | 2.811 | | 724 | | 258 | |
| 6 | 0.28 | 4.03 | 3.237 | 2.419 | 197 | | 61 | |
| 7 | 49.31 | 29.68 | 2.886 | 2.805 | 510 | 382 | 177 | 136 |
| 8 | 5.18 | | 3.272 | | | | | |
| 9 | 22.37 | 4.76 | 1.751 | 1.999 | | | | |
| 10 | | 3 | | 1.653 | | | | |
| 11 | 0.39 | | 3.865 | | 56 | | 14 | |
| 12 | 3.83 | | 1.192 | | | | | |
| 13 | | 18.38 | | 3.047 | | 230 | | 75 |
| 14 | 0.27 | | | | 2365 | | | |
| 15 | 1.37 | | 2.834 | | | | | |
| 16 | | 8.36 | | 2.252 | | 34 | | 15 |
| 17 | | 9.9 | | 2.644 | | 28 | | 11 |
| 18 | 29.13 | 21.63 | 3.859 | 3.093 | 45 | 51 | 12 | 16 |

TABLE 3-continued

| SUBJECT | Nasal mucus (nM) | | | | | | | |
|---|---|---|---|---|---|---|---|---|
| 19 | 2.93 | | 1.584 | | 18 | | 11 | |
| 20 | 1.32 | | 2.114 | | | | | |
| 21 | 5.84 | | 2.068 | | | | | |
| 22 | 5.94 | 1.63 | 2.16 | 2.673 | 107 | | 50 | |
| 23 | 3 | | 3.22 | | | | | |
| 24 | 2.72 | | 2.246 | | 39 | | 17 | |
| 25 | 3.87 | 4.87 | 2.28 | 2.339 | 39 | | 17 | |
| 26 | 1.99 | | 2.707 | | 174 | | 64 | |
| 27 | 27.24 | | 2.845 | | 85 | | 30 | |
| 28 | 3 | | 2.362 | | 79 | | 33 | |
| 29 | 2.21 | | 1.14 | | | | | |
| 30 | | 1.11 | | 3.226 | | | | |
| 31 | 5.59 | | 2.39 | | | | | |
| 32 | 6.77 | | | 2.811 | | 129 | | 46 |
| 33 | 0.55 | | 3.122 | | 388 | | 124 | |
| 34 | | 1.02 | | 2.062 | | 56 | | 27 |
| 35 | 23.8 | | 1.665 | | 56 | | 34 | |
| 36 | 1.13 | | 2.92 | | 225 | | 77 | |
| 37 | | 1.27 | | 1.323 | | 39 | | 29 |
| 38 | | 3.33 | | 3.537 | | 45 | | 13 |
| 39 | | 6.39 | | 1.901 | | 287 | | 151 |
| 40 | | 1.27 | | 1.356 | | 135 | | 100 |
| 41 | 1.22 | | 2.379 | | 183 | | 77 | |
| 42 | 3.35 | 2.72 | 2.609 | 2.892 | 73 | 107 | 28 | 37 |
| 43 | 10.23 | | 1.123 | | 124 | | 110 | |
| 44 | 13.07 | 10.58 | 3.531 | 1.74 | 540 | 1265 | 153 | 727 |
| 45 | 4.15 | | 2.552 | | 22 | | 9 | |
| 46 | 2.76 | 3.83 | 3.012 | 3.859 | 107 | 124 | 36 | 32 |
| 47 | 3.34 | | 3.37 | | 143 | | 42 | |
| 48 | 10.42 | 3.23 | 3.335 | 2.419 | 104 | 56 | 31 | 23 |
| 49 | | 1.09 | | 2.016 | | | | |
| X | 7.21 | 6.77 | 2.55 | 2.46 | 276.0 | 182.2 | 70.5 | 95.9 |
| SD | 10.23 | 7.65 | 0.71 | 0.68 | 475.0 | 296.1 | 69.7 | 180.3 |

| SUBJECT | BEFORE AG pg/ml | AFTER AG pg/ml | BEFORE AG/PR | AFTER AG/PR | BEFORE INS μIU/ml | AFTER INS μIU/ml | BEFORE INS/PR | AFTER INS/PR |
|---|---|---|---|---|---|---|---|---|
| 1 | 1 | | 0 | | 22 | | 10 | |
| 2 | | | | | | | | |
| 3 | | | | | | | | |
| 4 | 7 | | 3 | | 10 | | 4 | |
| 5 | 7 | | 2 | | 7 | | 2 | |
| 6 | 1 | 8 | 0 | 3 | 5 | 16 | 2 | 7 |
| 7 | | | | | 13 | 7 | 5 | 2 |
| 8 | 7 | | 2 | | 31 | | 9 | |
| 9 | | 2 | | 1 | 15 | 5 | 9 | 3 |
| 10 | | 7 | | 4 | | 23 | | 14 |
| 11 | 6 | | 2 | | 8 | | 2 | |
| 12 | 1 | | 1 | | 6 | | 5 | |
| 13 | | 4 | | 1 | | 10 | | 3 |
| 14 | | | | | | | | |
| 15 | 5 | | 2 | | 1 | | 0 | |
| 16 | | | | | | | | |
| 17 | | | | | | | | |
| 18 | 9 | 11 | 2 | 4 | 4 | 12 | 1 | 4 |
| 19 | 2 | | 1 | | 19 | | 12 | |
| 20 | 8 | | 4 | | 11 | | 5 | |
| 21 | 3.5 | | 2 | | 15 | | 7 | |
| 22 | 3 | 2 | 1 | 1 | 11 | 16 | 5 | 6 |
| 23 | 7 | | 2 | | 9 | | 3 | |
| 24 | 7 | | 3 | | 8 | | 4 | |
| 25 | 21 | 8 | 9 | 3 | 43 | 48 | 19 | 21 |
| 26 | 5 | | 2 | | 9 | | 3 | |
| 27 | 7 | | 2 | | 9 | | 3 | |
| 28 | 7 | | 3 | | 43 | | 18 | |
| 29 | 9 | | 8 | | 8 | | 7 | |
| 30 | | 8 | | 2 | | 31 | | 10 |
| 31 | 7 | | 3 | | 74 | | 31 | |
| 32 | | | | | | | | |
| 33 | 1 | | 0 | | 95 | | 30 | |
| 34 | | | | | | | | |
| 35 | 3 | | 2 | | 13 | | 8 | |
| 36 | 8 | | 3 | | 19 | | 7 | |
| 37 | | | | | | | | |
| 38 | | | | | | | | |
| 39 | | 6 | | 3 | | | | |
| 40 | | 6 | | 4 | | 27 | | 20 |

TABLE 3-continued

| | | | Nasal mucus (nM) | | | | | |
|---|---|---|---|---|---|---|---|---|
| 41 | 0 | | 0 | | 25 | | 11 | |
| 42 | 2 | 9 | 1 | 3 | 4 | 12 | 2 | 4 |
| 43 | 3 | | 3 | | 2 | | 2 | |
| 44 | | 2 | | 1 | 51 | 24 | 14 | 14 |
| 45 | | | | | 16 | | 6 | |
| 46 | 6 | 10 | 2 | 3 | 14 | 15 | 5 | 4 |
| 47 | 7 | | 2 | | 10 | | 3 | |
| 48 | 4 | 3 | 1 | 1 | 4 | 6 | 1 | 2 |
| 49 | | 6 | | 3 | | | | |
| X | 5.5 | 6.1 | 2.3 | 2.6 | 18.6 | 18.0 | 7.5 | 8.1 |
| SD | 4.0 | 3.0 | 1.9 | 1.2 | 20.6 | 11.8 | 7.5 | 6.4 |

Example 5

Analysis of Saliva Before and after Fasting

Table 4 depicts the results of the ELISA analysis of saliva collected from 50 subjects before (fasting) and after (non-fasting). FL/VOL is flow rate in ml/min, PROT is protein, LEP is leptin, LEP/PR is leptin/protein, AG is agouti related protein, AG/PR is agouti related protein/protein, INS is insulin, INS/PR is insulin/protein, X is mean values of 50 subjects, and SD is standard deviation of results.

TABLE 4

| | Saliva | | | | | | | |
|---|---|---|---|---|---|---|---|---|
| SUBJECT | BEFORE FL/VOL ml/min | AFTER FL/VOL ml/min | BEFORE PROT mg/ml | AFTER PROT mg/ml | BEFORE LEP pg/ml | AFTER LEP pg/ml | BEFORE LEP/PR | AFTER LEP/PR |
| 1 | 0.456 | | 2.483 | | 10 | | 4.03 | |
| 2 | | 0.61 | | 2.546 | | 7 | | 2.75 |
| 3 | | 0.673 | | 2.684 | | 6 | | 2.24 |
| 4 | 0.406 | | 1.941 | | | | | |
| 5 | 0.717 | | 3.623 | | 24 | | 6.62 | |
| 6 | 0.447 | 0.405 | 2.523 | 2.886 | 17 | | 6.74 | |
| 7 | 0.572 | 1.119 | 3.946 | 3.491 | 2 | 4 | 0.51 | 1.15 |
| 8 | 0.405 | | 3.473 | | | | | |
| 9 | | 0.315 | 2.817 | 2.177 | | | | |
| 10 | | 0.377 | | 2.39 | | | | |
| 11 | 0.84 | | 3.197 | | 12 | | 3.75 | |
| 12 | 0.635 | | 3.594 | | 10 | | 2.78 | |
| 13 | | 0.721 | | 3.306 | | 8 | | 2.42 |
| 14 | 0.908 | | 3.433 | | 5 | | 1.46 | |
| 15 | 0.908 | | 3.277 | | | | | |
| 16 | | 0.523 | | 3.508 | | 5 | | 1.43 |
| 17 | | 0.5 | | 2.85 | | 6 | | 2.11 |
| 18 | 0.633 | 0.722 | 3.214 | 3.254 | 6 | 15 | 1.87 | 4.61 |
| 19 | 0.356 | | 3.3 | | 19 | | 5.76 | |
| 20 | 0.734 | | 1.855 | | 7 | | 3.77 | |
| 21 | 0.692 | | 3.398 | | | | | |
| 22 | 0.584 | | 3.646 | | | | | |
| 23 | 1.211 | 0.705 | 3.145 | 3.295 | 11 | | 3.50 | |
| 24 | 0.601 | | 2.483 | | | | | |
| 25 | 0.634 | | 1.377 | | 12 | | 8.71 | |
| 26 | 0.347 | 0.372 | 2.736 | 2.932 | 16 | | 5.85 | |
| 27 | 0.356 | | 2.413 | | 6 | | 2.49 | |
| 28 | 0.559 | | 3.012 | | 23 | | 7.64 | |
| 29 | 0.871 | | 3.076 | | 20 | | 6.50 | |
| 30 | 0.722 | | 2.091 | | | | | |
| 31 | | 0.946 | | 3.819 | | | | |
| 32 | 0.355 | | 2.989 | | | | | |
| 33 | | 0.496 | | 3.669 | | 11 | | 3.00 |
| 34 | 0.569 | | 3.456 | | 16 | | 4.63 | |
| 35 | | 0.34 | | 3.358 | | 12 | | 3.57 |
| 36 | 0.766 | | 2.033 | | 15 | | 7.38 | |
| 37 | 0.969 | | 3.024 | | 6 | | 1.98 | |
| 38 | | 0.824 | | 3.427 | | 22 | | 6.42 |
| 39 | | 0.624 | | 2.31 | | 7 | | 3.03 |
| 40 | | 0.71 | | 1.711 | | 3 | | 1.75 |
| 41 | | 0.905 | | 2.644 | | 8 | | 3.03 |
| 42 | 0.511 | | 2.483 | | 25 | | 10.07 | |
| 43 | 0.524 | 0.614 | 2.776 | 3.56 | 7 | 10 | 2.52 | 2.81 |
| 44 | 0.533 | | 3.185 | | 6 | | 1.88 | |
| 45 | 0.596 | 0.566 | 3.963 | 3.128 | 6 | 7 | 1.51 | 2.24 |
| 46 | 0.806 | | 2.068 | | 7 | | 3.38 | |

TABLE 4-continued

| | | | Saliva | | | | | |
|---|---|---|---|---|---|---|---|---|
| 47 | 1.041 | 0.908 | 3.295 | 2.748 | 11 | 17 | 3.34 | 6.19 |
| 48 | 0.714 | | 2.863 | | 0 | | 0.00 | |
| 49 | 0.524 | 0.631 | 3.4 | 2.638 | 10 | 19 | 2.94 | 7.20 |
| 50 | | 0.841 | | 2.65 | | | | |
| X | 0.64 | 0.64 | 2.93 | 2.96 | 11.4 | 9.8 | 4.1 | 3.3 |
| SD | 0.21 | 0.21 | 0.62 | 0.53 | 6.7 | 5.5 | 2.6 | 1.8 |

| SUBJECT | BEFORE AG pg/ml | AFTER AG pg/ml | BEFORE AG/PR | AFTER AG/PR | BEFORE INS μIU/ml | AFTER INS μIU/ml | BEFORE INS/PR | AFTER INS/PR |
|---|---|---|---|---|---|---|---|---|
| 1 | 15 | | 6.04 | | 17 | | 6.85 | |
| 2 | | | | | | | | |
| 3 | | | | | | | | |
| 4 | 6 | | 3.09 | | 20 | | 10.30 | |
| 5 | 8 | | 2.21 | | 21 | | 5.80 | |
| 6 | 6 | 8 | 2.38 | 2.77 | 15 | 12 | 5.95 | 4.16 |
| 7 | | | | | 9 | 9 | 2.28 | 2.58 |
| 8 | 2 | | 0.58 | | 10 | | 2.88 | |
| 9 | | 8 | | 3.67 | 6 | 4 | 2.13 | 1.84 |
| 10 | | 7 | | 2.93 | | 28 | | 11.72 |
| 11 | 15 | | 4.69 | | 11 | | 3.44 | |
| 12 | 7 | | 1.95 | | 15 | | 4.17 | |
| 13 | | 2 | | 0.60 | | 19 | | 5.75 |
| 14 | | | | | 79 | | | |
| 15 | 13 | | 3.97 | | 27 | | | |
| 16 | | | | | | | | |
| 17 | | | | | | | | |
| 18 | 4 | 5 | 1.24 | 1.54 | 20 | 11 | 6.22 | 3.38 |
| 19 | 31 | | 9.39 | | 7 | | 2.12 | |
| 20 | | | | | 25 | | 13.48 | |
| 21 | 10 | | 2.94 | | 10 | | 2.94 | |
| 22 | 46 | | 12.62 | | 43 | | 11.79 | |
| 23 | 6 | 8 | 1.91 | 2.43 | 13 | 2 | 4.13 | 0.61 |
| 24 | 8 | | 3.22 | | 20 | | 8.05 | |
| 25 | 7 | | 5.08 | | 27 | | 19.61 | |
| 26 | 10 | 7 | 3.65 | 2.39 | 9 | 2 | 3.29 | 0.68 |
| 27 | 5 | | 2.07 | | 9 | | 3.73 | |
| 28 | 8 | | 2.66 | | 17 | | 5.64 | |
| 29 | 7 | | 2.28 | | 12 | | 3.90 | |
| 30 | 10 | | 4.78 | | 44 | | 21.04 | |
| 31 | | 4 | | 1.05 | | 27 | | 7.07 |
| 32 | 5 | | 1.67 | | 23 | | 7.69 | |
| 33 | | | | | | | | |
| 34 | | | | | 22 | | 6.37 | |
| 35 | | | | | | | | |
| 36 | 12 | | 5.90 | | 11 | | 5.41 | |
| 37 | 7 | | 2.31 | | 5 | | 1.65 | |
| 38 | | | | | | | | |
| 39 | | | | | | | | |
| 40 | | 10 | | 5.84 | | | | |
| 41 | | 5 | | 1.89 | | 13 | | 4.92 |
| 42 | 10 | | 4.03 | | 13 | | 5.24 | |
| 43 | 23 | 5 | 8.29 | 1.40 | 25 | 7 | 9.01 | 1.97 |
| 44 | 8 | | 2.51 | | 4 | | 1.26 | |
| 45 | | 5 | | 1.60 | 17 | 7 | 4.29 | 2.24 |
| 46 | | | | | 15 | | 7.25 | |
| 47 | 7 | 5 | 2.12 | 1.82 | 3 | 11 | 0.91 | 4.00 |
| 48 | 11 | | 3.84 | | 19 | | 6.64 | |
| 49 | 3 | 14 | 0.88 | 5.31 | 21 | 3 | 6.18 | 1.14 |
| 50 | | 7 | | 2.64 | | | | |
| X | 10.7 | 6.7 | 3.7 | 2.5 | 18.4 | 11.1 | 6.2 | 3.7 |
| SD | 9.0 | 2.8 | 2.7 | 1.5 | 13.9 | 8.4 | 4.6 | 3.0 |

Example 6

Analysis of Plasma Before and after Fasting

Table 5 depicts the results of the ELISA analysis of plasma collected in 20 subjects before (fasting) and after (non-fasting). PROT is protein in mg/dl, LEP is leptin, LEP/PR is leptin/protein, AG is agouti related protein, AG/PR is agouti related protein/protein, INS is insulin, INS/PR is insulin/protein, X is mean values of 20 subjects, and SD is standard deviation of result.

TABLE 5

| | | | | | | | | | | | | | | |
|---|---|---|---|---|---|---|---|---|---|---|---|---|---|---|
| | | | | | | | Plasma | | | | | | | |
| SUBJECT | BEFORE PROT mg/ml | AFTER PROT mg/ml | BEFORE LEP pg/ml | AFTER LEP pg/ml | BEFORE LEP/PR | AFTER LEP/PR | BEFORE AG pg/ml | AFTER AG pg/ml | BEFORE AG/PR | AFTER AG/PR | BEFORE INS μIU/ml | AFTER INS μIU/ml | BEFORE INS/PR | AFTER INS/PR |
| 1 | | 7.8 | | | | | | 35 | | 4 | | 55 | | 7 |
| 2 | | 7.2 | | | | | | | | | | 38 | | 5 |
| 3 | | 7.7 | | | | | | 37 | | 5 | | 36 | | 5 |
| 4 | | 8.6 | | | | | | 61 | | 7 | | 46 | | 5 |
| 5 | 7.9 | | 10661 | | 1349 | | 30 | | 4 | | 3 | | 0 | |
| 6 | | 6.5 | | 5345 | | | | 51 | | 8 | | 1 | | 0 |
| 7 | 6.9 | | | | | | | 51 | | 7 | | 17 | | 2 |
| 8 | 7.6 | | | | | | | 38 | | 5 | | | | |
| 9 | 7.9 | | | | | | | 34 | | 4 | | 41 | | 5 |
| 10 | | 7.4 | | | | | | 28 | | 4 | | 6 | | 1 |
| 11 | 7.1 | | | | | | | 53 | | 7 | | | | |
| 12 | 6.2 | 6.2 | 1793 | 1714 | 289 | 276 | 65 | | 10 | | 95 | 60 | 15 | 10 |
| 13 | 7.2 | | 5075 | | 705 | | 25 | | 3 | | 4 | | 1 | |
| 14 | | 7.2 | | | | | | 70 | | 10 | | 24 | | 3 |
| 15 | | 6.6 | | | | | | 34 | | 5 | | | | |
| 16 | | 7.2 | | 16860 | | 2342 | | 55 | | 8 | | 44 | | 6 |
| 17 | | 7.9 | | 16860 | | 2134 | | 33 | | 4 | | 1 | | 0 |
| 18 | | 7.3 | | 15826 | | 2168 | | 37 | | 5 | | 7 | | 1 |
| 19 | | 7.3 | | | | | | 37 | | 5 | | 18 | | 2 |
| 20 | | 6.6 | | | | | | 58 | | 9 | | | | |
| X | 7 | 7 | 5843 | 11321 | 781 | 1730 | 42 | 45 | 6 | 6 | 32 | 28 | 5 | 4 |
| SD | 1 | 1 | 4484 | 7240 | 534 | 973 | 14 | 14 | 3 | 2 | 38 | 21 | 6 | 3 |

Example 7

Analysis of Insulin Concentration in Nasal Mucus, Plasma, and Saliva

Specimens of nasal mucus from different subjects were collected and analyzed using ELISA. Table 6 depicts detection and measurement of human insulin in nasal mucus as compared to insulin in blood plasma and saliva under several physiological and pathological processes. In control subjects, in the fasting state, insulin concentrations were similar in each biological fluid measured. In the non-fasting state, the nasal mucus concentrations were significantly lower than in plasma or saliva. In obese subjects and in diabetics, in the fasting state, insulin concentrations were similar in plasma and nasal mucus but slightly elevated in saliva. However, in the non-fasting state, insulin concentrations increased in plasma and saliva in response to increased carbohydrate intake but in nasal mucus, insulin levels decreased.

TABLE 6

Insulin in plasma, saliva, and nasal mucus

| | AGE (years) | WEIGHT (lbs) | PLASMA GLUCOSE mg/ml | PLASMA μIU/ml | SALIVA μIU/ml | NASAL MUCUS μIU/ml |
|---|---|---|---|---|---|---|
| SUBJECTS | | | | | | |
| CONTROLS (56) | 56 ± 2 | 174 ± 8 | | | | |
| FASTING | | | 88 ± 1 | 17.1 ± 3.7 | 18.9 ± 2.3 | 19.0 ± 2.2 |
| NON-FASTING | | | 174 ± 8 | 29.4 ± 4.4 | 22.6 ± 2.6 | 7.5 ± 0.9[c] |
| SUBJECTS (11) | | | | | | |
| OBESE | 51 ± 6 | 259 ± 26 | | | | |
| FASTING | | | 110 ± 24 | 20.0 ± 6.2[†] | 34.1 ± 7.9 | 18.4 ± 6.5 |
| NON-FASTING | | | 259 ± 26 | 38.2 ± 11.7 | 36.3 ± 6.3 | 7.5 ± 2.6[dba] |
| DIABETES | 51 ± 6 | 243 ± 52 | | | | |
| FASTING | | | 142 ± 37 | 22.7 ± 10.2 | 36.8 ± 9.0 | 21.0 ± 9.3 |
| NON-FASTING | | | 243 ± 42 | 39.5 ± 19.0 | 38.2 ± 9.6 | 7.6 ± 2.3[b] |

( ) Subject number
[†]MEAN ± SEM
[a]$p < 0.01$ with respect to non-fasting saliva
[b]$p < 0.005$ with respect to fasting saliva
[c]$p < 0.001$ with respect to fasting nasal mucus and non-fasting plasma, saliva
[d]$p < 0.05$ with respect to fasting plasma, non-fasting plasma
[e]$p < 0.02$ with respect to fasting plasma

Example 8

Analysis of Insulin Receptor Concentration in Nasal Mucus, Plasma, and Saliva Table 7 depicts the detection and measurement of human insulin receptor in nasal mucus as compared to the insulin receptor in plasma and saliva under several physiological and pathological conditions. In control subjects in the fasting state, insulin receptor concentrations measured were similar in plasma, saliva as well as nasal mucus. However, in the non-fasting state, where there was little change in receptor concentrations in plasma or saliva, there was a significant decrease in nasal mucus receptor concentration. In obese subjects and in diabetics, in the fasting state, insulin receptor concentrations decreased in each biological fluid measured. However, in the non-fasting state, there were no further decreases in receptor concentrations in plasma or in saliva but there was a decrease in receptor concentration in nasal mucus associated with an increase in carbohydrate intake.

as venipucture. Its presence in nasal mucus may also offer a view into other aspects of both human physiology and pathology. In the non-fasting state insulin receptor concentration is down regulated to some extent under some conditions but is uniformly regulated in nasal mucus indicating that, its concentration in nasal mucus may indicate physiological phenomenon such as, appetite and brain, and the signal characteristics reflecting base human physiology and pathology. Its presence may influence human immune and autoimmune responses.

Example 9

Pearson-Product-Moment Correlations of Insulin with Plasma Glucose and Insulin with Weight Table 8 depicts Pearson-product-moment correlations of insulin with plasma glucose and insulin with weight. There was little positive correlation among controls in insulin in plasma or insulin in saliva, in either the fasting or non-fasting

TABLE 7

| | AGE (years) | WEIGHT (lbs) | PLASMA GLUCOSE mg/ml | PLASMA mg/ml | SALIVA mg/ml | NASAL MUCUS mg/ml |
|---|---|---|---|---|---|---|
| Insulin receptor concentration in plasma, saliva, and nasal mucus | | | | | | |
| SUBJECTS (56) | | | | | | |
| CONTROLS (56) | $56 \pm 2^\dagger$ | $174 \pm 8$ | $84 \pm 1^\$$ | | | |
| FASTING | | | $88 \pm 6$ | $8.7 \pm 1.8^\dagger$ | $7.6 \pm 0.7$ | $8.5 \pm 1.7$ |
| NON-FASTING | | | $174 \pm 8$ | $7.5 \pm 1.4$ | $7.6 \pm 0.6$ | $3.2 \pm 0.6^a$ |
| SUBJECTS (11) | | | | | | |
| OBESE | $51 \pm 6^\ddagger$ | $259 \pm 26$ | | | | |
| FASTING | | | $110 + 24\$$ | $2.9 \pm 0.9^{\dagger b}$ | $6.0 \pm 1.2$ | $4.8 \pm 0.6^d$ |
| NON-FASTING | | | $259 + 26$ | $3.0 \pm 0.3^b$ | $5.2 \pm 0.8^c$ | $2.1 \pm 0.5$ |
| THIN | | $122 \pm 6$ | | | | |
| FASTING | | | | | $8.4 \pm 2.7$ | |
| NON-FASTING | | | | | $9.4 \pm 4.6$ | |
| DIABETES (4) | | $243 \pm 52$ | | | | |
| FASTING | | | $142 \pm 37$ | $4.0 \pm 1.7^b$ | $4.0 \pm 0.6^c$ | $4.7 \pm 1.9$ |
| NON-FASTING | | | $243 \pm 42$ | $3.4 \pm 0.6^a$ | $4.6 \pm 1.9$ | $2.3 \pm 1.6$ |

[†] MEAN ± SEM
[‡] years
[$] mg/dl
[a] $p < 0.01$ with respect to nasal mucus fasting, plasma (fasting, non-fasting), saliva (fasting, non-fasting)
[b] $p < 0.005$ with respect to controls
[c] $p < 0.001$ with respect to controls
[d] $p < 0.05$ with respect to controls These results in Tables 6 and 7 indicate that the characteristics of nasal mucus reflect physiological and pathological conditions. The detection of the presence of insulin or insulin receptors in nasal mucus may offer an alternative method for diagnosis of diabetes, other disorders of carbohydrate metabolism and physiological measurements of insulin and insulin receptors. Its ease of measurement using a non-invasive technique may be preferable to invasive techniques such state. However, in nasal mucus this correlation was negative, indicating a down regulated direction. This signal in nasal mucus may reflect a control mechanism of appetite. Thus, in nasal mucus there may be substances which reflect both physiological parameters common or uncommon to blood or saliva which provides methods to diagnose body physiological and pathological events.

TABLE 8

Correlation (pearson product moment (r)) between insulin and independent variable (N = 60)

| | INSULIN CONCENTRATION | | | | | |
|---|---|---|---|---|---|---|
| | PLASMA (r) | | SALIVA (r) | | NASAL MUCUS (r) | |
| | FASTING | NON-FASTING | FASTING | NON-FASTING | FASTING | NON-FASTING |
| VARIABLE (CONTROLS) | | | | | | |
| PLASMA GLUCOSE (mg/dl) | 0.16 | 0.08 | 0.25 | 0.26 | −0.20 | −0.14 |
| WEIGHT (lbs) | 0.04 | 0.24 | 0.26 | 0.38 | −0.14 | −0.18 |
| VARIABLE (OBESE) | | | | | | |
| PLASMA GLUCOSE (mg/dl) | 0.87 | −0.01 | 0.33 | 0.39 | −0.30 | −0.37 |
| WEIGHT (lbs) | 0.62 | 0.72 | 0.08 | 0.65 | −0.44 | −0.55 |
| VARIABLE (DIABETES) | | | | | | |
| PLASMA GLUCOSE (mg/dl) | 1.00[a] | 1.00[a] | 0.65 | 0.59 | −0.26 | −0.64 |
| WEIGHT (lbs) | 1.00 | 0.99[a] | 0.69 | 0.69 | −0.28 | −0.66 |

[a] $p < 0.01$

Example 10

Pearson-Product-Moment Correlations of Insulin Receptor with Plasma Glucose and Insulin Receptor with Weight Table 9 depicts relationships between insulin receptor concentration with plasma glucose and weight. There was little positive correlation among controls amongst insulin receptors in plasma or insulin receptors in saliva, in either the fasting or non-fasting state. However, in nasal mucus this correlation was negative, indicating a down regulated direction. This signal in nasal mucus may reflect a control mechanism of appetite. Thus, in nasal mucus there may be substances which reflect both physiological parameters common or uncommon to blood or saliva which may provide methods to diagnose body physiological and pathological events.

TABLE 9

Correlation (pearson product moment (r)) between insulin receptor concentration and independent variable (n = 60)

| | INSULIN RECEPTOR CONCENTRATION | | | | | |
|---|---|---|---|---|---|---|
| | PLASMA (r) | | SALIVA (r) | | NASAL MUCUS (r) | |
| | FASTING | NON-FASTING | FASTING | NON-FASTING | FASTING | NON-FASTING |
| VARIABLE (CONTROLS) | | | | | | |
| PLASMA GLUCOSE (mg/dl) | 0.20 | 0.12 | −0.24 | −0.14 | 0.03 | 0.11 |
| WEIGHT (lbs) | −0.11 | −0.07 | −0.08 | −0.19 | −0.21 | −0.17 |
| VARIABLE (OBESE) | | | | | | |
| PLASMA GLUCOSE (mg/dl) | 0.70 | 0.20 | −0.51 | −0.08 | 0.41 | 0.19 |
| WEIGHT (lbs) | −0.18 | −0.33 | 0.09 | −0.16 | 0.24 | −0.09 |
| VARIABLE (DIABETES) | | | | | | |
| PLASMA GLUCOSE (mg/dl) | −0.57 | −0.43 | −0.78 | 0.25 | 0.15 | −0.22 |
| WEIGHT (lbs) | −0.60 | −0.52 | 0.56 | −0.34 | 0.18 | −0.19 |

Example 11

Analysis of Caspase 3 in Nasal Mucus and Saliva

Caspase 3 is one of the apoptotic substances involved in the apoptotic process. Table 10 illustrates a comparison between the detection and measurement of caspase 3 in nasal mucus and in saliva in 18 subjects. The presence of caspase in nasal mucus is about 13% of that in saliva and reflects the magnitude of the apoptotic process. The presence of caspase in nasal mucus indicates the activity of cellular death in both physiological and pathological processes.

TABLE 10

Caspase 3 in human saliva and nasal mucus

| | SALIVA | | | NASAL MUCUS | | |
|---|---|---|---|---|---|---|
| Subjects | CASPASE 3 µg/ml | PROTEIN mg/dl | CASPASE 3 PROTEIN | CASPASE 3 µg/ml | PROTEIN mg/dl | CASPASE 3 PROTEIN |
| 18 | 2.87 ± 0.70[†] | 2.7 ± 0.2 | 2.88 ± 0.28 | 0.38 ± 0.13 | 2.2 ± 0.2 | 0.38 ± 0.17 |

[†]MEAN ± SEM

Example 12

Analysis of TNFα in Nasal Mucus and Saliva

Table 11 illustrates detection and measurement of TNFα in nasal mucus and saliva in 75 subjects. Results indicate that TNFα in nasal mucus is about 30 times higher than in saliva. Elevated levels of this substance in nasal mucus in diverse disease processes makes their diagnosis possible on a clinical basis since obtaining cellular diagnosis through tissue biopsy can not only be invasive but also difficult and at times dangerous. The concentration of TNFα in nasal mucus can be reflective of underlying disease processes and is easier to obtain. These results may make the use of this fluid an important method of diagnosis for these pathological processes which cannot be as conveniently made in plasma. These data suggest that various cancers can be diagnosed by measurements of TNFα in nasal mucus and their treatment can be monitored by following its concentration in nasal mucus. Since levels of TNFα may also reflect the inflammatory aspects of disease processes inducing it, use of anti TNFα drugs through nasal administration may reflect a method of treating these various disease processes. Concentrations of TNFα in nasal mucus in patients with smell loss can be greater than for example, 5000 times that found in normal subjects thereby reflecting its function as a "death protein" indicator of excessive apoptosis as in its role in cancer.

TABLE 11

TNFα in human saliva and nasal mucus

| | SALIVA | | | NASAL MUCUS | | |
|---|---|---|---|---|---|---|
| Subjects | TNFα µg/ml | PROTEIN mg/dl | TNFα PROTEIN | TNFα µg/ml | PROTEIN mg/dl | TNFα PROTEIN |
| 75 | 0.43 ± 0.03[†] | 3.1 ± 0.1 | 0.15 ± 0.01 | 12.8 ± 1.6[a] | 2.4 ± 0.09[a] | 5.5 ± 1.3[a] |

[†] MEAN ± SEM
With respect to saliva
[a] $p < 0.001$

Example 13

Analysis of TNFR I in Nasal Mucus and Saliva

Table 12 illustrates detection and measurement of TNFR I in 47 subjects. Results indicate that TNFR I in nasal mucus is about 16 times its concentration in saliva and its concentration is significantly increased over that found in plasma, red blood cells, or urine. The results show that TNFR I present in nasal mucus can reflect activity of many inflammatory, oncological and other pathological processes, including taste and smell dysfunction. Thus the methods of the present invention can be used to detect and establish clinical diagnoses of excessive apoptosis and can be used as a treatment modality in inhibiting pathological apoptosis.

TABLE 12

TNF receptor I in human saliva and nasal mucus

| | SALIVA | | | NASAL MUCUS | | |
|---|---|---|---|---|---|---|
| Subjects | TNFR I µg/ml | PROTEIN mg/dl | TNFR I PROTEIN | TNFR I µg/ml | PROTEIN mg/dl | TNFR I PROTEIN |
| 47 | 110 ± 13[†] | 3.1 ± 0.1 | 38 ± 5 | 1753 ± 357[a] | 2.2 ± 0.1[a] | 837 ± 161[a] |

[†]MEAN ± SEM
With respect to saliva
[a]$p < 0.001$

Example 14

Analysis of TNFR II in Nasal Mucus and Saliva

Table 13 illustrates detection and measurement of TNFR II in 47 subjects. Results indicate that TNFR II in nasal mucus is about 24 times its concentration in saliva and its concentration in nasal mucus is significantly higher than found in plasma, red blood cells, or urine. The results reflect that TNFR II present in nasal mucus provides a non invasive method of diagnosing various pathological processes. Thus the methods of the present invention can be used to detect and establish clinical diagnoses of excessive apoptosis and can be used as a treatment modality in inhibiting pathological apoptosis.

TABLE 13

TNF receptor II in human saliva and nasal mucus

| | SALIVA | | | NASAL MUCUS | | |
|---|---|---|---|---|---|---|
| Subjects | TNFR II µg/ml | PROTEIN mg/dl | TNFR II PROTEIN | TNFR II µg/ml | PROTEIN mg/dl | TNFR II PROTEIN |
| 47 | 48 ± 2[†] | 3.1 ± 0.1 | 17 ± 0.9 | 1126 ± 217[a] | 2.2 ± 0.1[a] | 578 ± 128[a] |

[†]MEAN ± SEM
With respect to saliva
[a]$p < 0.001$

Example 15

Analysis of TRAIL in Nasal Mucus and Saliva

Tables 14 and 15 illustrate detection and measurement of TRAIL in saliva and nasal mucus in normal subjects and in patients with smell loss. In Table 14, results indicate that TRAIL in nasal mucus is about 5 times higher than in saliva and both are significantly higher than in blood, red blood cells, or urine. TRAIL in nasal mucus in some patients with smell and taste loss varies from 500-10,000 times higher than in normal subjects and it may be elevated in nasal mucus in patients with inflammatory and oncological disease processes. Mean levels of increased TRAIL in nasal mucus reveal levels significantly greater than in other fluids. The results provide a non-invasive method for detecting TRAIL in nasal mucus.

TABLE 14

Trail in saliva and nasal mucus in normal subjects and in patients with smell loss

| | SALIVA | | | NASAL MUCUS | | |
|---|---|---|---|---|---|---|
| SUBJECTS (Number) | TRAIL µg/ml | PROTEIN mg/dl | TRAIL PROTEIN | TRAIL µg/ml | PROTEIN mg/dl | TRAIL PROTEIN |
| NORMALS (17) | 336 ± 48[†] | 2.7 ± 0.1 | 122 ± 14 | 1639 ± 89 | 2.2 ± 0.01 | 770 ± 35 |
| PATIENTS (10) | 353 ± 31 | 2.7 ± 0.2 | 141 ± 20 | 2584 ± 430 | 1.4 ± 0.2 | 4753 ± 1400 |

[†]MEAN ± SEM

TABLE 15

Trail in saliva and nasal mucus in normal subjects and in patients with Hyposmia

| SUBJECTS (Number) | SALIVA | | | | NASAL MUCUS | | |
|---|---|---|---|---|---|---|---|
| | PROTEIN mg/dl | TRAIL μg/ml | FLOW RATE ml/sec | TRAIL FLOW RATE | PROTEIN mg/dl | TRAIL μg/ml | TRAIL PROTEIN |
| NORMALS (28) | 2.29 ± 0.10[†] | 123 ± 6 | 0.80 ± 0.03 | 343 ± 13 | 2.65 ± 0.12 | 1990 ± 119 | 7.56 ± 28 |
| PATIENTS (65) | 2.96 ± 0.09 | 330 ± 25[a] | 0.63 ± 0.03 | 582 ± 55[a] | 1.97 ± 0.11 | 4121 ± 54[a] | 3095 ± 591[a] |

( ) Subject number
[†]Mean ± SEM
[a]$p < 0.001$ with respect to normal

Example 16

Analysis of TRAIL in Nasal Mucus in Patients with Hyposmia Before and after Treatment with Theophylline Table 16 illustrates detection and measurement of TRAIL in nasal mucus in patients with hyposmia before and after treatment with theophylline at various doses. Data indicate that treatment with theophylline which returned smell function to normal in a dose-dependent manner was associated with a dose-dependent decrease in TRAIL, which indicates a decrease in the abnormal apoptotic processes. These data indicate both a biochemical and functional improvement in smell function by treatment with theophylline.

TABLE 16

Nasal mucus Trail in patients with hyposmia before and after treatment with theophylline at various doses

| | PRETREATMENT | | THEOPHYLLINE TREATMENT | | | | | |
|---|---|---|---|---|---|---|---|---|
| | | | 200 mg | | 400 mg | | 600 mg | |
| SUBJECTS (Number) | TRAIL μg/ml | PROTEIN mg/dl | TRAIL μg/ml | PROTEIN mg/dl | TRAIL μg/ml | PROTEIN mg/dl | TRAIL μg/ml | PROTEIN mg/dl |
| PATIENTS (5) | 2584 | 1.36 | 855 | 1.29 | 791 | 2.06 | 247 | 2.00 |
| NORMALS (9) | 335 | | | | | | | |

[†]MEAN ± SEM

Example 17

Analysis of IL2 in Saliva and Nasal Mucus

Table 17 illustrates levels of IL2 in human nasal mucus and saliva. IL2 was not present in nasal mucus although it was found in plasma.

TABLE 17

IL 2 in human saliva and nasal mucus

| SUB-JECTS (Number) | SALIVA | | | NASAL MUCUS | | |
|---|---|---|---|---|---|---|
| | IL 2 μg/ml | PROTEIN mg/dl | IL 2 PROTEIN | IL 2 μg/ml | PROTEIN mg/dl | IL 2 PROTEIN |
| (10) | 0 | 3.1 ± 0.2[†] | 0 | 0 | 2.2 ± 0.1 | 0 |

[†]MEAN ± SEM

Example 18

Analysis of IL3 in Saliva and Nasal Mucus

Table 18 illustrates measured IL 3 in both human saliva and nasal mucus. Levels of IL 3 in nasal mucus were found to be about ½ the concentration in saliva but both levels were higher than that found in plasma, red blood cells, or urine. IL 3 present in nasal mucus provides a non invasive method of diagnosing various IL3 related diseases.

TABLE 18

IL 3 in human saliva and nasal mucus

| SUBJECTS (Number) | SALIVA | | | NASAL MUCUS | | |
|---|---|---|---|---|---|---|
| | IL 3 µg/ml | PROTEIN mg/dl | IL 3 PROTEIN | IL 3 µg/ml | PROTEIN mg/dl | IL 3 PROTEIN |
| (17) | 140 ± 32[†] | 3.1 ± 0.2 | 48 ± 15 | 63 ± 24 | 2.2 ± 0.1 | 43 ± 12 |

[†]MEAN ± SEM

Example 19

Analysis of Endostatin in Human Plasma, Urine, Saliva and Nasal Mucus

Table 19 illustrates detection and measurement of endostatin in plasma, urine, saliva and nasal mucus in 15 subjects. Endostatin levels in nasal mucus were 5 times higher than in saliva and about 7% of that found in plasma. On the basis of the endostatin/protein ratio, levels in nasal mucus are about 14% of that found in plasma. Presence of this 20 KD protein in nasal mucus illustrates a non-invasive method of detection of endostatin in nasal mucus and its use in diagnosing various endostatin related diseases. It may also be indicative of its synthesis in nasal mucus.

TABLE 19

Endostatin in human plasma, urine, saliva and nasal mucus

| BIOLOGICAL FLUIDS (15) | ENDOSTATIN µg/ml | PROTEIN mg/dl | ENDOSTATIN PROTEIN |
|---|---|---|---|
| PLASMA | 94 ± 10[†] | 6.9 ± 0.10 | 15 ± 1 |
| URINE | 0.5 ± 0.04[a] | — | — |
| SALIVA | 1.3 ± 0.3[a] | 2.6 ± 0.2 | 0.59 ± 0.04[a] |
| NASAL MUCUS | 6.6 ± 1.3[a] | 3.0 ± 0.2 | 2.0 ± 0.43[a] |

( ) Subject number
[†]MEAN ± SEM
[a]$p < 0.001$ with respect to plasma

Example 20

Analysis of Erythropoetin (EPO) in Plasma, Urine, Saliva and Nasal Mucus

Table 20 illustrates detection and measurement of EPO in plasma, urine, saliva and nasal mucus. EPO was not found in urine or saliva. The level of EPO in nasal mucus was found to be between 1.1 and 4.5 times higher than in plasma. Presence of EPO in nasal mucus illustrates a non-invasive method of detection of EPO in nasal mucus and its use in diagnosing various EPO related diseases.

TABLE 20

EPO in plasma, urine, saliva and nasal mucus

| BIOLOGICAL FLUIDS (27) | ERYTHRO-POETIN µIU/ml | PROTEIN mg/dl | ERYTHRO-POETIN PROTEIN |
|---|---|---|---|
| PLASMA | 13 ± 2[†] | 7.2 ± 0.1 | 2 ± 0.3 |
| URINE | 0 | 0 | 0 |

TABLE 20-continued

EPO in plasma, urine, saliva and nasal mucus

| BIOLOGICAL FLUIDS (27) | ERYTHRO-POETIN µIU/ml | PROTEIN mg/dl | ERYTHRO-POETIN PROTEIN |
|---|---|---|---|
| SALIVA | 0 | 0 | 0 |
| NASAL MUCUS | 15 ± 5 | 2.9 ± 0.1[a] | 9 ± 2[b] |

( ) Subject number
[†]MEAN ± SEM
[a]$p < 0.001$ with respect to plasma
[b]$p < 0.005$ with respect to plasma

Example 21

Analysis of Bone Morphogenic Protein (BMP) in Plasma, Urine, Saliva and Nasal Mucus Table 21 illustrates detection and measurement of BMP I in plasma, urine, saliva and nasal mucus in 20 subjects. BMP I was found in plasma but not in urine, saliva or nasal mucus.

TABLE 21

BMP in plasma, urine, saliva and nasal mucus

| BIOLOGICAL FLUIDS (20) | BMP µg/ml | PROTEIN mg/dl | BMP PROTEIN |
|---|---|---|---|
| PLASMA | 30 ± 6[†] | 3.6 ± 0.5 | 0 |
| URINE | 0 | 0 | 0 |
| SALIVA | 0 | 0 | 0 |
| NASAL MUCUS | 0 | 0 | 0 |

( ) Subject number
[†]MEAN ± SEM

Example 22

Analysis of Brain Derived Neurotrophic Factor (BDNF) in Human Plasma, Urine, Saliva and Nasal Mucus Table 22 illustrates detection and measurement of BDNF in plasma, urine, saliva and nasal mucus in 20 subjects. BDNF was found in plasma and nasal mucus but not in urine or saliva. Levels of BDNF in plasma were higher than in nasal mucus. The results indicate that nasal mucus may be a repository of the family of nerve growth factors and the concentration of BDNF as shown in Table 22, may help understand both the physiology and pathology of neurotrophic factors related to growth and homeostasis of cells in the nasal cavity as well as reporting on the presence of these factors in the systemic circulation.

TABLE 22

BDNF in human plasma, urine, saliva and nasal mucus

| BIOLOGICAL FLUIDS | (20) | BDNF μg/ml | PROTEIN mg/dl | BDNF PROTEIN |
|---|---|---|---|---|
| PLASMA | | 3391 ± 530 | 7.1 ± 0.01 | 447 ± 74 |
| URINE | | 0 | — | — |
| SALIVA | | 0 | 2.7 ± 0.2 | |
| NASAL MUCUS | | 11 ± 7 | 3.2 ± 0.3 | 8 ± 6 |

( ) Subject number
†MEAN ± SEM

Example 23

Analysis of Ciliary Neurotrophic Factor (CNTF) in Human Plasma, Urine, Saliva and Nasal Mucus Table 23 illustrates detection and measurement of CNTF in plasma, urine, saliva and nasal mucus in 19 subjects. Levels of CNTF in plasma and nasal mucus were found to be similar but lower in saliva. These results indicate that measurement of CNTF in nasal mucus may be used as an index for the levels of CNTF in plasma. The results provide a non-invasive method for the detection of CNTF in nasal mucus. The detection of CNTF in nasal mucus provides a non invasive method of diagnosing various CNTF related diseases.

TABLE 23

CNTF in human plasma, urine, saliva and nasal mucus

| BIOLOGICAL FLUIDS | (19) | CNTF μg/ml | PROTEIN mg/dl | CNTF PROTEIN |
|---|---|---|---|---|
| PLASMA | | 0.004 ± 0.001 | 3.1 ± 0.1 | 0 |
| URINE | | 0 | | |
| SALIVA | | 0.001 ± 0.001 | 3.0 ± 0.1 | 0 |
| NASAL MUCUS | | 0.003 ± 0.001 | 2.2 ± 0.1 | 0 |

( ) Subject number

Example 24

Analysis of Granulocyte Macrophage Growth Factor (GM-CSF) in Human Plasma, Urine, Saliva and Nasal Mucus Table 24 illustrates detection and measurement of GM-CSF in plasma, urine, saliva and nasal mucus in 16 subjects. Levels in nasal mucus were found to be over 6 times that found in plasma. The results provide a non-invasive method for the detection of GM-CSF in nasal mucus. The results also indicate nasal mucus to be a source of GM-CSF. The detection GM-CSF present in nasal mucus provides a non invasive method of diagnosing various GM-CSF related diseases.

TABLE 24

GM-CSF in human plasma, urine, saliva and nasal mucus

| BIOLOGICAL FLUIDS | (16) | GM-CSF μg/dl | PROTEIN mg/dl | GM-CSF PROTEIN |
|---|---|---|---|---|
| PLASMA | | 0.42 ± 0.31† | 7.2 ± 0.1 | 0.036 ± 0.034 |
| URINE | | 0 | | 0 |
| SALIVA | | 0 | | 0 |
| NASAL MUCUS | | 2.55 ± 0.8 | 2.9 ± 0.1 | 0.58 ± 0.25[a] |

( ) Subject number
†MEAN ± SEM
[a] $p < 0.001$ with respect to plasma

Example 25

Analysis of Hepatocyte Growth Factor (HGF) in Human Plasma, Urine, Saliva, and Nasal Mucus Table 25 illustrates detection and measurement of HGF in plasma, urine, saliva and nasal mucus in 17 subjects. Concentrations of HGF in nasal mucus were found to be higher than that found in either plasma or urine. These results suggest that HGF may be synthesized in the serous glands of the nose for a specific mechanism involved with nasal homeostasis as well as a mechanism involved with systemic cell migration. The results provide a non-invasive method for the detection of HGF in nasal mucus.

TABLE 25

HGF in human plasma, urine, saliva and nasal mucus

| BIOLOGICAL FLUIDS | (17) | HGF μg/ml | PROTEIN mg/dl | HGF PROTEIN |
|---|---|---|---|---|
| PLASMA | | 709 ± 91† | 3.1 ± 0.1 | 100 ± 13 |
| URINE | | 623 ± 126 | — | — |
| SALIVA | | 0 | | 0 |
| NASAL MUCUS | | 2015 ± 431[a] | 2.2 ± 0.1 | 924 ± 227[a] |

( ) Subject number
†MEAN ± SEM
With respect to plasma and urine
[a] $p < 0.001$

Example 26

Analysis of Platelet Derived Growth Factor (PDGF) in Human Plasma, Urine, Saliva and Nasal Mucus Table 26 illustrates detection and measurement of PDGF in human plasma, urine, saliva and nasal mucus in 18 subjects. Concentrations of PDGF expressed per mg protein were found to be higher in saliva and nasal mucus than in plasma. These results suggest that PDGF may be synthesized in the serous glands of the nose for a specific mechanism involved with nasal homeostasis. The results provide a non-invasive method for the detection of PDGF in nasal mucus.

TABLE 26

PDGF in human plasma, urine, saliva and nasal mucus

| BIOLOGICAL FLUIDS | (18) | PDGF μg/dl | PROTEIN mg/dl | PDGF PROTEIN |
|---|---|---|---|---|
| PLASMA | | 510 ± 153† | 6.9 ± 0.1 | 71 ± 21 |
| URINE | | 5 ± 2 | — | — |

TABLE 26-continued

PDGF in human plasma, urine, saliva and nasal mucus

| BIOLOGICAL FLUIDS | (18) | PDGF µg/dl | PROTEIN mg/dl | PDGF PROTEIN |
|---|---|---|---|---|
| SALIVA | | 600 ± 176 | 2.6 ± 0.2 | 215 ± 18[a] |
| NASAL MUCUS | | 482 ± 87 | 3.0 ± 0.2 | 175 ± 32[b] |

( ) Subject number
[†]MEAN ± SEM
[a]$p < 0.001$ with respect to plasma
[b]$p < 0.02$ with respect to plasma Example 27

Analysis of Carbonic Anhydrase VI (CA VI) Concentration

Table 27 illustrates decrease in CA VI in patients with smell and taste loss. These results provide a method for the detection and measurement of CA VI in nasal mucus as an index of smell and taste loss and its continual measurement during treatment of these disorders in order to monitor efficacy of therapy.

TABLE 27

CA VI concentrations in nasal mucus in normal subjects and in patients with smell loss

| SUB-JECTS | | PROTEIN mg/dl | ZINC µg/L | COPPER µg/L | CA VI mg/ml |
|---|---|---|---|---|---|
| NORMALS | (8) | 3.41 ± 0.02[†] | 97 ± 8 | 102 ± 8 | 0.287 ± 0.056 |
| MEN | (5) | 2.96 ± 0.30 | 100 ± 11 | 78 ± 26 | 0.238 ± 0.03 |
| WOMEN | (3) | 3.54 ± 2.04 | 90 ± 8 | 103 ± 15 | 0.369 ± 0.26 |
| PATIENTS | (70) | 2.27 ± 0.04 | | | 0.157 ± 0.13 |
| MEN | (39) | 2.21 ± 0.14[a] | 182 ± 17 | 118 ± 14 | 0.158 ± 0.020 |
| WOMEN | (31) | 2.34 ± 0.18[a] | 171 ± 21 | 126 ± 12 | 0.155 ± 0.014 |

( ) Subject number
[†]Mean ± SEM
Compared to normals
[a]$p < 0.001$

Example 28

Analysis of Loss of Smell Function by Disease Etiology

Table 28 illustrates loss of smell function by disease etiology with respect to measurements of CA VI concentration in nasal mucus. Results indicate that patients with post influenza hyposmia hypogeusia (PIHH), allergic rhinitis and post anesthesia have significantly decreased CA VI concentrations in nasal mucus. These results provide a method for the detection and measurement of CA VI in nasal mucus as an index of smell and taste loss and its continual measurement during treatment of these disorders in order to monitor efficacy of therapy. The detection of CA VI in nasal mucus provides a non invasive method of diagnosing various diseases related to human physiology and pathology.

TABLE 28

Carbonic Anhydrase VI concentrations in nasal mucus in normal subjects and in patients with smell loss

| CONDITION | | PROTEIN mg/dl | ZINC µg/L | COPPER µg/L | CA VI µg/ml |
|---|---|---|---|---|---|
| NORMALS | (11) | 3.17 ± 0.48[†] | 97 ± 7 | 102 ± 7 | 0.287 ± 0.044 |
| PIHH | (26) | 2.39 ± 0.19 | 139 ± 18[a] | 105 ± 11[a] | 0.186 ± 0.02[c] |
| ALLERGIC RHINITIS | (25) | 2.34 ± 0.19 | 234 ± 24[a] | 139 ± 20 | 0.141 ± 0.018[b] |
| POST ANESTHESIA | (6) | 1.65 ± 0.30[b] | 189 ± 60 | 139 ± 40 | 0.156 ± 0.047[c] |
| PHANTAGEUSIA | (5) | 2.30 ± 0.59 | 170 ± 49 | 158 ± 31 | 0.180 ± 0.054 |

( ) Subject number
[†]Mean ± SEM
Compared to normals
[a]$p < 0.001$
[b]$p < 0.025$
[c]$p < 0.05$ Example 29

Analysis of cAMP and cGMP in Human Nasal Mucus and in Parotid Saliva

Table 29 illustrates detection and measurement of cAMP and cGMP in saliva and in nasal mucus in normal subjects. Results show that patients with smell loss had decreased levels of cAMP in their nasal mucus. These results indicate that cAMP in nasal mucus can be an index of smell loss and that its secretion may be inhibited in smell loss. Thus, monitoring of cAMP in the nasal mucus can be a diagnostic tool for the treatment of diseases related to cAMP. Results also indicate that there was less significant difference between cGMP in human nasal mucus and in parotid saliva. The results provide a non-invasive method for the detection of cAMP and cGMP in nasal mucus.

TABLE 29

Comparison of cAMP and cGMP in human nasal mucus and in parotid saliva

|  | NASAL MUCUS | PAROTID SALIVA[††] |
|---|---|---|
| TOTAL | | |
| cAMP* | $0.22 \pm 0.07$[†$] | $2.00 \pm 0.31$ |
| cGMP | $0.25 \pm 0.08$ | $0.21 \pm 0.04$ |
| MEN | | |
| cAMP | $0.21 \pm 0.13$[$] | $1.58 \pm 0.43$ |
| cGMP | $0.28 \pm 0.16$ | $0.23 \pm 0.06$ |
| WOMEN | | |
| cAMP | $0.23 \pm 0.06$[$] | $3.38 \pm 0.35$ |
| cGMP | $0.24 \pm 0.13$ | $0.20 \pm 0.07$ |
| PROTEIN** | | |
| TOTAL | $3.24 \pm 0.22$ | $3.11 \pm 0.18$ |
| MEN | $3.32 \pm 0.02$ | $3.39 \pm 0.34$ |
| WOMAN | $3.51 \pm 0.75$ | $2.93 \pm 0.02$ |

*in pmol/ml
**mg/ml
[†]MEAN ± SEM
[††]Collected in 171 subjects
[$]$p < 0.001$ compared to parotid saliva

Example 30

Analysis of cAMP and cGMP in Human Nasal Mucus in Normal Subjects and in Patients Table 30 illustrates comparison of the measurement of cAMP and cGMP in normal subjects with the patients with taste and smell loss. Results show that patients with smell loss had decreased levels of cAMP in their nasal mucus. These results indicate that cAMP in nasal mucus can be an index of smell loss and that its secretion may be inhibited in smell loss. Thus, monitoring of cAMP in the nasal mucus can be a diagnostic tool for the treatment of diseases related to cAMP. Results also indicate that there was less significant difference between cGMP in nasal mucus in normal subjects or in patients with hyposmia.

TABLE 30

Comparison of cAMP and cGMP in human nasal mucus in normal subjects and in patients with smell loss (Hyposmia)

| | | cAMP | | cGMP | | PROTEIN |
|---|---|---|---|---|---|---|
| | | pmol/ml | pmol/mg protein | pmol/ml | pmol/mg protein | mg/min |
| CONDITION NORMAL | (41) | $0.22 \pm 0.02$[†] | $0.08 \pm 0.01$ | $0.25 \pm 0.04$ | $0.06 \pm 0.01$ | $3.37 \pm 0.19$ |
| MEN | (34) | $0.21 \pm 0.01$ | $0.05 \pm 0.01$ | $0.28 \pm 0.02$ | $0.04 \pm 0.004$ | $3.32 \pm 0.13$ |
| WOMEN | (7) | $0.23 \pm 0.06$ | $0.10 \pm 0.04$ | $0.24 \pm 0.13$ | $0.10 \pm 0.04$ | $3.59 \pm 1.02$ |
| PATIENTS | (146) | $0.14 \pm 0.02$[d] | $0.07 \pm 0.01$ | $0.20 \pm 0.02$ | $0.12 \pm 0.01$ | $2.48 \pm 0.08$[b] |
| MEN | (63) | $0.14 \pm 0.02$[c] | $0.07 \pm 0.02$ | $0.25 \pm 0.03$ | $0.12 \pm 0.02$ | $2.50 \pm 0.13$[b] |
| WOMEN | (83) | $0.15 \pm 0.02$ | $0.07 \pm 0.01$ | $0.17 \pm 0.02$ | $0.11 \pm 0.01$ | $2.46 \pm 0.11$[c] |

( ) Subject number
[†]Mean ± SEM
[b]$p < 0.005$ compared to normals
[c]$p < 0.01$ compared to normals
[d]$p < 0.05$ compared to normals

Example 31

Analysis of cAMP and cGMP Concentrations in Nasal Mucus of Patients

Table 31 illustrates detection and measurement of cAMP and cGMP secretion in nasal mucus in patients with graded severity of smell loss (anosmia<Type I hyposmia<Type II hyposmia from most severe to least severe). Data indicates that as degree of smell loss increased, levels of cAMP in nasal mucus decreased. These data confirm the relationship between cAMP secretion in nasal mucus and degree of smell loss. Results also indicate that there was less significant difference between cGMP in nasal mucus in normal subjects or in patients with hyposmia.

TABLE 31 cAMP and cGMP concentrations in nasal mucus in patients with various degrees of smell loss

| PATIENTS | | TOTAL PROTEIN mg/ml | cAMP pmol/ml | cAMP PROTEIN pmol/mg | cGMP pmol/ml | cGMP PROTEIN pmol/mg |
|---|---|---|---|---|---|---|
| ANOSMIA | (2) | 1.41 | 0.004 | 0.003 | 0.179 | 0.127 |
| HYPOSMIA | | | | | | |
| TYPE I | (17) | 2.61 ± 0.29 | 0.116 ± 0.04* | 0.034 ± 0.01 | 0.225 ± 0.05 | 0.101 ± 0.02 |
| TYPE II | (64) | 2.56 ± 0.13 | 0.193 ± 0.03 | 0.102 ± 0.02$^a$ | 0.189 ± 0.03 | 0.079 ± 0.01 |
| TYPE III | | | | | | |
| NORMAL SUBJECTS | (10) | 3.70 ± 0.67 | 0.225 ± 0.67 | 0.088 ± 0.04 | 0.356 ± 0.13 | 0.094 ± 0.03 |

( ) Patient number
*Mean ± SEM
$^a$ $p < 0.001$ with respect to Type I hyposmia

Example 32

Analysis of Nitric Oxide (NO) in Saliva and in Nasal Mucus

Table 32 illustrates detection and measurement of NO in human saliva and nasal mucus. NO was found to be present in both saliva and nasal mucus and its mean concentration in saliva were 21% lower in patients than in normal subjects whereas in nasal mucus mean levels were 25% lower in patients. Treatment which increases cAMP in nasal mucus and improves smell function may be mirrored by increases in nasal mucus NO. The detection of NO in nasal mucus provides a non invasive method of diagnosing various diseases related to human physiology and pathology.

TABLE 32

NO in saliva and nasal mucus in normal subjects and in patients with smell loss

| SUBJECTS | | SALIVA | | | NASAL MUCUS | | |
|---|---|---|---|---|---|---|---|
| | | NO μg/ml | PROTEIN mg/dl | NO/PROTEIN | NO μg/ml | PROTEIN mg/dl | NO/PROTEIN |
| NORMALS | (15) | 0.57 ± 0.03$^†$ | 2.6 ± 0.1 | 0.23 ± 0.02 | 0.48 ± 0.08 | 2.3 ± 0.15 | 0.22 ± 0.05 |
| PATIENTS | (34) | 0.45 ± 0.06 | 2.8 ± 0.1 | 0.18 ± 0.03 | 0.36 ± 0.03 | 2.0 ± 0.08 | 0.21 ± 0.03 |

( ) Subject number
$^†$MEAN ± SEM

Example 33

Analysis of Nitric Oxide (NO) in Nasal Mucus in Patients Before and after Theophylline Treatment Table 33 illustrates NO levels in nasal mucus in patients treated with Theophylline in various doses before and after drug treatment. NO levels in nasal mucus changed following the treatment of patients with smell loss. Results show treatment of patients with graded increasing doses of theophylline and measurement of both smell function and NO in nasal mucus in patients with hyposmia. Results indicated that prior to the treatment levels of NO in nasal mucus were lower than in normal subjects. After treatment with theophylline in graded doses there were increases in nasal mucus NO associated with graded increases in smell function. These data demonstrate that treatment with drugs that increase smell function to or toward normal, returns smell function to normal. These results also demonstrate the measurements of various substances in nasal mucus as an index of both human physiology and pathology of various diseases. Its continual measurement during treatment of these disorders helps in monitoring efficacy of therapy. The detection of NO in nasal mucus provides a non invasive method of diagnosing various diseases related to human physiology and pathology.

TABLE 33

NO in nasal mucus in patients with Theophylline in various doses before and after drug treatment

| SUBJECTS | | PRETREATMENT | | 200 mg | | 400 mg | | 600 mg | |
|---|---|---|---|---|---|---|---|---|---|
| | | NO µg/ml | Protein mg/dl | NO µg/ml | Protein mg/dl | NO µg/ml | Protein mg/dl | NO µg/ml | Protein mg/dl |
| Patients | (12) | 0.35 ± 0.07 | 1.6 ± 0.3 | 0.25 ± 0.01 | 1.7 ± 0.3 | 0.40 ± 0.06 | 2.1 ± 0.10 | 0.59 ± 0.16 | 1.9 ± 0.15 |
| Normal | | 0.61 ± 0.20 | | | | | | | |

( ) Subject number

Example 34

Analysis of Insulin like growth factor (IGF 1) in human saliva and nasal mucus

Table 34 illustrates detection and measurement of IGF 1 in human saliva and nasal mucus in 26 subjects. Results show that IGF 1 concentration in nasal mucus was significantly greater than in saliva. Results indicate that the measurement of nasal mucus IGF 1 can be used as an index of human physiology and pathology. The detection of IGF 1 in nasal mucus provides a non invasive method of diagnosing various diseases related to human physiology and pathology.

TABLE 34

IGF 1 in human saliva and nasal mucus

| | | SALIVA | | | NASAL MUCUS | | |
|---|---|---|---|---|---|---|---|
| | | IGF 1 µg/ml | PROTEIN mg/dl | IGF 1/ PROTEIN | IGF 1 µg/ml | PROTEIN mg/dl | IGF 1/ PROTEIN |
| SUBJECTS | (26) | 11.4 ± 0.5[†] | 3.1 ± 0.2 | 4.6 ± 0.4 | 13.7 ± 0.4[b] | 2.2 ± 0.2 | 8.9 ± 1.0[a] |

( ) Subject number
[†]MEAN ± SEM
With respect to saliva
[b]$p < 0.005$
[a]$p < 0.001$

Example 35

Analysis of TNFα, TNFR$_1$, and TNFR$_2$, in Nasal Mucus of Patients

Table 35 illustrates detection and measurement of TNFα, and soluble TNF receptors 1 and 2, moieties in the nasal mucus. TNFα, and soluble TNF receptors 1 and 2 increase in systems undergoing excessive apoptosis. Treatment with 600 mg theophylline restored smell function to or toward normal in these patients. There was a significant dose-response decrease in each moiety related to a stepwise increase in theophylline treatment associated and a stepwise improvement in olfactory acuity. These results suggest that pathological apoptosis of olfactory epithelial anatomy causes smell loss in patients with hyposmia; this process is reversed with theophylline therapy which restores smell function in these patients. These results illustrate biochemical parameters associated with return of smell function in patients treated with theophylline.

TABLE 35

TNFα, TNFR$_1$, TNFR$_2$, in nasal mucus in patients with hyposmia treated with Theophylline

| | Theophylline treatment (mg/l) | | | |
|---|---|---|---|---|
| PATIENTS | PRE | 200 | 400 | 600 |
| TNFα* (24) | 18.3 ± 6.1[†] | 20.0 ± 2.8 | 12.1 ± 2.1[d] | 7.4 ± 1.8[a] |
| TNFR$_1$ (19) | 2,353 ± 718 | 3,148 ± 663 | 1,146 ± 220[b] | 1,220 ± 286[ab] |
| TNFR$_2$ (18) | 1,747 ± 535 | 1,952 ± 339 | 949 ± 180[c] | 916 ± 344 |

*in pg/ml
( ) Subject Number

TABLE 35-continued

TNFα, TNFR$_1$, TNFR$_2$, in nasal mucus in patients with hyposmia treated with Theophylline

| | Theophylline treatment (mg/l) | | | |
|---|---|---|---|---|
| PATIENTS | PRE | 200 | 400 | 600 |

[†]Mean ± SEM
[a]$p < 0.001$ with respect to 200 mg.
[b]$p < 0.001$ with respect to 200 mg.
[c]$p < 0.025$ with respect to 200 mg.
[d]$p < 0.05$ with respect to 200 mg.

Example 36

Analysis of TNFα in Nasal Mucus in Patients Before and after Treatment with Theophylline These studies were extended to reveal levels of TNFα in nasal mucus of patients with graded loss of smell following treatment with theophylline (Table 36). Smell loss was graded such that loss was greatest in Type I hyposmia, less in Type II and still less in Type III (I>II>III). Pretreatment levels of TNFα were significantly higher in patients with Type I hyposmia than in Type II hyposmia consistent with their greater degree of smell loss. Following treatment which was effective in restoring smell function toward normal, levels of TNFα decreased in each patient group consistent with each increased dose of theophylline which generated a dose dependent increase in smell function—as theophylline dose increased, smell function increased and TNFα levels decreased. In Type I hyposmia TNFα decreased 40% after treatment with 400 mg theophylline and 57% after treatment 600 mg. In Type II hyposmia TNFα decreased 11% after treatment with 600 mg theophylline.

Example 37

Analysis of TNFR 1 in Nasal Mucus in Patients Before and after Treatment with Theophylline TNF Receptor 1 (TNFR1) exhibited similar results in nasal mucus in patients with smell loss after treatment with theophylline (Table 37). With increased smell loss pre treatment TNFR 1 levels were increased in nasal mucus in patients with Type I hyposmia (whose smell loss was increased over that of patients with Type II hyposmia). After theophylline treatment, as a dose of drug increased, TNFR 1 levels decreased in Type I associated with increases in smell function. Levels of TNFR 1 at 600 mg theophylline were systematically decreased in relation to degree of smell loss. The greater was the smell loss, the higher was the level of TNFR 1.

TABLE 37

TNFR 1 in nasal mucus in patients with various types of hyposmia treated with theophylline

| HYPOSMIA TYPE | Theophylline treatment* | | | |
|---|---|---|---|---|
| | PRE | 200 | 400 | 600 |
| I (7) | $4,626 \pm 1,647^{tb}$ | $6,521 \pm 1,304^c$ | 1,498 | $1,832 \pm 704^a$ |
| II (10) | $837 \pm 60$ | $1,462 \pm 371$ | $1,087 \pm 335$ | $862 \pm 335$ |
| III (2) | — | — | — | $585 \pm 335$ |

*in mg orally daily
( ) Subject Number
$^t$Mean ± SEM
a $p < 0.005$ with respect to 200 mg
b $p < 0.02$ with respect to Type II pre treatment
c $p < 0.01$ with respect to Type II or 200 mg

TABLE 36

TNFα in nasal mucus in patients with various types of hyposmia treated with theophylline

| HYPOSMIA TYPE | Theophylline treatment* | | | |
|---|---|---|---|---|
| | PRE | 200 | 400 | 600 |
| I (8) | $26.0 \pm 6.5^{tb}$ | — | 15.6 | $11.2 \pm 4.4$ |
| II (13) | $5.3 \pm 1.0$ | $14.9 \pm 2.5$ | $11.5 \pm 3.2$ | $4.3 \pm 0.8^a$ |
| III (3) | — | — | — | $1.2 \pm 0.7^{bc}$ |

*in mg orally daily
( ) Subject Number
$^t$Mean ± SEM
$^a$ $p < 0.001$ with respect to 200 mg
$^b$ $p < 0.001$ with respect to Type I (600 mg)
$^c$ $p < 0.01$ with respect to Type II (600 mg)
d $p < 0.001$ with respect to Type II, pre treatment

Example 38

Analysis of TNFR 2 in Nasal Mucus in Patients Before and after Treatment with Theophylline TNR Receptor 2 (TNFR 2) in nasal mucus exhibited similar results (Table 38). Pretreatment with theophylline in patients with the most severe smell loss (Type I hyposmia) exhibited higher TNFR 2 levels in nasal mucus than did patients with less severe smell loss (Type I hyposmia). With a dose dependent increase of theophylline treatment levels of TNFR 2 in nasal mucus decreased consistent with a dose dependent increase in smell function. Levels of TNFR 2 in patients with Type I and Type II hyposmia decreased almost 50% on 600 mg theophylline consistent with their greatest return of smell function. At this highest level of theophylline levels of TNFR 2 were decreased in relationship to the decrease in smell function—TNFR 2, Type I>Type II>Type III; smell loss, Type I>Type II>Type III.

TABLE 38

TNFR 2 in nasal mucus in patients with various types of hyposmia treated with theophylline

| HYPOSMIA TYPE | Theophylline treatment* | | | |
|---|---|---|---|---|
| | PRE | 200 | 400 | 600 |
| I (7) | 2,718 ± 1,125[f] | 3,100 ± 1,184 | — | 1,491 ± 1,102 |
| II (10) | 1,145 ± 625 | 1,378 ± 480 | 1,014 ± 272 | 553 ± 158 |
| III (2) | — | — | — | 436 ± 443 |

*in mg orally daily
( ) Subject Number
[f]Mean ± SEM
a $p < 0.001$ with respect to 200 mg
b $p < 0.001$ with respect to Type I (600 mg)
c $p < 0.01$ with respect to Type II (600 mg)

Example 39

Analysis of Endoglin in Human Plasma, Urine, Saliva and Nasal Mucus

Table 39 illustrates detection and measurement of Endoglin in the nasal mucus. Results indicate that the measurement of nasal mucus Endoglin can be used as an index of human physiology and pathology. The detection of Endoglin in nasal mucus provides a non invasive method of diagnosing various diseases related to human physiology and pathology.

105:438-450; Henkin, Robert, et al., *FASEB J.*, 2002, 16:A878; Henkin, R. I., *Encyclopedia of Neuroscience* (3rd Ed), Adelman, G. Smith, B H eds, Birkhauser, Boston, 2003, and; Moharram, R., et al., *FASEB J.*, 2004, 18:A201, all incorporated by reference in their entirety herein.

Stimulation was applied in a fixed manner to four skull locations (left and right temporoparietal, occipital, frontal of patients). Stimulus frequency was 1 pulse given per 1-3 sec for 30-90 sec with 20 pulses given at each location. Repeat stimulation was performed in all patients in whom increased sensory acuity and/or decreased sensory distortions occurred;

TABLE 39

Endoglin in human plasma, urine, saliva and nasal mucus

| | PLASMA | | | URINE | SALIVA | NASAL MUCUS | | |
|---|---|---|---|---|---|---|---|---|
| SUBJECTS | ENDOGLIN mg/ml | PROTEIN mg/dl | ENDOGLIN PROTEIN | ENDOGLIN mg/ml | ENDOGLIN mg/ml | ENDOGLIN mg/ml | PROTEIN mg/dl | ENDOGLIN PROTEIN |
| (33) | 2.7 ± 0.1[†a] | 7.1 ± 0.1 | 0.38 ± 0.1 | 0 | 0 | 0.2 ± 0.1 | 2.8 ± 0.1 | 0.07 ± 0.01 |

( ) Subject number
[†]MEAN ± SEM
[a]$p < 0.001$ with respect to nasal mucus

Example 40

Increased Carbonic Anhydrase (CA) I, II and VI, Zinc and Copper after rTCMS

Ninety three patients, aged 18-85y (52±2y, Mean±SEM), 49 men, aged 29-74y (51±3y) and 44 women, aged 20-85y (53±3y) with hyposmia, hypogeusia, and subsequent phantageusia (distortion of taste independent of any oral stimulus) and/or phantosmia (distortion of smell independent of any environmental odor) were studied before and after rTCMS in a single blind placebo controlled fixed sequence clinical trial. Patient symptoms persisted for 0.4-30y (6.9±1.5y) prior to rTCMS. Physical examination of head and neck including examination of oral and nasal cavities (the nose examined by anterior rhinoscopy with use of vasoconstrictor agents) was within normal limits. Neither neurological nor psychiatric abnormalities other than taste and/or smell dysfunction was present in any patient. Anatomical magnetic resonance imaging (MRI) of brain and electroencephalographic (EEG) studies in all patients were within normal limits.

rTCMS was performed with a Cadwell magnetic pulse stimulator (Kennewick, Wash.) monitored with a TECA TD20 (Pleasantville, N.Y.) wave form generator, as described in Cicinelli, P., et al., *Eletroenceph. Clin. Neurophys*, 1997, repetition continued (two-six applications) until no further increase in sensory acuity and/or decrease in sensory distortions occurred.

One hour before and one to two hr after completion of rTCMS, venous blood and parotid saliva were collected. Whole venous blood was placed into zinc free tubes containing 100 μl of zinc free heparin, on ice, centrifuged at 3000 rpm at 4° C., plasma removed and stored at −20° C. until assayed. Erythrocytes were washed and treated as described in Agarwal, R. P., et al., *Bio. Tr. Elem. Res.*, 1985, 7:199-208, incorporated by reference in its entirety herein. Parotid saliva was collected in four plastic tubes on ice using a modified Lashley cup applied to Stensen's duct with maximal stimulation using reconstituted lemon juice applied to the lingual surface as described in, Henkin, R. I., et al., *Proc. Nat. Acad. Sci. USA*, 1975, 72:488-492 and Henkin, R. I., et al., *Amer. J. Med. Sci.*, 1976, 272:285-299, both incorporated by reference in their entirety herein. The first three tubes were collected at two min intervals, the fourth tube until approximately eight ml was collected. For convenience only results of saliva from the fourth tube will be presented. Five hundred μl of saliva from the fourth tube was placed in dry ice immediately after collection and stored at −60° C. until measurements by SELDI-TOF mass analysis was performed.

Zinc and copper were measured in each tissue by atomic absorption spectrophotometry (AAS) by using a double beam ThermoJarrell Ash video 22 (Franklin, Mass.) AAS modified by the Maxwell Instrument Company (Salisbury, N.C.), the methods previously described in, Henkin, R. I., et al., *Amer. J. Med. Sci*, 1999, 318, 380-391; Agarwal, R. P., et al., *Bio. Tr. Elem. Res.*, 1985, 7:199-208; Henkin, R. I., et al., *Amer. J. Med. Sci.*, 1976, 272:285-299, and; Meret, S., et al., *Clin. Chem.*, 1971, 17:369-373, all incorporated by reference in their entirety herein. Saliva protein was determined by measurement of total peptide content by use of absorbance at A215-A225 (called 4215) and the extinction coefficient. CA activity was measured by a modification of the method of Richli, E. E., et al., *J. Biol. Chem.*, 1964, 239:1065-1078, incorporated herein by reference in its entirety. Saliva samples stored at −60° C. were thawed and 1 µl directly spotted on an H4 Protein Chip array (pre washed with 0.1% TFA in 50% aqueous acetonitrile) and their protein profile examined on a Ciphergen (Fremont, Calif.) PBS IIc mass analyzer.

Samples were first incubated in a humid chamber for 5-10 minutes at room temperature, then washed with 5% aqueous acetonitrile, dried and 1 µl matrix added (sinapinic acid in 0.1% TFA, 50% aqueous acetonitrile). Samples were allowed to dry again and subjected to SELDI-TOF analysis on the PBS IIc. Protein peaks were characterized by their apparent molecular weight based on their mass/charge ratio (m/z).

Following initial observation of biochemical changes after rTCMS subsequent measurements in all biological fluids were performed in a blinded manner; all samples were coded and results uncoded only after all analyses were completed. Mean±SEM for each parameter was determined for each condition pre and post rTCMS. Differences between each condition were calculated for each parameter and significance of differences determined by parametric (differences between undifferentiated means, paired t tests, $X^2$) and non parametric (sign test) statistics.

Results:

After rTCMS mean CA VI activity and salivary zinc and copper concentrations increased significantly as did mean CA I, II activity and plasma copper concentrations (Table 40). Significant increases in both CA I, II and CA VI activity were also measured using paired comparisons (p<0.01 Student t test) and the sign test (p<0.05, Student t test) (data not shown). These latter data are reflected in results shown in Table 41 in which changes pre and post rTCMS are shown. Increased CA VI was measured in 87% of patients with changes varying from −5% to +153% (mean change, +17%) (Table 41); compared to chance changes of this magnitude would occur <5 times in 1000 ($X^2$). Increased CA I, II was measured in 93% of patients with changes varying from −2% to +56% (mean change, +11%) (Table 41); compared to chance changes of this magnitude would also occur <1 time in 1000 ($X^2$). Increased plasma and erythrocyte zinc and copper concentrations were measured in 91-93% of patients (Table 41); compared to chance changes of this magnitude would also occur <1 time in 1000 ($X^2$).

TABLE 40

Changes in plasma, erythrocyte and saliva CA I, II and VI, zinc and copper before (pre) and after (post) rTCMS in 93 patients rTCMS

| CONDITION | PRE | POST |
|---|---|---|
| PLASMA | | |
| Zn (µg/dl) | 85 ± 2* | 88 ± 2 |
| Cu (µg/dl) | 101 ± 2 | 109 ± 3[a] |
| ERYTHROCYTES | | |
| Zn (µg/gHb) | 38.0 ± 0.5 | 39.7 ± 0.5[b] |
| Cu (µg/gHb) | 2.1 ± 0.04 | 2.2 ± 0.05 |
| CA I, II (µg/g protein) | 3.12 ± 0.06 | 3.45 ± 0.06[d] |
| SALIVA | | |
| Zn (µg/L) | 103 ± 5 | 121 ± 5[b] |
| Cu (µg/L) | 13 ± 1 | 22 ± 3[c] |
| CA VI (µg/g protein) | 0.153 ± 0.009 | 0.197 ± 0.008[d] |

*Mean ± SEM
CA, carbonic anhydrase
Compared to pre rTCMS
[a]p < 0.05
[b]p < 0.025
[c]p < 0.01
[d]p < 0.001

TABLE 41

Changes in plasma, erythrocyte and saliva carbonic anhydrase I, II and VI, zinc and copper before (pre) and after repetitive transcranial magnetic stimulations (rtcms) in patients with decreased sensory acuity and presence of sensory distortions
rTCMS
PRE vs. POST

| | NUMBER | | | |
|---|---|---|---|---|
| CONDITION | INCREASED | DECREASED | UNCHANGED | INCREASED |
| PLASMA | | | | |
| | | | | % |
| Zn (µg/dl) | 61 | 6 | 0 | 91 |
| Cu (µg/dl) | 62 | 5 | 0 | 93 |
| ERYTHROCYTES | | | | |
| Zn (µg/gHb) | 66 | 1 | 0 | 99 |
| Cu (µg/gHb) | 62 | 4 | 1 | 93 |
| CA I, II (µg/g protein) | 62 | 4 | 1 | 93 |
| SALIVA | | | | |
| Zn (µg/L) | 49 | 18 | 0 | 73 |
| Cu ((µg/L) | 51 | 16 | 0 | 76 |

TABLE 41-continued

Changes in plasma, erythrocyte and saliva carbonic anhydrase I, II and VI, zinc and copper before (pre) and after repetitive transcranial magnetic stimulations (rtcms) in patients with decreased sensory acuity and presence of sensory distortions
rTCMS
PRE vs. POST

| | NUMBER | | | |
|---|---|---|---|---|
| CONDITION | INCREASED | DECREASED | UNCHANGED | INCREASED |
| CA VI (µg/g protein) | 60 | 5 | 2 | 90 |

Figure 10:
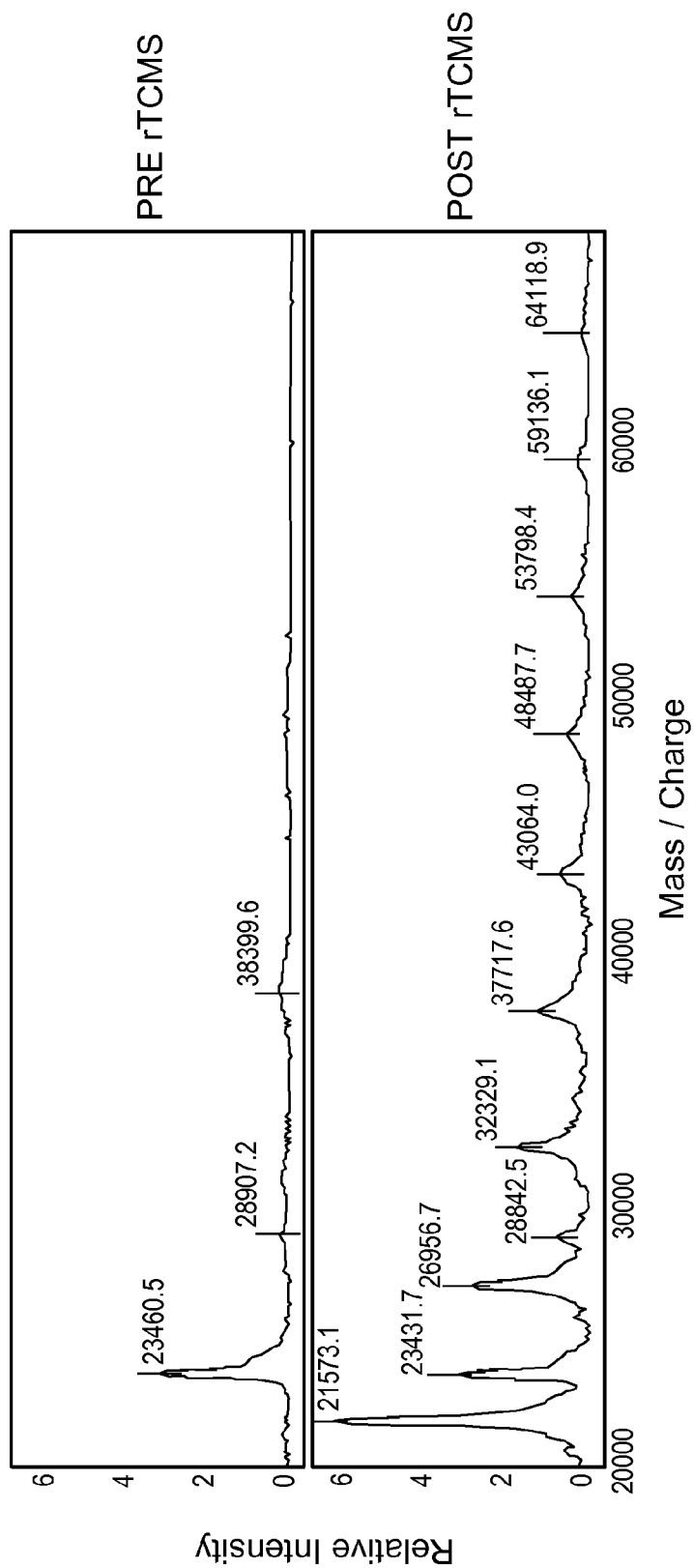
FIG. 10 depicts mass spectroscopic analysis of parotid saliva of patients before and after treatment with rTCMS.

SELDI-TOF mass spectrometry revealed a peak at m/z 21.5K in the post rTCMS spectra which was absent in the pre rTCMS spectra (FIG. 10). Also present in the post rTCMS spectra was a repetitive protein pattern separated by intervals of approximately 5K m/z (FIG. 10). Similar patterns were observed in about ⅓ of patients studied.

Thus, the present study illustrates that several salivary proteins can be induced after rTCMS (FIG. 10). Increased enzyme activities and zinc and copper concentrations usually persisted two-four wk after rTCMS; however, over time there was a slow, gradual decrease in enzyme activities and in plasma, erythrocyte and saliva zinc and copper concentrations as well as a loss of sensory acuity and subsequent return of sensory distortions.

This study demonstrates that biochemical changes may occur after rTCMS. Since changes in taste and smell function occur in several neurological disorders these results may also relate to other conditions such as epilepsy, Parkinsonism, Alzheimer disease, head injury, and motor neuron disease in which rTCMS can be an effective therapeutic agent.

Example 41

Recovery of Taste and Smell Function Following rTCMS

Seventeen right handed Caucasian patients, five men, aged 40-74y (58±7y, X±SEM), 12 women, aged 30-76y (51±5y) were studied. Each had mild to severe persistent hyposmia and hypogeusia as well as mild to severe persistent birhinal phantosmia and/or global oral phantageusia; the sensory distortions were profound enough to interfere with normal life pursuits. Acuity loss persisted for 6 mo to 30y (4.1±2y) and sensory distortions persisted for 3 mo to 30y (3.7±2y) prior to clinic visit. Etiologies which initiated their symptoms were head injury (4 patients), post influenza-like infection (PIHH, 7 patients), idiopathic causes (4 patients) and drug reactions (2 patients). Each of the 17 patients who presented with these symptoms was treated with rTCMS.

None had any neurological symptom other than loss of sensory acuity and presence of sensory distortions. None had any psychiatric symptom other than some depression associated with persistence of these cognitive impairments. Symptoms were unrelieved by any prior treatment with multiple agents including antiepileptics, anxiolytics, antidepressants, trace metals, vitamins and a variety of alternative treatment modalities including herbal remedies, acupuncture, chiropractic techniques and hypnosis. Physical examination of each patient, including examination of the head and neck and general neurological examination, was within normal limits. Both anatomical brain MRI and electroencephalograms were within normal limits in each patient.

Measurement Techniques:

A battery of tests measuring taste and smell acuity and character and degree of sensory distortions were administered to each patient. Taste and smell acuity were determined by standard three stimuli forced choice staircase techniques (Henkin R. I., Amer. J. Med. Sci. 1976, 272:285-299, incorporated herein by reference in its entirety) by which detection (DT) and recognition (RT) thresholds and magnitude estimation (ME) for four tastants [NaCl (salt), sucrose (sweet), HC 1 (sour) and urea (bitter)] and four odorants [pyridine (dead fish), nitrobenzene (bitter almond), thiophene (old motor oil) and amyl acetate (banana oil)] were determined, and reference values established for a large number of normal subjects. Results for DT and RT, in mmol/L and M/L for tastants and odorants, respectively, were converted into bottle units (BU) and compared to previously established standards. Magnitude estimation (ME) was determined, calculated in % for each stimulus and compared to previously described standards in Henkin et al. *Otolaryngology*, 1993, vol. 2, p 1-86 and Henkin et al. *Drug safety*, 11:310-377, 1994, incorporated herein by reference in its entirety.

Sensory distortions were graded daily in intensity, duration and frequency using a written record on a 0-100 scale for 3 d-4-wk prior to rTCMS; 0 reflected total absence of sensory distortions, 100 reflected the digitized composite of the most intense distortion experienced over the entire day. Records were reviewed prior to the study to insure adequate understanding of symptom grading. The entire battery of cognitive measurements was obtained at the initial patient visit and repeated immediately prior to and after each rTCMS treatment. This battery was also repeated at variable intervals (1 day, 2-4-wk, 6-46 mo) after each rTCMS treatment. Each test battery was performed independent of knowledge of any prior test result.

Treatment Protocol:

rTCMS was performed with a Cadwell magnetic pulse stimulator (Kennewick, Wash.) monitored by a TECA TD20 (Pleasantville, N.Y.) wave form generator. Stimulation was applied by a single open quadrangular 12×12 cm coil. Three sequential stimulation protocols were used. The first two were considered placebo or sham trials.

For the initial sham trial, 20 stimuli at intervals of 1-3 sec were applied sequentially at the lateral acromial process of the clavicle (near Erb's point) (a) to the anterior right shoulder, then (b) anterior left shoulder at 20-30% maximal output [20-30% of 1.5 T or ~0.2-0.4 T (since stimulus delivery was non-linear)] and then (c) to the back of the mid neck region (at the level of C5-8 at 30-40% maximal output or ~0.4-0.8 T); mild muscle group flexion of arm and hand muscles (shoulder stimulation) and neck, strap and facial muscles (neck) followed each stimulation and was visually monitored.

For the second sham trial, 20 stimuli at intervals of 1-3 sec were applied sequentially to four skull regions (left temporoparietal, occipital, right temporoparietal, frontal) at 20% maximal output; this was considered subthreshold stimulation since no peripheral muscle responses occurred.

For the treatment trial, 20 stimuli at intervals of 1-3 sec were applied at 40-55% maximal output (~0.8-LIT) to each skull location as in the second sham trial noted above. Muscle responses to this latter stimulation were present and monitored by visual observation (e.g., right/left thenar and/or phalangeal flexion with left/right temporoparietal stimulation, respectively).

After each 20 stimuli of sham or treatment stimulation at each anatomical location, olfactory response to presentation of a single odor (one concentration of an odorant whose DT, RT and ME were previously determined) and/or changes in intensity and character of phantageusia and/or phantosmia (previously determined) was recorded. If any change in olfactory acuity or in sensory distortion occurred after any stimulation, stimulation at that location at that same intensity was repeated two-six times until no further change occurred.

Outcome Measures:

Mean±SEM of changes in taste and smell acuity (DT, RT, ME) and in intensity of sensory distortions before and after each rTCMS treatment were calculated and significance of differences determined by Student's t tests. Differences were also calculated using paired t tests with significance of differences pre and post rTCMS determined by Student's t test.

Results: Pre rTCMS I

Taste:

Mean DTs and RTs for all tastants were above normal (i.e. acuity was decreased). Mean MEs for all tastants were below normal (i.e. acuity was decreased) (Table 42). Mean DT and RT for all tastants except DT for HC 1 were significantly above normal and mean MEs for all tastants were significantly below normal.

Smell:

Mean DTs and RTs for all odorants were above normal (i.e. acuity was decreased) and mean MEs for all odorants were below normal (i.e. acuity was decreased) (Table 42). Mean DT and RT for all odorants (except DTs for pyridine, thiophene and amyl acetate) and mean MEs of all odorants were significantly above normal (Table 42).

Sensory Distortions:

Phantageusia intensity was 82±7%. Phantosmia intensity was 72±14% (Table 43). There were no gender differences in either phantageusia or phantosmia intensity (Table 43).

Results: Post rTCMS I

Placebo or Sham Stimulation (0.2-0.4 T):

No subjective or objective changes in either taste and/or smell acuity or in character or intensity of sensory distortions occurred in any patient following stimulation of shoulders or neck or in any skull location.

Treatment Stimulation (0.8-1.1 T):

Taste:

Mean DTs and RTs for all tastants decreased (i.e., acuity increased) and mean MEs for all tastants increased (i.e. acuity increased) (Table 42). Mean DT and RT returned to normal levels for NaCl, sucrose and HCl as did DT for urea and ME for all tastants (Table 42). Only mean RT for urea did not return to normal although it was significantly lower than before treatment (Table 42).

Smell:

Mean DTs and RTs for all odorants decreased (i.e., acuity increased) and mean MEs for all odorants increased (i.e., acuity increased) (Table 42). Mean DT and RT for pyridine, nitrobenzene and thiophene and mean DT for amyl acetate returned to or below normal levels after treatment (Table 42). Only mean RT for amyl acetate did not return to normal although it was significantly below values obtained before this treatment. Mean ME for all odorants also returned to normal levels.

Sensory Distortions:

Mean phantageusia and phantosmia intensity decreased significantly (Table 43). In each man phantosmia disappeared.

Response Summary:

No changes in taste or smell acuity or in sensory distortion intensity occurred in two patients immediately after treatment stimulation [(one with head injury, one with PIHH, both women, data included in Tables 42 and 43)]. These two patients were labeled non-responders. Reports of no change in sensory distortion intensity and no change in repeat acuity testing occurred in these two patients 2-7 d after treatment. No changes were reported 4 wk after rTCMS I and no further data about these patients were obtained.

Taste and smell acuity returned to normal levels for all tastants and odorants and all sensory distortions completely disappeared in two patients within one hr after rTCMS I [(one with head injury (one woman) one with PIHH (one man), data included in Tables 42 and 43)]. These two patients were labeled responders. Repeat testing 2-7 d after rTCMS I demonstrated normal sensory acuity and no sensory distortions were reported (data not shown). Reports of normal sensory acuity and absence of any sensory distortions were received for as long as these patients were followed (46 mo).

In the remaining 13 patients sensory acuity improved (Table 42) and sensory distortions diminished (Table 43) one hour after stimulation (Table 43). These 13 patients were also labeled responders. Symptom improvement occurred (vs) in all responders when the field was applied at only one skull location. Seven patients reported improvement after left temporoparietal stimulation, four (27%) after right temporoparietal stimulation, three (20%) after frontal stimulation and one (7%) after occipital stimulation. There was no improvement in the non-responders no matter where the field was applied.

Later Post rTCMS I

Four wk-2 mo after rTCMS I, repeat testing of taste and smell acuity and measurement of sensory distortion intensity indicated that cognitive impairments had returned in 13 of the 15 responders (vs). A second trial of rTCMS (rTCMS II) was instituted in these patients.

Pre rTCMS II

Immediately prior to rTCMS II, the entire battery of sensory tests and measurement of sensory distortion intensity previously measured were repeated (Table 44).

Taste:

Compared to immediately post rTCMS I, mean DTs and RTs for all tastants (except DT for HCl which did not change) increased (i.e., acuity decreased) and mean MEs for all tastants decreased (i.e., acuity decreased) (cf Tables 44, 42).

Smell:

Compared to immediately post rTCMS I, mean DTs and RTs for all odorants (except RT for thiophene which was lower than post rTCMS I) increased (i.e., acuity decreased) and mean MEs for all odorants decreased (i.e., acuity decreased), (except for thiophene which was higher (cf Tables 44, 42). However, mean MEs were all higher than pre rTCMS I indicating that some improvement after rTCMS I was retained.

Sensory Distortions:

Compared to immediately after rTCMS I, mean estimates of phantageusia intensity increased but were significantly less than intensities measured prior to rTCMS I (cf Tables 45, 43, pre rTCMS I, 82±7, later post rTCMS I, 39±20, p<0.05 t test, p<0.02 paired t test). Similarly mean estimates of phantageusia intensity also increased but were less than pre rTCMS I (cf Tables 45, 43, pre rTCMS I, 72±14, later post rTCMS I, 47±8, p>0.05 t test, p<0.05 paired t test). Similar changes also occurred in phantosmia (cf Tables 45, 43).

Response Summary:

These results suggest that the improvement in cognitive impairments which occurred immediately after rTCMS I persisted to some extent but these patients "escaped" from this improvement with a return of cognitive impairments. A second course of rTCMS was instituted.

rTCMS II

Placebo or Sham Stimulation (0.2-0.4 T):

No subjective or objective changes in either taste and/or smell acuity or in character or intensity of sensory distortions occurred in any patient following stimulation of shoulders, neck or in any skull location.

Treatment Stimulation (0.8-1.1 T):

Taste:

Mean DTs and RTs for all tastants decreased (i.e., acuity increased) and mean MEs for all tastants increased (i.e., acuity increased) (Table 44) as after rTCMS I (Table 42). There were significant decreases in DTs for NaCl and urea and RTs for HCl and urea. Mean MEs for all tastants were not significantly different from normal (Table 44). DT for NaCl was significantly lower, (i.e., relative increased acuity) than normal as was DT for urea.

Smell:

Mean DTs and RTs for all odorants decreased (i.e., acuity increased) and mean MEs for all odorants increased (i.e., acuity increased) (Table 44) as after rTCMS I (Table 42). There were no significant differences in mean DTs, RTs or MEs for any odorant with respect to normal. DTs for nitrobenzene and thiophene and RTs for pyridine and nitrobenzene were lower than normal (i.e., relative increased acuity) and MEs for pyridine, nitrobenzene and thiophene were higher than normal (i.e., relative increased acuity).

Sensory Distortions:

Significant decreases occurred in phantageusia and phantosmia (Table 45) as after rTCMS I (Table 43). Phantosmia completely disappeared after treatment in all patients including all men and women, not just in men as after rTCMS I (Table 43). Phantageusia disappeared in 10 patients, improved by 50% in one and only slightly, if at all, in two. After rTCMS II both mean phantageusia and phantosmia intensity decreased to levels below those measured later post rTCMS I (cf, Tables 43, 45).

In these 13 patients rTCMS II was effective in initiating improvement again only at the same locus at which initial improvement occurred after rTCMS I.

Response Summary:

After rTCMS II improvement lasted longer than after rTCMS I, lasting wk-mo. In seven of these 13 (54%) (one with head injury, four with PIHH, two idiopathic) return of sensory acuity to normal and total cessation of sensory distortions persisted for as long as measurements were made (30 mo). In the remaining six patients (one with head injury, one with PIHH, the two with idiopathic causes, the two with drug reactions) symptoms of cognitive impairment returned after one-five mo but acuity was less impaired and sensory distortions were less intense than prior to rTCMS II (as in pre rTCMS I and II).

These six patients who "escaped" from rTCMS II were again treated with rTCMS (rTCMS III) as in rTCMS I and II. This therapy was again effective in improving cognitive impairments but again only at the same locus that initiated improvement after prior stimulation (data not shown). All sensory acuity returned to normal levels and all sensory distortions disappeared in these six patients for as long as they were followed (6-36 mos).

The results indicate that rTCMS was efficacious in improving taste and/or smell acuity and in inhibiting phantosmia and phantageusia in most patients who exhibited these symptoms. Improvement occurred after rTCMS at one brain region. However, 13 of the 15 who initially responded exhibited a recurrence of their symptomatology. With recurrent symptomatology repeat rTCMS was effective again in improving symptoms but only after application at the same site at which initial improvement occurred, mainly the left temporoparietal region, a locus contralateral to patient handedness. This result indicates enhanced cognitive processing following rTCMS in one brain locus, mainly left prefrontal cortex. Repeated stimulation in patients at this effective locus prolonged improvement in cognitive function. TCMS can be applied in many different paradigms including use of single or repeated pulses, short or prolonged applications, varied wave forms, application intensity and a multiplicity of other parameters. The results of this experiment indicate that rTCMS improved sensory acuity and decreased sensory distortions in patients with these cognitive impairments.

TABLE 42

Changes in taste and smell acuity in 17 patients with hypogeusia, hyposmia, phantosmia and/or phantageusia pre and post rTCMS I compared to normal responses

| TASTANT | | | | | | | | | | | |
|---|---|---|---|---|---|---|---|---|---|---|---|
| NaCl | | | SUCROSE | | | HCl | | | UREA | | |
| DT | RT | ME | DT | RT | ME | DT | RT | ME | DT | RT | ME |
| PRE | | | | | | | | | | | |
| $5.7 \pm 0.7^{\dagger a}$ | $6.3 \pm 0.9^b$ | $26 \pm 18^{d\ddagger}$ | $4.9 \pm 0.6^c$ | $5.2 \pm 0.6^a$ | $29 \pm 12^e$ | $5.3 \pm 0.9$ | $6.8 \pm 0.8^a$ | $27 \pm 6^a$ | $6.8 \pm 1.4^e$ | $9.0 \pm 1.0^a$ | $30 \pm 9^b$ |
| POST | | | | | | | | | | | |
| $3.2 \pm 0.0^g$ | $3.6 \pm 0.3^{b*}$ | $35 \pm 22$ | $3.6 \pm 0.4$ | $3.9 \pm 0.3$ | $46 \pm 12$ | $4.1 \pm 0.7$ | $4.3 \pm 0.6^j$ | $57 \pm 7^k$ | $5.0 \pm 1.0$ | $5.7 \pm 0.6^h$ | $53 \pm 8$ |

TABLE 42-continued

Changes in taste and smell acuity in 17 patients with hypogeusia, hyposmia, phantosmia and/or phantageusia pre and post rTCMS I compared to normal responses

| NORMALS | | | | | | | | | | | |
|---|---|---|---|---|---|---|---|---|---|---|---|
| 3.3 ± 0.3 | 3.4 ± 0.2 | 68 ± 4 | 3.3 ± 0.2 | 3.4 ± 0.2 | 60 ± 4 | 3.4 ± 0.4 | 3.5 ± 0.4 | 66 ± 4 | 3.6 ± 0.4 | 3.7 ± 0.4 | 68 ± 4 |

| ODORANT | | | | | | | | | | | |
|---|---|---|---|---|---|---|---|---|---|---|---|
| PYRIDINE | | | NITROBENZENE | | | THIOPHENE | | | AMYL ACETATE | | |
| DT | RT | ME | DT | RT | ME | DT | RT | ME | DT | RT | ME |
| PRE | | | | | | | | | | | |
| 4.0 ± 0.9† | 8.5 ± 0.7$c$ | 35 ± 13$e‡$ | 6.4 ± 0.7$b$ | 9.4 ± 0.4$a$ | 21 ± 7$b$ | 3.8 ± 0.8 | 7.4 ± 1.0$a$ | 30 ± 7$b$ | 4.3 ± 1.1 | 8.9 ± 1.8$a$ | 24 ± 7$a$ |
| POST | | | | | | | | | | | |
| 1.9 ± 0.5$ah$ | 4.4 ± 0.9$f$ | 67 ± 11 | 3.2 ± 0.8$g$ | 6.2 ± 1.0$g$ | 42 ± 8 | 1.9 ± 0.3$i$ | 5.1 ± 0.9 | 45 ± 7$h$ | 1.4 ± 0.0$ch$ | 5.2 ± 0.9$g$ | 44 ± 6$f$ |
| NORMALS | | | | | | | | | | | |
| 3.7 ± 0.3 | 6.0 ± 0.7 | 66 ± 5 | 3.6 ± 0.4 | 6.0 ± 0.6 | 52 ± 6 | 3.2 ± 0.6 | 3.3 ± 0.5 | 69 ± 6 | 3.1 ± 0.5 | 3.3 ± 0.6 | 53 ± 5 |

DT, detection threshold (in BU),
RT, recognition threshold (in BU),
ME, magnitude estimation (in %)
†MEAN ± SEM (in BU)
‡MEAN ± SEM (in %)
*All significance determined by Student's t test
Normals are 150 normal volunteer Compared to normals
$^a$p < 0.001
$^b$p < 0.005
$^{b*}$ p < 0.01
$^c$p < 0.02
$^d$p < 0.025
$^e$p < 0.05
Compared to pre rTCMS I
$^f$p < 0.001
$^g$p < 0.005
$^h$p < 0.01
$^i$p < 0.025
$^j$p < 0.02
$^k$p < 0.05

TABLE 43

Changes in phantageusia and phantosmia in 17 patients with hyposmia, hypogeusia, phantosmia and/or phantageusia pre and post rTCMS I

| PATIENTS | PHANTAGEUSIA | | PHANTOSMIA | |
|---|---|---|---|---|
| | PRE | POST | PRE | POST |
| TOTAL(17) | 82 ± 7† | 21 ± 7$a$ | 72 ± 14 | 22 ± 12$c$ |
| MEN(5) | 71 ± 15 | 20 ± 15$d$ | 70 ± 20 | 0$b$ |
| WOMEN(12) | 85 ± 6 | 22 ± 9$a$ | 74 ± 18 | 33 ± 17 |

( ) Patient Number
†MEAN ± SEM [in %, of most intense distortions experienced throughout waking state]
$ Significance determined by Student's t test

*All results compared to pre rTCMS I
$^a$p < 0.001 *
$^c$p < 0.02 *
$^d$p < 0.025 *
e p < 0.05 *
$^b$p < 0.01

TABLE 44

Changes in taste and smell acuity in 13 patients with hyposmia, hypogeusia, phantosmia, and/or phantageusia pre and post second rTCMS treatment

| TASTANT | | | | | | | | | | | |
|---|---|---|---|---|---|---|---|---|---|---|---|
| NaCl(4) | | | SUCROSE(5) | | | HCl(8) | | | UREA (12) | | |
| DT | RT | ME | DT | RT | ME | DT | RT | ME | DT | RT | ME |
| PRE | | | | | | | | | | | |
| 5.3 ± 1.5†* | 9.5 ± 2.1$a$ | 50 ± 10‡ | 4.8 ± 0.7$d$ | 7.3 ± 1.6$c$* | 46 ± 8 | 4.9 ± 0.5$c$* | 8.8 ± 0.8$a$ | 46 ± 8$c$ | 6.4 ± 0.3$a$ | 7.9 ± 0.3$a$ | 42 ± 10$c$* |

TABLE 44-continued

Changes in taste and smell acuity in 13 patients with hyposmia, hypogeusia, phantosmia, and/or phantageusia pre and post second rTCMS treatment

POST

| | | | | | | | | | | | |
|---|---|---|---|---|---|---|---|---|---|---|---|
| $1.0 \pm 0^{ae}$ | $6.2 \pm 2.8$ | $68 \pm 9$ | $3.2 \pm 0.7$ | $4.7 \pm 1.0$ | $62 \pm 8$ | $4.1 \pm 0.7$ | $5.9 \pm 0.9^{ch}$ | $72 \pm 6^g$ | $3.4 \pm 0.5^e$ | $4.2 \pm 0.9^{hm}$ | $63 \pm 11$ |

NORMALS

| | | | | | | | | | | | |
|---|---|---|---|---|---|---|---|---|---|---|---|
| $3.3 \pm 0.3$ | $3.4 \pm 0.2$ | $68 \pm 4$ | $3.3 \pm 0.2$ | $3.4 \pm 0.2$ | $60 \pm 4$ | $3.4 \pm 0.4$ | $3.5 \pm 0.4$ | $66 \pm 4$ | $3.6 \pm 0.4$ | $3.7 \pm 0.4$ | $68 \pm 4$ |

ODORANT

| PYRIDINE(9) | | | NITROBENZENE(10) | | | THIOPHENE(10) | | | AMYL ACETATE(12) | | |
|---|---|---|---|---|---|---|---|---|---|---|---|
| DT | RT | ME | DT | RT | ME | DT | RT | ME | DT | RT | ME |

PRE

| | | | | | | | | | | | |
|---|---|---|---|---|---|---|---|---|---|---|---|
| $6.2 \pm 1.2^{i\dagger}$ | $10.0 \pm 1.1^b$ | $48 \pm 10^\ddagger$ | $8.0 \pm 1.9^c$ | $10.3 \pm 0.6^e$ | $39 \pm 8$ | $9.0 \pm 1.8^a$ | $10.0 \pm 0.4^a$ | $57 \pm 9$ | $8.7 \pm 0.4^a$ | $10.7 \pm 0.4^a$ | $36 \pm 10$ |

POST

| | | | | | | | | | | | |
|---|---|---|---|---|---|---|---|---|---|---|---|
| $4.8 \pm 1.1$ | $5.5 \pm 1.6^i$ | $76 \pm 5^g$ | $4.2 \pm 1.6$ | $4.0 \pm 1.4^b$ | $62 \pm 8$ | $3.0 \pm 0.9^e$ | $5.0 \pm 1.4^{bm}$ | $70 \pm 6$ | $4.0 \pm 2.0^f$ | $4.6 \pm 1.5^e$ | $51 \pm 10$ |

NORMALS

| | | | | | | | | | | | |
|---|---|---|---|---|---|---|---|---|---|---|---|
| $3.7 \pm 0.3$ | $6.0 \pm 0.7$ | $66 \pm 5$ | $3.6 \pm 0.4$ | $6.0 \pm 0.6$ | $52 \pm 6$ | $3.2 \pm 0.6$ | $3.3 \pm 0.5$ | $69 \pm 6$ | $3.1 \pm 0.5$ | $3.3 \pm 0.6$ | $53 \pm 5$ |

†MEAN ± SEM (in BU)
‡MEAN ± SEM (in %)
*All significance determined by Student's t test Compared to normals
$^a p < 0.001$
$^b p < 0.005$
$^c p < 0.025$
$^i p < 0.02 = c*$
$^d p < 0.05$
$^e p < 0.001$
Compared to pre rTCMS II
$^y p < 0.01$ ¢ = m*
$^f p < 0.05$
$^g p < 0.02$
$^h p < 0.025$
$^l p < 0.05$
m: <0.005m

TABLE 45

Changes in phantageusia and phantosmia in 13 patients with hyposmia, hypogeusia, phantosmia and/or phantageusia pre and post rTCMS II

| | PHANTAGEUSIA | | PHANTOSMIA | |
|---|---|---|---|---|
| PATIENTS | PRE | POST | PRE | POST |
| TOTAL(13) | $39 \pm 10^{\dagger l}$ | $9 \pm 5^g$ | $47 \pm 8$ | $0^a$ |
| MEN(4) | $52 \pm 15$ | $6 \pm 5^h$ | $49 \pm 10$ | $0^f$ |
| WOMEN(9) | $34 \pm 6^k$ | $12 \pm 6^g$ | $44 \pm 5$ | $0^f$ |

†MEAN ± SEM [in %, of most intense distortions experienced throughout waking state]
$ Significance determined by Student's t test
*All results compared to pre rTCMS II and pre and post rTCMS I
$^a p < 0.001$ with respect to pre rTCMS II and post rTCMS I
$^f p < 0.001$ compared to pre rTCMS II and post rTCMS I
$^k p < 0.001$ compared to pre rTCMS I
$^l p < 0.005$ compared to pre rTCMS I
$^g p < 0.02$ compared to pre rTCMS II
$^h p < 0.025$ compared to pre rTCMS II

What is claimed is:

1. A method comprising:
    (i) detecting a cyclic nucleotide level in a human nasal mucus or human saliva specimen;
    (ii) comparing the cyclic nucleotide level of the nasal mucus or saliva specimen to a cyclic nucleotide level of a control population; and
    (iii) diagnosing loss or distortion of taste in the human based on a decreased level of the cyclic nucleotide for the nasal mucus or saliva specimen compared to the cyclic nucleotide level of the control population, wherein the cyclic nucleotide level is detected by an immunoassay;
    and wherein the method further comprises determining at least one of a detection threshold (DT), a recognition threshold (RT), or a magnitude estimation (ME) for four tastants: sodium chloride (NaCl), sucrose, hydrogen chloride (HCl) and urea.

2. The method of claim 1, wherein the specimen is human nasal mucus.

3. The method of claim 1, wherein the specimen is human saliva.

4. The method of claim 1, wherein the cyclic nucleotide is cyclic adenosine monophosphate or cyclic guanosine monophosphate.

5. The method of claim 1, wherein the cyclic nucleotide is cyclic adenosine monophosphate.

6. The method of claim 1, wherein the cyclic nucleotide is cyclic guanosine monophosphate.

7. The method of claim 1, further comprising treating the said loss or distortion of taste.

8. The method of claim 7, wherein the treating comprises administering a phosphodiesterase inhibitor.

9. The method of claim 8, wherein the phosphodiesterase inhibitor is theophylline.

10. The method of claim 8, wherein the administering is by oral administration.

11. The method of claim 8, wherein the administering is by nasal administration.

12. The method of claim 8, wherein the phosphodiesterase inhibitor is formulated as a powder.

13. The method of claim 8, wherein the phosphodiesterase inhibitor is formulated in liquid.

14. The method of claim 8, wherein the administering is performed daily.

15. The method of claim 1, wherein the immunoassay uses an antibody selective for a cyclic nucleotide.

16. The method of claim 1, wherein the immunoassay is an enzyme-linked immunosorbent assay.

17. The method of claim 1, wherein the immunoassay is a luminescent immunoassay.

18. The method of claim 1, wherein the immunoassay is a fluorescence immunoassay.

19. The method of claim 8, wherein the immunoassay is an enzyme-linked immunosorbent assay.

20. The method of claim 8, wherein the immunoassay is a luminescent immunoassay.

21. The method of claim 8, wherein the immunoassay is a fluorescence immunoassay.

22. The method of claim 3, wherein the human saliva is parotid saliva.

\* \* \* \* \*